(12) United States Patent
Rose et al.

(10) Patent No.: US 12,091,452 B2
(45) Date of Patent: Sep. 17, 2024

(54) SAFE AND EFFECTIVE METHOD OF TREATING LUPUS WITH ANTI-IL12/IL23 ANTIBODY

(71) Applicant: Janssen Biotech, Inc., Horsham, PA (US)

(72) Inventors: Shawn Rose, Horsham, PA (US); Carrie Wagner, Broomall, PA (US)

(73) Assignee: Janssen Biotech, Inc., Horsham, PA (US)

( * ) Notice: Subject to any disclaimer, the term of this patent is extended or adjusted under 35 U.S.C. 154(b) by 39 days.

(21) Appl. No.: 16/139,683

(22) Filed: Sep. 24, 2018

(65) Prior Publication Data

US 2019/0092853 A1 Mar. 28, 2019

Related U.S. Application Data

(60) Provisional application No. 62/730,748, filed on Sep. 13, 2018, provisional application No. 62/585,858, filed on Nov. 14, 2017, provisional application No. 62/562,701, filed on Sep. 25, 2017.

(51) Int. Cl.
| | | |
|---|---|---|
| *A61K 39/00* | (2006.01) | |
| *A61K 9/00* | (2006.01) | |
| *A61K 45/06* | (2006.01) | |
| *A61K 47/18* | (2017.01) | |
| *A61P 29/00* | (2006.01) | |
| *A61P 37/06* | (2006.01) | |
| *C07K 16/24* | (2006.01) | |

(52) U.S. Cl.
CPC .......... *C07K 16/244* (2013.01); *A61K 9/0019* (2013.01); *A61K 45/06* (2013.01); *A61K 47/183* (2013.01); *A61P 29/00* (2018.01); *A61P 37/06* (2018.01); *A61K 2039/505* (2013.01); *C07K 2317/565* (2013.01)

(58) Field of Classification Search
CPC ............................................ A61K 2039/55538
See application file for complete search history.

(56) References Cited

U.S. PATENT DOCUMENTS

| | | | |
|---|---|---|---|
| 5,457,038 A | 10/1995 | Trinchieri | |
| 5,547,852 A | 8/1996 | Seiler | |
| 5,648,467 A | 7/1997 | Trinchieri | |
| 5,780,597 A | 7/1998 | Gately | |
| 5,811,523 A | 9/1998 | Trinchieri | |
| 5,891,680 A | 4/1999 | Lieschke | |
| 6,086,876 A | 7/2000 | Karp | |
| 6,225,117 B1 | 5/2001 | Gately | |
| 6,300,478 B1 | 10/2001 | Trinchieri | |
| 6,338,848 B1 | 1/2002 | Leonard | |
| 6,495,667 B1 | 12/2002 | Bazan | |
| 6,902,734 B2 * | 6/2005 | Giles-Komar | ............ A61P 9/00 424/145.1 |
| 6,914,128 B1 | 7/2005 | Salfeld | |
| 7,063,964 B2 | 6/2006 | Giles-Komar et al. | |
| 7,166,285 B2 * | 1/2007 | Giles-Komar | .......... A61P 31/00 424/145.1 |
| 7,279,157 B2 | 10/2007 | Giles-Komar et al. | |
| 7,560,247 B2 | 7/2009 | Giles-Komar et al. | |
| 7,887,807 B2 * | 2/2011 | Giles-Komar | .......... A61P 29/00 424/145.1 |
| 8,084,233 B2 | 12/2011 | Giles-Komar et al. | |
| 8,329,171 B2 | 12/2012 | Giles-Komar et al. | |
| 8,703,141 B2 | 4/2014 | Giles-Komar et al. | |
| 9,409,984 B2 | 8/2016 | Giles-Komar et al. | |
| 9,676,848 B2 * | 6/2017 | Giles-Komar | ............. A61P 1/00 |
| 9,803,010 B2 * | 10/2017 | Reichert | .......... A61K 39/39591 |
| 9,862,766 B2 * | 1/2018 | Giles-Komar | .......... A61P 19/08 |
| 10,259,867 B2 * | 4/2019 | Giles-Komar | ..... A61K 39/3955 |
| 2005/0214293 A1 | 9/2005 | Giles-Komar | |
| 2009/0202549 A1 * | 8/2009 | Giles-Komar | .......... A61K 45/06 424/139.1 |
| 2015/0147337 A1 | 5/2015 | Reichert et al. | |
| 2016/0115227 A1 | 4/2016 | Brod | |
| 2017/0002060 A1 | 1/2017 | Bolen et al. | |
| 2017/0121417 A1 | 5/2017 | Jansson et al. | |
| 2019/0248884 A1 | 8/2019 | Giles-Komar et al. | |
| 2020/0062841 A1 | 2/2020 | Giles-Komar | |

FOREIGN PATENT DOCUMENTS

| | | |
|---|---|---|
| CL | 6882000 | 3/2000 |
| EP | 0640689 | 3/1995 |
| EP | 790255 | 8/1997 |
| EP | 433827 | 3/1998 |
| EP | 804581 | 9/2001 |
| EP | 1137766 | 9/2005 |
| WO | 9005147 | 5/1990 |
| WO | 9205256 | 4/1992 |

(Continued)

OTHER PUBLICATIONS

NCT02349061 (Pub date Aug. 3, 2016) , p. 1-7 (Year: 2016).*
STELARA® (ustekinumab) administration instruction revised Sep. 2016., p. 1-37. (Year: 2016).*
Janssen Biotech, Inc., U.S. Appl. No. 16/677,120.
A. U. Gubler et. al (Coexpression of Two Distinct Genes is Required to Generate Secreted Bioactive Cytotoxic Lymphocyte Maturation Factor) Proc. Natl. acad. Sci. USA. vol. 88. pp. 4143-4147—(May 1991) Immunology.
A. U. Gubler et. al (Clonic and Expression of Cytotoxic Lymphocyte Maturation Factor (CLMF) a Heterodimeric Lymphokine That Potentiates NR. LAK NA D T-Cell Reponses) Abstracts Journal of celluar Biochemistry Supplement 15 F: 70 (1991) 1 page.

(Continued)

*Primary Examiner* — Prema M Mertz
(74) *Attorney, Agent, or Firm* — Riverside Law LLP

(57) ABSTRACT

A method of treating active Systemic Lupus Erythematosus (SLE) in a patient by administering a clinically proven safe and clinically proven effective amount of an anti-IL-12/IL-23p40 antibody or an anti-IL-23 antibody, e.g., the anti-IL-12/IL-23p40 antibody ustekinumab, wherein the patient achieves a significant improvement in disease activity.

5 Claims, 3 Drawing Sheets
Specification includes a Sequence Listing.

(56) References Cited

FOREIGN PATENT DOCUMENTS

| WO | 9633735 | 10/1996 |
|---|---|---|
| WO | 9715327 | 5/1997 |
| WO | 9937682 | 7/1999 |
| WO | 0034459 | 6/2000 |
| WO | 0056772 | 9/2000 |
| WO | 0119373 | 3/2001 |
| WO | 2009114040 | 9/2009 |
| WO | WO 2017/049035 A1 | 3/2017 |

OTHER PUBLICATIONS

Alvin S. Stern et al—(Purification to Homogeneity and Partial Characterization of Cytotoxic Lymphocyte Maturation Factor From Human B-Lymphoblastoid Cells) (Jun. 11, 1990) F. Hoffmann La Roche Inc. Nutley NJ USA. Proc. National Acad. Sci. USA (vol. 87,pp. 6808-6812—Sep. 1990—Immunology).

M. Gately et. al. (Regulation of Human Lymphocyte Proliferation by a Heterodimeric Cytokine IL-12 (Cytotoxic Lymphocyte Maturation Factor) vol. 147—874-882 No. 3. (Aug. 1, 1991).(The Journal of Immunology).

R. Chizzonite et. al. (IL-12 Monoclonal Antibodies Specific for the 40-KdA Subunit Block Receptor Binding and Biologic Activity on Activated Human Lymphoblasts.) vol. 147,1548-1556—No. 5, (Sep. 1, 1991) The Journal of Immunology.

Susan H. Chan et. al. (Introduction of Interferon Production by Natural Killer Cell Stimulatory Factor Characterization of the Responder Cells and Synergy With Other Inducers) (The Rockefeller University Press)—0022-1007/91/04/0869/—vol. 173 Apr. 1991—pp. 869-879.

Annalisa D'andrea et al. (Production of Natural Killer Cell Stimulatory Factor (Interleukin 12) by Peripheral Blood Mononuclear Cell) J. Exp. Med. The Rockefeller university press—0022-1007/92/11/1387 vol. 176 Nov. 1992. pp. 1387-1398.

Markus F. Neurath et. al. (Antibodies to Interleukin 12 Abrogate Established Experimental Colitis in Mice) The Journal of Experimental Medicine—vol. 182—Nov. 1995—pp. 1281-1290.

R.W. Carter et. al. (Production and Characterization of Monoclonal Antibodies to Human Interleukin-12) Hybrididona 16: 363-369 (1997).

Nicolas M. Valiante et. al. ( Role of the Production of Natural Killer Cell Stimulatory Factor (NKSF/IL-12) in the Ability of B Cell Lines to Stimulate T and NK Cell Proliferation). Cellunar Immunology 145, 187-198—(1992).

Rainer Duchmann et. al. ( Tolerance Towards Resident Intestinal Flora in Mice is Abrogated in Experimental Colitis and Restores by Treatment With Intelukin-1 or Antibodies to Interleukin-12) European Journal of Immunology, 26: 934-938 (1996).

Michiko Kobayashi et. al. I ( Identification and Purification of Natural Killer Cell Stimulatory Factor (NKSF) a Cytokine With Multiple Biologic Efects on Human Lymphocytes) J. Exp. Med. The Rockefeller university Press—vol. 170—(Sep. 1989) pp. 827-845.

Sylvie Trembleau et. al. (The Role of IL-12 in the Induction of Organ-Specific Autoimmune Diseases), Immunology Today, 16(8): 383-386 (1995).

Nikhil, Yawalkar et al.; "Expression of interleukin-12 is increased in psoriatic skin", Journal of Investigative Dermatology, Dec. 1998, pp. 1053-1057; vol. 111, No. 6; XP00800577; ISSN: 0022-202X, abstract.

Hong, et al., "IL-12, Independently of IFN-☐ Plays a Crucial Role in the Pathogenesis of a Murine Psoriasis-Like Skin Disorder," Journal of Immunology, 162: 7480-7491 (1999).

Malfait, et al., "Blockade of IL-12 during the induction of collagen-induced arthritis (CIA) markedly attenuates the severity of the arthritis," Clinical and Experimental Immunology, 111:327-383 (1998).

PCT International Search Report PCT/US01/24720 dated Jul. 30, 2002, 9 pages.

Eduardo A. Padlan, "Anatomy of the Antibody Molecule," Molecular Immunology, 31(3): 169-217 (1994).

Carter, et al., "Production and Characterization of Monoclonal Antibodies to Human Interleukin-12," Hybridoma, 16(4): 363-369 (1997).

Casipit, et al., "Improving the binding affinity of an antibody using molecular modeling and site-directed mutagenesis," Protein Science, 7: 1671-1680 (1998).

Schildbach, et al., "Modulation of antibody affinity by a non-contact residue," Protein Science, 2: 206-214 (1993).

Romagnani, et al., "T cells and cytokines in Crohn's Disease," Current Opinion in Immunology, 9: 793-799 (1997).

Merrill et al., "Efficacy and Safety of Rituximab in Moderately-to-Severely Active Systemic Lupus Erythematosus." Arthritis & Rheumatism, 62(1): 222-233 (2010).

Anonymous: "A Multicenter. Randomized, Double-blind, Placebo-controlled, Proof-of-Concept Study of Ustekinumab in Subjects With Active Systemic Lupus Erythematosus". Janssen Research & Development* Clinical Protocol. approval date: Jan. 18, 2017, uploaded on: May 15, 2018. pp. 1-148.

Anonymous: "NCT02349061: A Phase 2a. Efficacy and Safety Study of Ustekinumab in Systemic Lupus Erythematosus". Sep. 5, 2017 (Sep. 5, 2017). XP055802677. Retrieved from the Internet: URL:https://clinicaltrials.gov/ct2/history/NCT02349061?V35=View#StudyPageTop [retrieved on May 10, 2021].

Klein Rachel et al: "Development of the CLASI as a Tool to Measure Disease Severity and Responsiveness to Therapy in Cutaneous Lupus Erythematosus", Archives of Dermatology, vol. 147, No. 2, Feb. 1, 2011 (Feb. 1, 2011), p. 203, XP055802684.

Laurie S. Davis et al: "Research and therapeutics-traditional and emerging therapies in systemic lupus erythematosus", Rheumatology, vol. 56, No. suppL 1, Mar. 27, 2017 (Mar. 27, 2017), pp. i100-i113, XP055476518.

Leng R X et al: "IL-23: A Promising Therapeutic Target for Systemic Lupus Erythematosus", Archives of Medical Research, Instituto Mexicano Del Seguro Social, Mexico, MX, vol. 41, No. 3, Apr. 1, 2010 (Apr. 1, 2010), pp. 221-225, XP027078888.

Van Vollenhoven R et al: "Efficacy and safety of ustekinumab, an interleukin 12/23 inhibitor, in patients with active systemic lupus erythematosus: results of a phase 2, randomised placebo-controlled study (S7A:8)", Lupus Science and Medicine, Mar. 21, 2018 (Mar. 21, 2018), pp. A28-A29, XP055802467.

Van Vollenhoven Ronald F et al: "Efficacy and safety of ustekinumab, an IL-12 and IL-23 inhibitor, in patients with active systemic lupus erythematosus: results of a multicentre, double-blind. phase 2, randomised, controlled study". The Lancet. Elsevier. Amsterdam. NL. vol. 392. No. 10155. Sep. 21, 2018 (Sep. 21, 2018). pp. 1330-1339.

Ceccarelli, et al., "The Role of Disease Activity Score 28 in the Evaluation of Articular Involvement in Systemic Lupus Erythematosus", The Scientific World Journal, vol. 204, 6 pages, Article ID 236842, http://dx.doi.org/10.1155/2014/236842.

History of Changes for Study: NCT023496061 A Phase 2a, Efficacy and Safety Study of Ustekinumab in Systemic Lupus Erythematosus, ClinicalTrials.gov archive, Sep. 5, 2017, 13 pages, https://clinicaltrials.gov/ct2/show/NCT02349061.

Jolly, et al., "Validation of the Cutaneous Lupus Disease Area and Severity Index (CLASI) using physician- and patient-assessed health outcome measures", J Am Acad Dermatol, 2013, vol. 68, No. 4,p. 618-623,doi: 10.1016/j.jaad.2012.08.035.

Albrecht, et al., "The CLASI (Cutaneous Lupus Erythematosus Disease Area and Severity Index): An Outcome Instrument for Cutaneous Lupus Erythematosus," Journal of Investigations in Dermatology, 125: 889-894 (2005).

Peter F. Barnes, M.D., "Diagnosing Latent Tuberculosis Infection Turning Glitter to Gold," American Journal of Respiratory and Critical Care Medicine, 170: 5-6 (2004).

Bennett, et al., "Interferon and Granulopoiesis Signatures in Systemic Lupus Erythematosus Blood," The Journal of Experimental Medicine, 197 (6): 711-723 (2003).

Brock, et al., "Comparison of Tuberculin Skin Test and New Specific Blood Test in Tuberculosis Contacts," American Journal of Respiratory and Critical Care Medicine, 170: 65-69 (2004).

(56) References Cited

OTHER PUBLICATIONS

Chen, et al., "Plasma IL-17A Is Increased in New-Onset SLE Patients and Associated with Disease Activity," Journal of Clinical Immunology, 30: 221-225 (2010).
Core Curriculum on Tuberculosis What the Clinician Should Know, Department of Health and Human Services, Fourth Edition, 1-144 (2000).
Crispin, et al., "Expanded Double Negative T Cells in Patients with Systemic Lupus Erythematosus Produce IL-17 and Infiltrate the Kidneys," Journal of Immunology, 181: 8761-8766 (2008).
Dahl, et al., "Ustekinumab in the Treatment of Refractory Chronic Cutaneous Lupus Erythematosus: A Case Report," Acta Dermato-Venerologica, 93: 1-2 (2013).
De Souza, et al., "Successful Treatment of Subacute Lupus Erythematosus With Ustekinumab," Arch Dermatology, 147 (8): 896-898 (2011).
Diel, et al., Predictive Value of a whole Blood IFN-γ Assay for the Development of Active Tuberculosis Disease after Recent Infection with *Mycobacterium tuberculosis*, American Journal of Respiratory and Critical Care Medicine, 177: 1164-1170 (2008).
Ewer, et al., "Comparison of T-cell-based assay with tuberculin skin test for diagnosis of *Mycobacterium tuberculosis* infection in a school tuberculosis outbreak," Lancet, 261: 1168-1173 (2003).
Feagan, et al., "Ustekinumab as Induction and Maintenance Therapy for Crohn's Disease," The New England Journal of Medicine, 375: 1946-1960 (2016).
Felson, et al., "American College of Rheumatology Preliminary Definition of Improvement in Rheumatoid Arthritis," Arthritis & Rheumatism, 38 (6): 727-735 (1995).
Ferrara, et al., "Routine Hospital Use of a New Commercial Whole Blood Interferon-γ Assay for the Diagnosis of Tuberculosis Infection," American Journal of Respiratory and Critical Care Medicine, 117: 631-635 (2005).
Fine, et al., "A prospective study of protein excretion using short-interval timed urine collections in patients with lupus nephritis," Kidney International, 76: 1284-1288 (2009).
Furie, et al., "Novel Evidence-Based systemic Lupus Erythematosus Responder Index," Arthritis & Rheumatism, 61 (9): 1143-1151 (2009).
Gladman, et al., "Systemic Lupus Erythematosus Disease Activity Index 2000," The Journal of Rheumatology, 29 (2): 288-291 (2000).
Han, et al., "Genome-wide association study in a Chinese Han population identifies nine new susceptibility loci for systemic lupus erythematosus," Nature Genetics, 41 (11): 1234-1239 (2009).
Harley, et al., "Genome-wide association scan in women with systemic lupus erythematosus identifies susceptibility variants in ITGAM, PXK, KIAA1542 and other loci," Nature Genetics, 40 (2): 24-210 (2008).
Hay, et al., "The BILAG index: a reliable and valid instrument for measuring clinical disease activity in systemic lupus erythematosus," Quarterly Journal of Medicine, 86: 447-458 (1993).
Higuchi, et al., "Use of QuantiFERON®—TB Gold to investigate tuberculosis contacts in a high school," Respirology, 12: 88-92 (2007).
Huang, et al., "Dysregulated expression of interleukin-23 and interleukin-12 subunits in systemic lupus erythematosus patients," Modern Rheumatology, 17 (3): 220-223 (2007).
Isenberg, et al., "BILAG 2004. Development and initial validation of an updated version of the British Isles Lupus Assessment Group's disease activity index for patients with systemic lupus erythematosus," Rheumatology, 44: 902-906 (2005).
Kim, et al., "No association between interleukin 23 receptor gene polymorphisms and systemic lupus erythematosus," Rheumatology Int. 30: 33-38 (2009).
Kobashi, et al., "Clinical evaluation of QuantiFERON TG-2G test for immunocompromised patients," European Respiratory Journal, 30: 945-950 (2007).
Krupp, et al., "The Fatigue Severity Scale Application to Patients with Multiple Sclerosis and Systemic Lupus Erythematosus," Arch. Neurol. 46: 1121-1123 (1989).

Linker-Israeli, et al., "Elevated Levels of Endogenous IL-6 in Systemic Lupus Erythematosus," The Journal of Immunology, 147: 117-123 (1991).
G. Matulis, Detection of latent tuberculosis in immunosuppressed patients with autoimmune diseases: performance of a *Mycobacterium tuberculosis* antigen-specific interferon γ assay, Ann. Rheum. Dis., 67: 84-90 (2008).
McHorney, et al., "The MOS 36-Item Short-Form Health Survey (SF-36): III. Tests of Data Quality, Scaling Assumptions, and Reliability Across Diverse Patient Groups," Medical Care, 32 (1): 40-66 (1994).
Mori, et al., "Specific Detection of Tuberculosis Infection and Interferon-γ-based Assay Using New Antigens," American Journal of Respiratory and Critical Care Medicine, 170: 59-64 (2004).
Navarra, et al., "Efficacy and safety of belimumab in patients with active systemic lupus erythematosus: a randomized, placebo-controlled, phase 3 trial," Lancet, 377: 721-731 (2011).
Niewold, et al., "High serum IFN-α activity if a heritable risk factor for systemic lupus erythematosus," Genes and Immunity, 8: 492-502 (2007).
Oh, et al., "Expression of interleukin-17 is correlated with interferon-α expression in cutaneous lesions of lupus erythematosus," Clinical and Experimental Dermatology, 36: 512-520 (2011).
Petri, et al., "Derivation and Validation of the Systemic Lupus International Collaborating Clinics Classification Criteria for Systemic Lupus Erythematosus," Arthritis & Rheumatism, 64 (8): 2677-2686 (2012).
Qiu, et al., "Glucocorticoid downregulates expression of IL-12 family cytokines in systemic lupus erythematosus patients," Lupus, 22: 1011-1016 (2013).
Samsa, et al., "Determining Clinically Important Differences in Health Status Measures," Pharmaeconomics, 15 (2): 141-155 (1999).
Sanchez, et al., "Analysis of interleukin-23 receptor (IL23R) gene polymorphisms in systemic lupus erythematosus," Tissue Antigens, 70: 233-237 (2007).
Sestak, et al., "The genetics of systemic lupus erythematosus and implications for targeted therapy," Ann. Rheum. Dis., 70 (Supplement 1): i37-i43 (2011).
Shah, et al., "Dysregulated balance of Th17 and Th1 cells in systemic lupus erythematosus," Arthritis Research & Therapy, 12: R53 (2010).
Tanasescu, et al., "IL-17 in cutaneous lupus erythematosus," European Journal of Internal Medicine, 21: 202-207 (2010).
Touma, et al., "SLEDAI-2K for a 30-day window," Lupus, 19: 49-50 (2010).
Tuoma, et al., "SLEDAI-2K Responder Index-50 (SRI-50)," Abstract PO2.D.7, Lupus, 19: 1-185 (2010).
Tuoma, et al., "SLEDAI-2K 10 days versus SLEDAI-2K 30 days in a cross-sectional and longitudinal evaluation," Abstract PO2.D.6, Lupus, 19: 1-185 (2010).
Tuoma, et al., "Development and Initial Validation of the Systemic Lupus Erythematosus Disease Activity Index 2000 Responder Index 50," The Journal of Rheumatology, 38 (2): 275-284 (2011).
Van Vollenhoven, et al., "Belimumab in the treatment of systemic lupus erythematosus: high disease activity predictors of response," Ann. Rheum. Dis., 71: 1343-1349 (2012).
Vincent, et al., "Clinical associations of serum interleukin-17 in systemic lupus erythematosus," Arthritis Research & Therapy, 15: R97 (2013).
D. Wallace, "Evaluation of Treatment Success in Systemic Lupus Erythematosus Clinical Trials: Development of the British Isles Lupus Assessment Group-Based Composite Lupus Assessment Endpoint," Abstract 2265, ACR/ARHP Scientific Meeting, Nov. 4-9, 2011.
Ware, et al., "The MOS 36-Item Short-Form Health Survey (SF-36) Conceptual Framework and Item Selection," Medical Care, 30 (6): 473-483 (1992).
John E. Ware, Jr., Ph.D., SF-36 Health Survey Update, Spine, 25 (24): 3130-3139 (2000).
Winchester, et al., "Response to ustekinumab I a patient with both severe psoriasis and hypertrophic cutaneous lupus," Lupus, 21: 1007-1010 (2012).

(56) References Cited

OTHER PUBLICATIONS

Wong, et al., "Hyperproduction of IL-23 and IL-17 in patients with systemic lupus erythematosus: Implications for Th17-mediated inflammation in auto-immunity," Clinical Immunology, 127: 385-393 (2008).

Yang, et al., "Th22, but not Th17 Might be a Good Index to Predict the Tissue Involvement of Systemic Lupus Erythematosus," Journal of Clinical Immunology, 33: 767-774 (2013).

Zhao, et al., "Increased serum interleukin 17 in patients with systemic lupus erythematosus," Mol. Biol. Rep., 37: 81-85 (2010).

Bing Li, et al., Framework selection can influence pharmacokinetics of a humanized therapeutic antibody through differences in molecule charge, mAbs, (2014) 6:5, 1255-1264, DOI: 10.4161/mabs.29809.

* cited by examiner

SAFE AND EFFECTIVE METHOD OF TREATING LUPUS WITH ANTI-IL12/IL23 ANTIBODY

CROSS-REFERENCE TO RELATED APPLICATIONS

This application claims the benefit of U.S. Provisional Application Ser. No. 62/562,701, filed 25 Sep. 2017, U.S. Provisional Application Ser. No. 62/585,858, filed 14 Nov. 2017 and U.S. Provisional Application Ser. No. 62/730,748, filed 13 Sep. 2018. The entire contents of the aforementioned applications are incorporated herein by reference in their entireties.

SEQUENCE LISTING

The instant application contains a Sequence Listing which has been submitted electronically in ASCII format and is hereby incorporated by reference in its entirety. Said ASCII copy, created on 6 Sep. 2018, is named JBI5139SEQLIST.txt and is 13/382 bytes in size.

FIELD OF THE INVENTION

The present invention relates to methods for treating lupus with an antibody that binds human IL-12 and/or human IL-23 proteins. In particular, the present invention relates to methods of treating active Systemic Lupus Erythematosus (SLE) in a patient by administering a clinically proven safe and clinically proven effective amount of an anti-IL-12/IL-23p40 antibody or an anti-IL-23 antibody, e.g., the anti-IL-12/IL-23p40 antibody ustekinumab, and specific pharmaceutical compositions of the antibody.

BACKGROUND OF THE INVENTION

Interleukin (IL)-12 is a secreted heterodimeric cytokine comprised of 2 disulfide-linked glycosylated protein subunits, designated p35 and p40 for their approximate molecular weights. IL-12 is produced primarily by antigen-presenting cells and drives cell-mediated immunity by binding to a two-chain receptor complex that is expressed on the surface of T cells or natural killer (NK) cells. The IL-12 receptor beta-1 (IL-12Rβ1) chain binds to the p40 subunit of IL-12, providing the primary interaction between IL-12 and its receptor. However, it is IL-12p35 ligation of the second receptor chain, IL-12Rβ2, that confers intracellular signaling (e.g. STAT4 phosphorylation) and activation of the receptor-bearing cell (Presky et al, 1996). IL-12 signaling concurrent with antigen presentation is thought to invoke T cell differentiation towards the T helper 1 (Th1) phenotype, characterized by interferon gamma (IFNγ) production (Trinchieri, 2003). Th1 cells are believed to promote immunity to some intracellular pathogens, generate complement-fixing antibody isotypes, and contribute to tumor immunosurveillance. Thus, IL-12 is thought to be a significant component to host defense immune mechanisms.

It was discovered that the p40 protein subunit of IL-12 can also associate with a separate protein subunit, designated p19, to form a novel cytokine, IL-23 (Oppman et al, 2000). IL-23 also signals through a two-chain receptor complex. Since the p40 subunit is shared between IL-12 and IL-23, it follows that the IL-12Rβ1 chain is also shared between IL-12 and IL-23. However, it is the IL-23p19 ligation of the second component of the IL-23 receptor complex, IL-23R, that confers IL-23 specific intracellular signaling (e.g., STAT3 phosphorylation) and subsequent IL-17 production by T cells (Parham et al, 2002; Aggarwal et al. 2003). Recent studies have demonstrated that the biological functions of IL-23 are distinct from those of IL-12, despite the structural similarity between the two cytokines (Langrish et al, 2005).

Abnormal regulation of IL-12 and Th1 cell populations has been associated with many immune-mediated diseases since neutralization of IL-12 by antibodies is effective in treating animal models of psoriasis, multiple sclerosis (MS), rheumatoid arthritis, inflammatory bowel disease, insulin-dependent (type 1) diabetes mellitus, and uveitis (Leonard et al, 1995; Hong et al, 1999; Malfait et al, 1998; Davidson et al, 1998). IL-12 has also been shown to play a critical role in the pathogenesis of SLE in two independent mouse models of systemic lupus erythematosus (Kikawada et al. 2003; Dai et al. 2007.

Systemic lupus erythematosus (SLE) is a complex, chronic, heterogeneous autoimmune disease of unknown etiology that can affect almost any organ system, and which follows a waxing and waning disease course. Systemic lupus erythematosus occurs much more often in women than in men, up to 9 times more frequently in some studies, and often appears during the child-bearing years between ages 15 and 45. This disease is more prevalent in Afro-Caribbean, Asian, and Hispanic populations. In SLE, the immune system attacks the body's cells and tissue, resulting in inflammation and tissue damage which can harm the heart, joints, skin, lungs, blood vessels, liver, kidneys and nervous system. About half of the subjects diagnosed with SLE present with organ-threatening disease, but it can take several years to diagnose subjects who do not present with organ involvement. Some of the primary complaints of newly diagnosed lupus patients are arthralgia (62%) and cutaneous symptoms (new photosensitivity; 20%), followed by persistent fever and malaise.[39] The estimated annual incidence of lupus varies from 1.8 to 7.6 cases per 100,000 and the worldwide prevalence ranges from 14 to 172 cases per 100,000 people.[39] Patients with mild disease have mostly skin rashes and joint pain and require less aggressive therapy; regimens include nonsteroidal anti-inflammatory drugs (NSAIDs), anti-malarials (e.g., hydroxychloroquine, chloroquine, or quinacrine) and/or low dose corticosteroids. With more severe disease patients may experience a variety of serious conditions depending on the organ systems involved, including lupus nephritis with potential renal failure, endocarditis or myocarditis, pneumonitis, pregnancy complications, stroke, neurological complications, vasculitis and cytopenias with associated risks of bleeding or infection. Common treatments for more severe disease include immunomodulatory agents, such as methotrexate (MTX), azathioprine, cyclophosphamide, cyclosporine, high dose corticosteroids, biologic B cell cytotoxic agents or B cell modulators, and other immunomodulators. Patients with serious SLE have a shortening of life expectancy by 10 to 30 years, largely due to the complications of the disease, of standard of care therapy, and/or accelerated atherosclerosis. In addition, SLE has a substantial impact on quality of life, work productivity, and healthcare expenditures. Existing therapies for SLE are generally either cytotoxic or immunomodulatory, and may have notable safety risks. Newer treatments for SLE have provided only modest benefits over standard of care therapy. Thus, there is a large unmet need for new alternative treatments that can provide significant benefit in this disease without incurring a high safety risk.

SUMMARY OF THE INVENTION

The general and preferred embodiments are defined, respectively, by the independent and dependent claims appended hereto, which for the sake of brevity are incorporated by reference herein. Other preferred embodiments, features, and advantages of the various aspects of the invention will become apparent from the detailed description below taken in conjunction with the appended drawing figures.

In certain embodiments, the present invention provides a clinically proven safe and clinically proven effective method of treating lupus in a patient comprising intravenously (IV) and/or subcutaneously (SC) administering to the patient an anti-IL-12 and/or anti-IL-23 antibody.

In certain embodiments, the invention provides a clinically proven safe and clinically proven effective method of treating lupus in a patient comprising intravenously (IV) and/or subcutaneously (SC) administering to the patient an anti-IL-12 and/or anti-IL-23 antibody, wherein the anti-IL-12 and/or anti-IL-23 antibody is an anti-IL-12/23p40 antibody.

In certain embodiments, the invention provides a clinically proven safe and clinically proven effective method of treating lupus in a patient comprising intravenously (IV) and/or subcutaneously (SC) administering to the patient an anti-IL-12 and/or anti-IL-23 antibody, wherein the anti-IL-12 and/or anti-IL-23 antibody is an anti-IL-12/23p40.

In certain embodiments, the invention provides a clinically proven safe and clinically proven effective method of treating lupus in a patient comprising intravenously (IV) and/or subcutaneously (SC) administering to the patient an anti-IL-12 and/or anti-IL-23 antibody, wherein the anti-IL-12 and/or anti-IL-23 antibody is an anti-IL-12/23p40 antibody comprising: (i) the heavy chain CDR amino acid sequences of SEQ ID NO:1, SEQ ID NO:2, and SEQ ID NO:3; and (ii) the light chain CDR amino acid sequences of SEQ ID NO:4, SEQ ID NO:5, and SEQ ID NO:6 (corresponding to ustekinumab (Stelara® of Janssen Biotech, Inc.)).

In certain embodiments, the invention provides a clinically proven safe and clinically proven effective method of treating lupus in a patient comprising intravenously (IV) and/or subcutaneously (SC) administering to the patient an anti-IL-12 and/or anti-IL-23 antibody, wherein the anti-IL-12 and/or anti-IL-23 antibody is an anti-IL-12/23p40 antibody comprising: (i) the heavy chain variable domain amino acid sequence of SEQ ID NO:7; and (ii) the light chain variable domain amino acid sequence of SEQ ID NO:8 (corresponding to ustekinumab (Stelara® of Janssen Biotech, Inc.)).

In certain embodiments, the invention provides a clinically proven safe and clinically proven effective method of treating lupus in a patient comprising intravenously (IV) and/or subcutaneously (SC) administering to the patient an anti-IL-12 and/or anti-IL-23 antibody, wherein the anti-IL-12 and/or anti-IL-23 antibody is the anti-IL-12/23p40 antibody ustekinumab (Stelara®), comprising: (i) the heavy chain amino acid sequence of SEQ ID NO:10; and (ii) the light chain amino acid sequence of SEQ ID NO:11 (corresponding to ustekinumab (Stelara® of Janssen Biotech, Inc.)).

In certain embodiments, the present invention provides a composition comprising an anti-IL-12 and/or anti-IL-23 antibody for use in a clinically proven safe and clinically proven effective method of treating lupus in a patient comprising intravenously (IV) and/or subcutaneously (SC) administering to the patient the pharmaceutical composition comprising the anti-IL-12 and/or anti-IL-23 antibody.

In certain embodiments, the present invention provides a composition comprising an anti-IL-12 and/or anti-IL-23 antibody for use in a clinically proven safe and clinically proven effective method of treating lupus in a patient comprising intravenously (IV) and/or subcutaneously (SC) administering to the patient the pharmaceutical composition comprising an anti-IL-12 and/or anti-IL-23 antibody, wherein the anti-IL-12 and/or anti-IL-23 antibody is an anti-IL-12/23p40 antibody.

In certain embodiments, the present invention provides a composition comprising an anti-IL-12 and/or anti-IL-23 antibody for use in a clinically proven safe and clinically proven effective method of treating lupus in a patient comprising intravenously (IV) and/or subcutaneously (SC) administering to the patient the pharmaceutical composition comprising an anti-IL-12 and/or anti-IL-23 antibody, wherein the anti-IL-12 and/or anti-IL-23 antibody is an anti-IL-12/23p40 antibody.

In certain embodiments, the present invention provides a composition comprising an anti-IL-12 and/or anti-IL-23 antibody for use in a clinically proven safe and clinically proven effective method of treating lupus in a patient comprising intravenously (IV) and/or subcutaneously (SC) administering to the patient the pharmaceutical composition comprising an anti-IL-12 and/or anti-IL-23 antibody, wherein the anti-IL-12 and/or anti-IL-23 antibody is an anti-IL-12/23p40 antibody comprising: (i) the heavy chain CDR amino acid sequences of SEQ ID NO:1, SEQ ID NO:2, and SEQ ID NO:3; and (ii) the light chain CDR amino acid sequences of SEQ ID NO:4, SEQ ID NO:5, and SEQ ID NO:6.

In certain embodiments, the present invention provides a composition comprising an anti-IL-12 and/or anti-IL-23 antibody for use in a clinically proven safe and clinically proven effective method of treating lupus in a patient comprising intravenously (IV) and/or subcutaneously (SC) administering to the patient the pharmaceutical composition comprising an anti-IL-12 and/or anti-IL-23 antibody, wherein the anti-IL-12 and/or anti-IL-23 antibody is an anti-IL-12/23p40 antibody comprising: (i) the heavy chain variable domain amino acid sequence of SEQ ID NO:7; and (ii) the light chain variable domain amino acid sequence of SEQ ID NO:8.

In certain embodiments, the present invention provides a composition comprising an anti-IL-12 and/or anti-IL-23 antibody for use in a clinically proven safe and clinically proven effective method of treating lupus in a patient comprising intravenously (IV) and/or subcutaneously (SC) administering to the patient the pharmaceutical composition comprising an anti-IL-12 and/or anti-IL-23 antibody, wherein the anti-IL-12 and/or anti-IL-23 antibody is the anti-IL-12/23p40 antibody ustekinumab (Stelara®), comprising: (i) the heavy chain amino acid sequence of SEQ ID NO:10; and (ii) the light chain amino acid sequence of SEQ ID NO:11.

In certain embodiments, the present invention provides a pharmaceutical composition for intravenously (IV) administration comprising an anti-IL-12/IL-23p40 antibody comprising: (i) the heavy chain CDR amino acid sequences of SEQ ID NO:1, SEQ ID NO:2, and SEQ ID NO:3; and (ii) the light chain CDR amino acid sequences of SEQ ID NO:4, SEQ ID NO:5, and SEQ ID NO:6; in a solution comprising 10 mM L-histidine, 8.5% (w/v) sucrose, 0.04% (w/v) polysorbate 80, 0.4 mg/mL L methionine, and 20 µg/mL EDTA disodium salt, dehydrate, at pH 6.0.

In certain embodiments, the present invention provides a pharmaceutical composition for subcutaneous (SC) administration comprising an anti-IL-12/IL-23p40 antibody comprising: (i) the heavy chain CDR amino acid sequences of SEQ ID NO:1, SEQ ID NO:2, and SEQ ID NO:3; and (ii) the light chain CDR amino acid sequences of SEQ ID NO:4, SEQ ID NO:5, and SEQ ID NO:6; in a solution comprising 6.7 mM L-histidine, 7.6% (w/v) sucrose, 0.004% (w/v) polysorbate 80, at pH 6.0.

In certain embodiments, the present invention provides a pharmaceutical composition for intravenously (IV) administration comprising an anti-IL-12/IL-23p40 antibody comprising: (i) the heavy chain variable domain amino acid sequence of SEQ ID NO:7; and (ii) the light chain variable domain amino acid sequence of SEQ ID NO:8; in a solution comprising 10 mM L-histidine, 8.5% (w/v) sucrose, 0.04% (w/v) polysorbate 80, 0.4 mg/mL L methionine, and 20 µg/mL EDTA disodium salt, dehydrate, at pH 6.0.

In certain embodiments, the present invention provides a pharmaceutical composition for subcutaneous (SC) administration comprising an anti-IL-12/IL-23p40 antibody comprising: (i) the heavy chain variable domain amino acid sequence of SEQ ID NO:7; and (ii) the light chain variable domain amino acid sequence of SEQ ID NO:8; in a solution comprising 6.7 mM L-histidine, 7.6% (w/v) sucrose, 0.004% (w/v) polysorbate 80, at pH 6.0.

In certain embodiments, the present invention provides a pharmaceutical composition for intravenously (IV) administration comprising the anti-IL-12/23p40 antibody ustekinumab (Stelara®), comprising: (i) the heavy chain amino acid sequence of SEQ ID NO:10; and (ii) the light chain amino acid sequence of SEQ ID NO:11; in a solution comprising 10 mM L-histidine, 8.5% (w/v) sucrose, 0.04% (w/v) polysorbate 80, 0.4 mg/mL L methionine, and 20 µg/mL EDTA disodium salt, dehydrate, at pH 6.0.

In certain embodiments, the present invention provides a pharmaceutical composition for subcutaneous (SC) administration comprising the anti-IL-12/23p40 antibody ustekinumab (Stelara®), comprising: (i) the heavy chain amino acid sequence of SEQ ID NO:10; and (ii) the light chain amino acid sequence of SEQ ID NO:11; in a solution comprising 6.7 mM L-histidine, 7.6% (w/v) sucrose, 0.004% (w/v) polysorbate 80, at pH 6.0.

In certain embodiments, the present invention provides a method of treating lupus in a patient comprising subcutaneously administering an anti-IL-23 specific antibody (also referred to as IL-23p19 antibody), e.g., guselkumab and risankizumab (BI-655066), tildrakizumab (MK-322).

In certain embodiments, the composition used in the method of the invention comprises a pharmaceutical composition comprising: an anti-IL-23 specific antibody in an amount from about 1.0 µg/ml to about 1000 mg/ml, specifically at 50 mg or 100 mg. In a preferred embodiment, the anti-IL-23 specific antibody is guselkumab at 100 mg/mL; 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

In certain embodiments, the composition used in the method of the invention comprises an isolated anti-IL23 specific antibody, e.g., guselkumab, at 100 mg/mL; 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

In certain embodiments, method of the invention comprises administering a pharmaceutical composition comprising an isolated anti-IL-23 specific antibody, e.g., guselkumab, at 100 mg/mL; 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w).

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the initial IV dose is 6.0 mg/kg±1.5 mg/kg.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the initial IV dose is 260 mg for patients with body weight ≥35 kg and ≤55 kg, 390 mg for patients with body weight >55 kg and ≤85 kg, and 520 mg for patients with body weight >85 kg.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, and wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), wherein the SC dose is 90 mg.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the patient is a responder to the treatment with the antibody and is identified as having an improvement beginning at 12 weeks of treatment and a statistically significant improvement in disease activity as determined by an improvement in the Systemic Lupus Erythematosus Disease Activity Index 2000 (SLEDAI-2K) score of ≥4 (SRI-4 response) by week 24 of treatment with the antibody, with the response sustained out to week 48.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the patient is a responder to the treatment with the antibody and is identified as having an improvement beginning at 12 weeks of treatment and a statistically significant reduction in the risk of a new British Isles Lupus Assessment Group (BILAG) flare, defined as ≥1 new BILAG A domain score or ≥2 new BILAG B domain score, by week 24 of treatment with the antibody.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the patient is a responder to the treatment with the antibody and is identified as having an improvement beginning at 12 weeks after start of treatment and there is a statistically significant increase in the proportion of patients with a 50% improvement from baseline in Cutaneous Lupus Erythematosus Disease Area and Severity Index (CLASI) score for patients that received treatment with the antibody compared to patients treated with a placebo.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the patient is a responder to the treatment with the antibody and is identified as having an improvement beginning at 12 weeks of treatment and a statistically significant improvement in disease activity as determined by a 50% improvement from baseline joint disease activity by week 24 of treatment with the antibody.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the patient is a responder to the treatment with the antibody and is identified as having a statistically significant improvement in disease activity by week 24 of treatment that is sustained through 1 year of treatment, wherein disease activity is determined by one or more criteria selected from the group consisting of: a decrease from baseline in the Systemic Lupus Erythematosus Disease Activity Index 2000 (SLEDAI-2K) score of ≥4 (SRI-4 response), proportion of patients with a 50% improvement from baseline in Cutaneous Lupus Erythematosus Disease Area and Severity Index (CLASI) score, and a 50% improvement from baseline joint disease activity.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the antibody for use with IV administration is in a pharmaceutical composition comprising a solution comprising 10 mM L-histidine, 8.5% (w/v) sucrose, 0.04% (w/v) polysorbate 80, 0.4 mg/mL L methionine, and 20 µg/mL EDTA disodium salt, dehydrate, at pH 6.0.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the antibody for use with SC administration is in a pharmaceutical composition comprising a solution comprising 6.7 mM L-histidine, 7.6% (w/v) sucrose, 0.004% (w/v) polysorbate 80, at pH 6.0.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, wherein the method further comprises administering to the patient one or more additional drugs used to treat lupus.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, wherein the method further comprises administering to the patient one or more additional drugs used to treat lupus, and wherein the additional drug is selected from the group consisting of: immunosuppressive agents, non-steroidal anti-inflammatory drugs (NSAIDs), methotrexate (MTX), anti-B-cell surface marker antibodies, angiotensin converting enzyme inhibitors, angiotensin receptor blockers, antimalarials, mycophenolate mofetil, mycophenolic acid, azathioprine, 6-mercaptopurine, belimumab, anti-CD20 antibodies, rituximab, corticosteroids, and co-stimulatory modifiers.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region of the amino acid sequence of SEQ ID NO:7 and a light chain variable region of the amino acid sequence of SEQ ID NO:8.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region of the amino acid sequence of SEQ ID NO:7 and a light chain variable region of the amino acid sequence of SEQ ID NO:8, and wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w).

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region of the amino acid sequence of SEQ ID NO:7 and a light chain variable region of the amino acid sequence of SEQ ID NO:8, and wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), wherein the initial IV dose is 6.0 mg/kg±1.5 mg/kg.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region of the amino acid sequence of SEQ ID NO:7 and a light chain variable region of the amino acid sequence of SEQ ID NO:8, and wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), wherein the initial IV dose is 260 mg for patients with body weight >35 kg and <55 kg, 390 mg for patients with body weight >55 kg and <85 kg, and 520 mg for patients with body weight >85 kg.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region of the amino acid sequence of SEQ ID NO:7 and a light chain variable region of the amino acid sequence of SEQ ID NO:8, and wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), wherein the SC dose is 90 mg.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region of the amino acid sequence of SEQ ID NO:7 and a light chain variable region of the amino acid sequence of SEQ ID NO:8, and wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), wherein the patient is a responder to the treatment with the antibody and is identified as having an improvement beginning at 12 weeks of treatment and a statistically significant improvement in disease activity as determined by a decrease from baseline in the Systemic Lupus Erythematosus Disease Activity Index 2000 (SLEDAI-2K) score of ≥4 (SRI-4 response) by week 24 of treatment with the antibody.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region of the amino acid sequence of SEQ ID NO:7 and a light chain variable region of the amino acid sequence of SEQ ID NO:8, and wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), wherein the patient is a responder to the treatment with the antibody and is identified as having an improvement beginning at 12 weeks of treatment and a statistically significant reduction in the risk of a new British Isles Lupus Assessment Group (BILAG) flare, defined as ≥1 new BILAG A domain score or ≥2 new BILAG B domain score, by week 24 of treatment with the antibody.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region of the amino acid sequence of SEQ ID NO:7 and a light chain variable region of the amino acid sequence of SEQ ID NO:8, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the patient is a responder to the treatment with the antibody and is identified as having an improvement beginning at 12 weeks of treatment and there is a statistically significant increase in the proportion of patients with a 50% improvement from baseline in Cutaneous Lupus Erythematosus Disease Area and Severity Index (CLASI) score for patients that received treatment with the antibody compared to patients treated with a placebo.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region of the amino acid sequence of SEQ ID NO:7 and a light chain variable region of the amino acid sequence of SEQ ID NO:8, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the patient is a responder to the treatment with the antibody and is identified as having an improvement beginning at 12 weeks of treatment and a statistically significant improvement in disease activity as determined by a 50% improvement from baseline joint disease activity by week 24 of treatment with the antibody.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region of the amino acid sequence of SEQ ID NO:7 and a light chain variable region of the amino acid sequence of SEQ ID NO:8, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the patient is a responder to the treatment with the antibody and is identified as having a statistically significant improvement in disease activity by week 24 of treatment that is sustained through 1 year of treatment, wherein disease activity is determined by one or more criteria selected from the group consisting of: a decrease from baseline in the Systemic Lupus Erythematosus Disease Activity Index 2000 (SLEDAI-2K) score of ≥4 (SRI-4 response), proportion of patients with a 50% improvement from baseline in Cutaneous Lupus Erythematosus Disease Area and Severity Index (CLASI) score, and a 50% improvement from baseline joint disease activity.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region of the amino acid sequence of SEQ ID NO:7 and a light chain variable region of the amino acid sequence of SEQ ID NO:8, and wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), wherein the antibody for use with IV administration is in a pharmaceutical composition comprising a solution comprising 10 mM L-histidine, 8.5% (w/v) sucrose, 0.04% (w/v) polysorbate 80, 0.4 mg/mL L methionine, and 20 µg/mL EDTA disodium salt, dehydrate, at pH 6.0.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region of the amino acid sequence of SEQ ID NO:7 and a light chain variable region of the amino acid sequence of SEQ ID NO:8, and wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), wherein the antibody for use with SC administration is in a pharmaceutical composition comprising a solution comprising 6.7 mM L-histidine, 7.6% (w/v) sucrose, 0.004% (w/v) polysorbate 80, at pH 6.0.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region of the amino acid sequence of SEQ ID NO:7 and a light chain variable region of the amino acid sequence of SEQ ID NO:8, wherein the method further comprises administering to the patient one or more additional drugs used to treat lupus.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises a heavy chain variable region of the amino acid sequence of SEQ ID NO:7 and a light chain variable region of the amino acid sequence of SEQ ID NO:8, wherein the method further comprises administering to the patient one or more additional drugs used to treat lupus, wherein the additional drug is selected from the group consisting of: immunosuppressive agents, non-steroidal anti-inflammatory drugs (NSAIDs), methotrexate (MTX), anti-B-cell surface marker antibodies, angiotensin converting enzyme inhibitors, angiotensin receptor blockers, anti-malarials, mycophenolate mofetil, mycophenolic acid, azathioprine, 6-mercaptopurine, belimumab, anti-CD20 antibodies, rituximab, corticosteroids, and co-stimulatory modifiers.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises the anti-IL-12/23p40 antibody ustekinumab (Stelara®), comprising: (i) the heavy chain amino acid sequence of SEQ ID NO:10; and (ii) the light chain amino acid sequence of SEQ ID NO:11.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises the anti-IL-12/23p40 antibody ustekinumab (Stelara®), comprising: (i) the heavy chain amino acid sequence of SEQ ID NO:10; and (ii) the light chain amino acid sequence of SEQ ID NO:11, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w).

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises the anti-IL-12/23p40 antibody ustekinumab (Stelara®), comprising: (i) the heavy chain amino acid sequence of SEQ ID NO:10; and (ii) the light chain amino acid sequence of SEQ ID NO:11, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the initial IV dose is 6.0 mg/kg±1.5 mg/kg.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises the anti-IL-12/23p40 antibody ustekinumab (Stelara®), comprising: (i) the heavy chain amino acid sequence of SEQ ID NO:10; and (ii) the light chain amino acid sequence of SEQ ID NO:11, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the initial IV dose is 260 mg for patients with body weight ≥35 kg and ≤55 kg, 390 mg for patients with body weight >55 kg and ≤85 kg, and 520 mg for patients with body weight >85 kg.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises the anti-IL-12/23p40 antibody ustekinumab (Stelara®), comprising: (i) the heavy chain amino acid sequence of SEQ ID NO:10; and (ii) the light chain amino acid sequence of SEQ ID NO:11, and wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), wherein the SC dose is 90 mg.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises the anti-IL-12/23p40 antibody ustekinumab (Stelara®), comprising: (i) the heavy chain amino acid sequence of SEQ ID NO:10; and (ii) the light chain amino acid sequence of SEQ ID NO:11, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the patient is a responder to the treatment with the antibody and is identified as having a statistically significant improvement in disease activity as determined by a decrease from baseline in the Systemic Lupus Erythematosus Disease Activity Index 2000 (SLEDAI-2K) score of ≥4 (SRI-4 response) by week 24 of treatment with the antibody.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises the anti-IL-12/23p40 antibody ustekinumab (Stelara®), comprising: (i) the heavy chain amino acid sequence of SEQ ID NO:10; and (ii) the light chain amino acid sequence of SEQ ID NO:11, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the patient is a responder to the treatment with the antibody and is identified as having a statistically significant reduction in the risk of a new British Isles Lupus Assessment Group (BILAG) flare, defined as ≥1 new BILAG A domain score or ≥2 new BILAG B domain score, by week 24 of treatment with the antibody.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises the anti-IL-12/23p40 antibody ustekinumab (Stelara®), comprising: (i) the heavy chain amino acid sequence of SEQ ID NO:10; and (ii) the light chain amino acid sequence of SEQ ID NO:11, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein there is a statistically significant increase in the proportion of patients with a 50% improvement from baseline in Cutaneous Lupus Erythematosus Disease Area and Severity Index (CLASI) score for patients that received treatment with the antibody compared to patients treated with a placebo.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises the anti-IL-12/23p40 antibody ustekinumab (Stelara®), comprising: (i) the heavy chain amino acid sequence of SEQ ID NO:10; and (ii) the light chain amino acid sequence of SEQ ID NO:11, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the patient is a responder to the treatment with the antibody and is identified as having a statistically significant improvement in disease activity by week 24 of treatment that is sustained through 1 year of treatment, wherein disease activity is determined by one or more criteria selected from the group consisting of: a decrease from baseline in the Systemic Lupus Erythematosus Disease Activity Index 2000 (SLEDAI-2K) score of ≥4 (SRI-4 response), proportion of patients with a 50% improvement from baseline in Cutaneous Lupus Erythematosus Disease Area and Severity Index (CLASI) score, and a 50% improvement from baseline joint disease activity.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises the anti-IL-12/23p40 antibody ustekinumab (Stelara®), comprising: (i) the heavy chain amino acid sequence of SEQ ID NO:10; and (ii) the light chain amino acid sequence of SEQ ID NO:11, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the antibody for use with IV administration is in a pharmaceutical composition comprising a solution comprising 10 mM L-histidine, 8.5% (w/v) sucrose, 0.04% (w/v) polysorbate 80, 0.4 mg/mL L methionine, and 20 μg/mL EDTA disodium salt, dehydrate, at pH 6.0.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises the anti-IL-12/23p40 antibody ustekinumab (Stelara®), comprising: (i) the heavy chain amino acid sequence of SEQ ID NO:10; and (ii) the light chain amino acid sequence of SEQ ID NO:11, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the antibody for use with SC administration is in a pharmaceutical composition comprising a solution comprising 6.7 mM L-histidine, 7.6% (w/v) sucrose, 0.004% (w/v) polysorbate 80, at pH 6.0.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises the anti-IL-12/23p40 antibody ustekinumab (Stelara®), comprising: (i) the heavy chain amino acid sequence of SEQ ID NO:10; and (ii) the light chain amino acid sequence of SEQ ID NO:11, wherein the method further comprises administering to the patient one or more additional drugs used to treat lupus.

In certain embodiments, the present invention provides a method of treating active Systemic Lupus Erythematosus (SLE) in a patient, comprising administering an anti-IL-12/IL-23p40 antibody to the patient in a clinically proven safe and clinically proven effective amount, wherein the antibody comprises the anti-IL-12/23p40 antibody ustekinumab (Stelara®), comprising: (i) the heavy chain amino acid sequence of SEQ ID NO:10; and (ii) the light chain amino acid sequence of SEQ ID NO:11, wherein the method further comprises administering to the patient one or more additional drugs used to treat lupus, and wherein the additional drug is selected from the group consisting of: immunosuppressive agents, non-steroidal anti-inflammatory drugs (NSAIDs), methotrexate (MTX), anti-B-cell surface marker antibodies, angiotensin converting enzyme inhibitors, angiotensin receptor blockers, anti-malarials, mycophenolate mofetil, mycophenolic acid, azathioprine, 6-mercaptopurine, belimumab, anti-CD20 antibodies, rituximab, corticosteroids, and co-stimulatory modifiers.

DETAILED DESCRIPTION OF THE PREFERRED EMBODIMENTS

Figure 1:
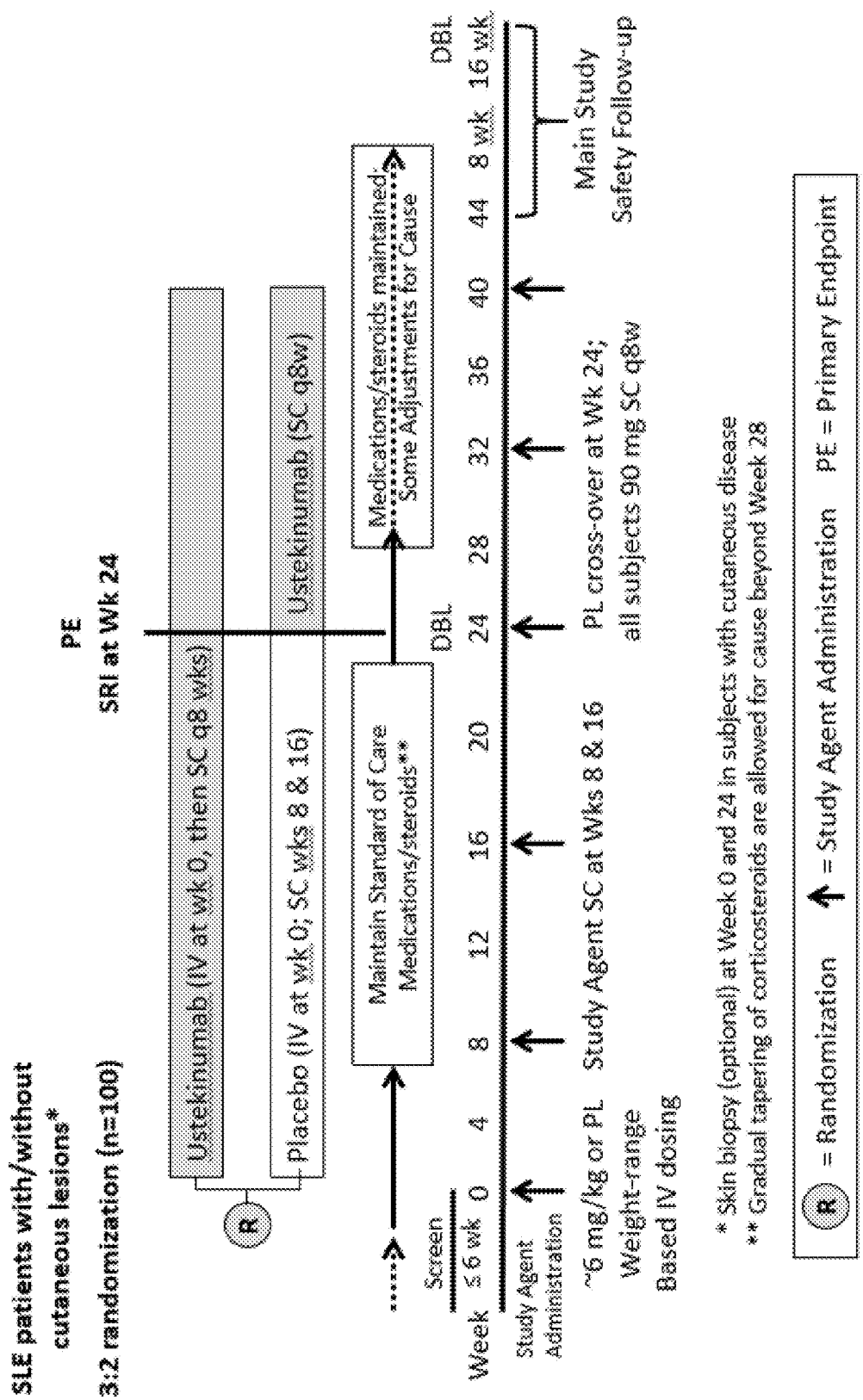
FIG. 1: Shows a Schematic Overview of the Main Study (Screening through 16-Week Safety Follow-Up. Abbreviations: DBL=database lock; FU=follow-up; IV=intravenous; PE=primary endpoint; PL=placebo; q8w=every 8 weeks; SC=subcutaneous; SLE=systemic lupus erythematosus; SRI=SLEDAI-2K Responder Index; Wks=weeks.

As used herein the method of treatment of lupus comprises administering isolated, recombinant and/or synthetic anti-IL-12, IL-23 and IL12/23p40 human antibodies and diagnostic and therapeutic compositions, methods and devices.

As used herein, an "anti-IL-12 antibody," "anti-IL-23 antibody," "anti-IL-12/23p40 antibody," "IL-12/23p40 antibody," "antibody portion," or "antibody fragment" and/or "antibody variant" and the like include any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an IL-12 and/or IL-23 receptor or binding protein, which can be incorporated into an antibody of the present invention. Such antibody optionally further affects a specific ligand, such as but not limited to, where such antibody modulates, decreases, increases, antagonizes, agonizes, mitigates, alleviates, blocks, inhibits, abrogates and/or interferes with at least one IL-12/23 activity or binding, or with IL-12/23 receptor activity or binding, in vitro, in situ and/or in vivo. As a non-limiting example, a suitable anti-IL-12/23p40 antibody, specified portion or variant of the present invention can bind at least one IL-12/23 molecule, or specified portions, variants or domains thereof. A suitable anti-IL-12/23p40 antibody, specified portion, or variant can also optionally affect at least one of IL-12/23 activity or function, such as but not limited to, RNA, DNA or protein synthesis, IL-12/23 release, IL-12/23 receptor signaling, membrane IL-12/23 cleavage, IL-12/23 activity, IL-12/23 production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof.

Functional fragments include antigen-binding fragments that bind to a mammalian IL-12/23. For example, antibody fragments capable of binding to IL-12/23 or portions thereof, including, but not limited to, Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $C_H1$ domain and/or hinge region of the heavy chain. The various portions of antibodies can be joined together chemically by conventional techniques, or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. A "human antibody" may also be an antibody that is derived from or closely matches human germline immunoglobulin sequences. Human antibodies may include amino acid residues not encoded by germline immunoglobulin sequences (e.g., mutations introduced by random or site-specific mutagenesis in vitro or by somatic mutation in vivo). Often, this means that the human antibody is substantially non-immunogenic in humans. Human antibodies have been classified into groupings based on their amino acid sequence similarities. Accordingly, using a sequence similarity search, an antibody with a similar linear sequence can be chosen as a template to create a human antibody. Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. Thus, a human antibody is distinct from a chimeric or humanized antibody.

It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Anti-IL-12/23p40 antibodies (also termed IL-12/23p40 antibodies) (or antibodies to IL-23) useful in the methods and compositions of the present invention can optionally be characterized by high affinity binding to IL-12/23p40 (or to IL-23) and, optionally and preferably, having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., Lancet 344: 1125-1127 (1994), entirely incorporated herein by reference). "Low immunogenicity" can also be defined as the incidence of titrable levels of antibodies to the anti-IL-12 antibody in patients treated with anti-IL-12 antibody as occurring in less than 25% of patients treated, preferably, in less than 10% of patients treated with the recommended dose for the recommended course of therapy during the treatment period.

The terms "clinically proven efficacy" and "clinically proven effective" as used herein in the context of a dose, dosage regimen, treatment or method refer to the effectiveness of a particular dose, dosage or treatment regimen. Efficacy can be measured based on change in the course of the disease in response to an agent of the present invention. For example, an anti-IL12/23p40 or anti-IL23 antibody of the present invention (e.g., the anti-IL12/23p40 antibody usetkinumab) is administered to a patient in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. The degree of improvement generally is determined by a physician, who may make this determination based on signs, symptoms, biopsies, or other test results, and who may also employ questionnaires that are administered to the subject, such as quality-of-life questionnaires developed for a given disease. For example, an anti-IL12/23p40 or anti-IL23 antibody of the present invention may be administered to achieve an improvement in a patient's condition related to Systemic Lupus Erythematosus (SLE). Improvement may be indicated by an improvement in an index of disease activity, by amelioration of clinical symptoms or by any other measure of disease activity. One such index of disease is the Systemic Lupus Erythematosus Disease Activity Index 2000 (SLEDAI-2K) score. The SLEDAI-2K is an established, validated disease activity index for Systemic Lupus Erythematosus (SLE) that is based on the presence of 24 features in 9 organ systems and measures disease activity in SLE patients in the previous 30 days. Features are scored if present within the last 30 days with more severe features having higher scores and the scores are added to determine the total SLEDAI-2K score, which ranges from 0 to 105. Other disease activity indexes for systemic lupus erythematosus (SLE) disease activity assessment include, for example, the Cutaneous Lupus Erythematosus Disease Area and Severity Index (CLASI) and the British Isles Lupus Assessment Group (BILAG) index.

The CLASI index consists of 2 scores; the first summarizes the activity of the disease while the second is a measure of the damage done by the disease. The scores are calculated by simple addition based on the extent of the symptoms. Higher activity and damage scores indicate worse disease activity. The BILAG index is a measure of disease activity consisting of 97 questions in 9 organ systems, each put into 1 of 5 categories (A, B, C, D, E) depending on presence of items. Higher scores indicate more disease involvement.

The term "clinically proven safe", as it relates to a dose, dosage regimen, treatment or method with an anti-IL12/23p40 or anti-IL23 antibody of the present invention (e.g., the anti-IL12/23p40 antibody usetkinumab), refers to a favorable risk:benefit ratio with an acceptable frequency and/or acceptable severity of treatment-emergent adverse events (referred to as AEs or TEAEs) compared to the standard of care or to another comparator. An adverse event is an untoward medical occurrence in a patient administered a medicinal product. In particular, safe as it relates to a dose, dosage regimen or treatment with an anti-IL12/23p40 or anti-IL23 antibody of the present invention refers to with an acceptable frequency and/or acceptable severity of adverse events associated with administration of the antibody if attribution is considered to be possible, probable, or very likely due to the use of the anti-IL12/23p40 or anti-IL23 antibody.

As used herein, unless otherwise noted, the term "clinically proven" (used independently or to modify the terms "safe" and/or "effective") shall mean that it has been proven by a clinical trial wherein the clinical trial has met the approval standards of U.S. Food and Drug Administration, EMEA or a corresponding national regulatory agency. For example, the clinical study may be an adequately sized, randomized, double-blinded study used to clinically prove the effects of the drug.

Utility

The isolated nucleic acids of the present invention can be used for production of at least one anti-IL-12/23p40 (or anti-IL-23) antibody or specified variant thereof, which can be used to measure or effect in an cell, tissue, organ or animal (including mammals and humans), to diagnose, monitor, modulate, treat, alleviate, help prevent the incidence of, or reduce the symptoms of, at least one IL-12/23 condition, selected from, but not limited to, at least one of an immune disorder or disease, a cardiovascular disorder or disease, an infectious, malignant, and/or neurologic disorder or disease, or other known or specified IL-12/23 related condition.

Such a method can comprise administering an effective amount of a composition or a pharmaceutical composition comprising at least one anti-IL-12/23p40 (or anti-IL-23) antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 µg/ml serum concentration per single, multiple, or continuous administration, or any effective range or value therein, as done and determined using known methods, as described herein or known in the relevant arts.

Citations

All publications or patents cited herein, whether or not specifically designated, are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, NY (1987-2001); Sambrook, et al., Molecular Cloning: A Laboratory Manual, 2nd Edition, Cold Spring Harbor, NY (1989); Harlow and Lane, antibodies, a Laboratory Manual, Cold Spring Harbor, NY (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

Antibodies of the Present Invention—Production and Generation

At least one anti-IL-12/23p40 (or anti-IL-23) used in the method of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, NY (1989); Harlow and Lane, antibodies, a Laboratory Manual, Cold Spring Harbor, NY (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001), each entirely incorporated herein by reference.

A preferred anti-IL-12/23p40 antibody is ustekinumab (Stelara®) having the heavy chain variable region amino acid sequence of SEQ ID NO:7 and the light chain variable region amino acid sequence of SEQ ID NO:8 and having the heavy chain CDR amino acid sequences of SEQ ID NO:1, SEQ ID NO:2, and SEQ ID NO: 3; and the light chain CDR amino acid sequences of SEQ ID NO:4, SEQ ID NO:5, and SEQ ID NO:6. A preferred anti-IL-23 antibody is guselkumab (also referred to as CNTO1959). Other anti-IL-23 antibodies have sequences listed herein and are described in U.S. Pat. No. 7,935,344, the entire contents of which are incorporated herein by reference).

Human antibodies that are specific for human IL-12/23p40 or IL-23 proteins or fragments thereof can be raised against an appropriate immunogenic antigen, such as an isolated IL-12/23p40 protein, IL-23 protein and/or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line, such as, but not limited to, Sp2/0, Sp2/0-AG14, NSO, NS1, NS2, AE-1, L.5, L243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like, or heteromylomas, fusion products thereof, or any cell or fusion cell derived therefrom, or any other suitable cell line as known in the art) (see, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably, the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsried/Planegg, DE; Biovation, Aberdeen, Scotland, UK; BioInvent, Lund, Sweden; Dyax Corp., Enzon, Affymax/Biosite; Xoma, Berkeley, CA; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260(May 12, 1994); PCT/GB94/01422; PCT/GB94/02662; PCT/GB97/01835; (CAT/MRC); WO90/14443; WO90/14424; WO90/14430; PCT/U594/1234; WO92/18619; WO96/07754; (Scripps); WO96/13583, WO97/08320 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, predecessor of Applied Molecular Evolution (AME), each entirely incorporated herein by reference)) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, MA; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source that is non-human, e.g., but not limited to, mouse, rat, rabbit, non-human primate or other mammal. These non-human amino acid residues are replaced by residues often referred to as "import" residues, which are typically taken from an "import" variable, constant or other domain of a known human sequence.

Known human Ig sequences are disclosed, e.g.,
www.ncbi.nlm.nih.gov/entrez/query.fcgi;
www.ncbi.nih.gov/igblast;
www.atcc.org/phage/hdb.html;
www.mrc-cpe.cam.ac.uk/ALIGNMENTS.php;
www.kabatdatabase.com/top.html; ftp.ncbi.nih.gov/repository/kabat;
www.sciquest.com;
www.abcam.com;
www.antibodyresource.com/onlinecomp.html;
www.public.iastate.edu/~pedro/research tools.html;
www.whfreeman.com/immunology/CH05/kuby05.html;
www.hhmi.org/grants/lectures/1996/vlab;
www.path.cam.ac.uk/~mrc7/mikeimages.html;
www.mcb.harvard.edu/BioLinks/Immunology.html;
www.immunologylink.com; pathbox.wustl.edu/~hcenter/index.html;
www.appliedbiosystems.com;
www.nal.usda.gov/awic/pubs/antibody;
www.m.ehime-u.ac.jp/~yasuhito/Elisa.html;
www.biodesign.com;
www.cancerresearchuk.org;
www.biotech.ufl.edu;
www.isac-net.org; baserv.uci.kun.nl/~jraats/links1.html;
www.recab.uni-hd.de/immuno.bme.nwu.edu;
www.mrc-cpe.cam.ac.uk;
www.ibt.unam.mx/vir/V_mice.html;
www.bioinforg.uk/abs; antibody.bath.ac.uk;
www.unizh.ch;
www.cryst.bbk.ac.uk/~ubcg07s;
www.nimr.mrc.ac.uk/CC/ccaewg/ccaewg.html;
www.path.cam.ac.uk/~mrc7/humanisation/TAHHP.html;
www.ibt.unam.mx/vir/structure/stat_aim.html;
www.biosci.missouri.edu/smithgp/index.html;
www.jerini.de;
Kabat et al., Sequences of Proteins of Immunological Interest, U.S. Dept. Health (1983)
Each of the above entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antigen binding. Accordingly, part or all of the non-human or human CDR sequences are maintained while the non-human sequences of the variable and constant regions may be replaced with human or other amino acids.

Antibodies can also optionally be humanized or human antibodies engineered with retention of high affinity for the antigen and other favorable biological properties. To achieve this goal, humanized (or human) antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

In addition, the human anti-IL-12/23p40 (or anti-IL-23) specific antibody used in the method of the present invention may comprise a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6.

In other embodiments, the human anti-IL-12/23p40 (or anti-IL-23) specific antibody used in the method of the present invention may comprise a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework (readily available at the sources of known human Ig sequences described above). In other embodiments, at least FRH1, FRH2, FRH3, or FRH4 is a germline sequence (e.g., human germline) or comprises human consensus sequences for the particular framework. In preferred embodiments, the framework region is a fully human framework region.

Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype. Alternatively, or additionally, it may be useful to combine amino acid modifications with one or more further amino acid modifications that alter C1q binding and/or the complement dependent cytotoxicity function of the Fc region of an IL-23 binding molecule. The starting polypeptide of particular interest may be one that binds to C1q and displays complement dependent cytotoxicity (CDC). Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO0042072, which is hereby incorporated by reference.

As disclosed above, one can design an Fc region of the human anti-IL-12/23p40 (or anti-IL-23) specific antibody of the present invention with altered effector function, e.g., by modifying C1q binding and/or FcγR binding and thereby changing complement dependent cytotoxicity (CDC) activity and/or antibody-dependent cell-mediated cytotoxicity (ADCC) activity. "Effector functions" are responsible for activating or diminishing a biological activity (e.g., in a subject). Examples of effector functions include, but are not limited to: C1q binding; CDC; Fc receptor binding; ADCC; phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of the human anti-IL-12/23p40 (or anti-IL-23) antibody with improved C1q binding and improved FcγRIIIbinding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

Fc mutations can also be introduced in engineer to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, J. Biol. Chem. 276:6591-6604).

Another type of amino acid substitution serves to alter the glycosylation pattern of the Fc region of the human anti-IL-12/23p40 (or anti-IL-23) specific antibody. Glycosylation of an Fc region is typically either N-linked or O-linked. N-linked refers to the attachment of the carbohydrate moiety to the side chain of an asparagine residue. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation sites that are not present in the polypeptide. Addition of glycosylation sites to the Fc region of a human IL-23 specific antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the human anti-IL-12/23p40 (or anti-IL-23) specific antibody of the present invention is expressed in cells that express beta (1,4)-N-acetylglucosaminyltransferase III (GnT III), such that GnT III adds GlcNAc to the human anti-IL-12/23p40 (or anti-IL-23) antibody. Methods for producing antibodies in such a fashion are provided in WO/9954342, WO/03011878, patent publication 20030003097A1, and Umana et al., Nature Biotechnology, 17:176-180, February 1999; all of which are herein specifically incorporated by reference in their entireties.

The human anti-IL-12/23p40 (or anti-IL-23) antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-IL-12/23p40 (or anti-IL-23) antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. *Nature* 368:856-859 (1994), Taylor et al., *Int. Immunol.* 6(4)579-591 (1994), Green et al, *Nature Genetics* 7:13-21 (1994), Mendez et al., *Nature Genetics* 15:146-156 (1997), Taylor et al., *Nucleic Acids Research* 20(23):6287-6295 (1992), Tuaillon et al., *Proc Natl Acad Sci USA* 90(8)3720-3724 (1993), Lonberg et al., *Int Rev Immunol* 13(1):65-93 (1995) and Fishwald et al., *Nat Biotechnol* 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, CA), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, U.S. Pat. Nos. 5,427,908, 5,580,717, assigned to Affymax; U.S. Pat. No. 5,885,793, assigned to Cambridge antibody Technologies; U.S. Pat. No. 5,750,373, assigned to Genentech, U.S. Pat. Nos. 5,618,920, 5,595,898, 5,576,195, 5,698,435, 5,693,493, 5,698,417, assigned to Xoma, Colligan, supra; Ausubel, supra; or Sambrook, supra, each of the above patents and publications entirely incorporated herein by reference.

Antibodies used in the method of the present invention can also be prepared using at least one anti-IL-12/23p40 (or anti-IL-23) antibody encoding nucleic acid to provide transgenic animals or mammals, such as goats, cows, horses, sheep, rabbits, and the like, that produce such antibodies in their milk. Such animals can be provided using known methods. See, e.g., but not limited to, U.S. Pat. Nos. 5,827, 690; 5,849,992; 4,873,316; 5,849,992; 5,994,616; 5,565, 362; 5,304,489, and the like, each of which is entirely incorporated herein by reference.

Antibodies used in the method of the present invention can additionally be prepared using at least one anti-IL-12/23p40 (or anti-IL-23) antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. Each of the above references is entirely incorporated herein by reference.

The antibodies used in the method of the invention can bind human IL-12/IL-23p40 or IL-23 with a wide range of affinities ($K_D$). In a preferred embodiment, a human mAb can optionally bind human IL-12/IL-23p40 or IL-23 with high affinity. For example, a human mAb can bind human IL-12/IL-23p40 or IL-23 with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, NY (1984); Kuby, Janis *Immunology*, W. H. Freeman and Company: New York, NY (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Nucleic Acid Molecules

Using the information provided herein, for example, the nucleotide sequences encoding at least 70-100% of the contiguous amino acids of at least one of the light or heavy chain variable or CDR regions described herein, among other sequences disclosed herein, specified fragments, variants or consensus sequences thereof, or a deposited vector comprising at least one of these sequences, a nucleic acid molecule of the present invention encoding at least one IL-12/IL-23p40 or IL-23 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules used in the method of the present invention can include nucleic acid molecules comprising an open reading frame (ORF), optionally, with one or more introns, e.g., but not limited to, at least one specified portion of at least one CDR, such as CDR1, CDR2 and/or CDR3 of at least one heavy chain or light chain; nucleic acid molecules comprising the coding sequence for an anti-IL-12/IL-23p40 or IL-23 antibody or variable region; and nucleic acid molecules which comprise a nucleotide sequence substantially different from those described above but which, due to the degeneracy of the genetic code, still encode at least one anti-IL-12/IL-23p40 or IL-23 antibody as described herein and/or as known in the art. Of course, the genetic code is well known in the art. Thus, it would be routine for one skilled in the art to generate such degenerate nucleic acid variants that code for specific anti-IL-12/IL-23p40 or IL-23 antibodies used in the method of the present invention. See, e.g., Ausubel, et al., supra, and such nucleic acid variants are included in the present invention. Non-limiting examples of isolated nucleic acid molecules include nucleic acids encoding HC CDR1, HC CDR2, HC CDR3, LC CDR1, LC CDR2, and LC CDR3, respectively.

As indicated herein, nucleic acid molecules which comprise a nucleic acid encoding an anti-IL-12/IL-23p40 or IL-23 antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Selectively Hybridizing to a Polynucleotide as Described Herein

The method of the present invention uses isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides will encode at least a portion of an antibody. The polynucleotides embrace nucleic acid sequences that can be employed for selective hybridization to a polynucleotide encoding an antibody of the present invention. See, e.g., Ausubel, supra; Colligan, supra; each entirely incorporated herein by reference.

Construction of Nucleic Acids

The isolated nucleic acids can be made using (a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, are well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide used in the method of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses antisense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides used in the method of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, CA (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids used in the method of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention uses recombinant expression cassettes comprising a nucleic acid. A nucleic acid sequence, for example, a cDNA or a genomic sequence encoding an antibody used in the method of the present invention, can be used to construct a recombinant expression cassette that can be introduced into at least one desired host cell. A recombinant expression cassette will typically comprise a polynucleotide operably linked to transcriptional initiation regulatory sequences that will direct the transcription of the polynucleotide in the intended host cell. Both heterologous and non-heterologous (i.e., endogenous) promoters can be employed to direct expression of the nucleic acids.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide. For example, endogenous promoters can be altered in vivo or in vitro by mutation, deletion and/or substitution.

Vectors and Host Cells

The present invention also relates to vectors that include isolated nucleic acid molecules, host cells that are genetically engineered with the recombinant vectors, and the production of at least one anti-IL-23 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827, 739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody used in the method of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein used in the method of the present invention. Alternatively, nucleic acids can be expressed in a host cell by turning on (by manipulation) in a host cell that contains endogenous DNA encoding an antibody. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www. atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Antibody

An anti-IL-12/IL-23p40 or IL-23 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, NY, (1997-2001), e.g., Chapters 1, 4, 6, 8, 9, 10, each entirely incorporated herein by reference.

Antibodies used in the method of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-IL-12/IL-23p40 or IL-23 Antibodies

An anti-IL-12/IL-23p40 or IL-23 antibody according to the present invention includes any protein or peptide containing molecule that comprises at least a portion of an immunoglobulin molecule, such as but not limited to, at least one ligand binding portion (LBP), such as but not limited to, a complementarity determining region (CDR) of a heavy or light chain or a ligand binding portion thereof, a heavy chain or light chain variable region, a framework region (e.g., FR1, FR2, FR3, FR4 or fragment thereof, further optionally comprising at least one substitution, insertion or deletion), a heavy chain or light chain constant region, (e.g., comprising at least one CH1, hinge1, hinge2, hinge3, hinge4, CH2, or CH3 or fragment thereof, further optionally comprising at least one substitution, insertion or deletion), or any portion thereof, that can be incorporated into an antibody. An antibody can include or be derived from any mammal, such as but not limited to, a human, a mouse, a rabbit, a rat, a rodent, a primate, or any combination thereof, and the like.

The isolated antibodies used in the method of the present invention comprise the antibody amino acid sequences disclosed herein encoded by any suitable polynucleotide, or any isolated or prepared antibody. Preferably, the human antibody or antigen-binding fragment binds human IL-12/IL-23p40 or IL-23 and, thereby, partially or substantially neutralizes at least one biological activity of the protein. An antibody, or specified portion or variant thereof, that partially or preferably substantially neutralizes at least one biological activity of at least one IL-12/IL-23p40 or IL-23 protein or fragment can bind the protein or fragment and thereby inhibit activities mediated through the binding of IL-12/IL-23p40 or IL-23 to the IL-12 and/or IL-23 receptor or through other IL-12/IL-23p40 or IL-23-dependent or mediated mechanisms. As used herein, the term "neutralizing antibody" refers to an antibody that can inhibit an IL-12/IL-23p40 or IL-23-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-IL-12/IL-23p40 or IL-23 antibody to inhibit an IL-12/IL-23p40 or IL-23-dependent activity is preferably assessed by at least one suitable IL-12/IL-23p40 or IL-23 protein or receptor assay, as described herein and/or as known in the art. A human antibody can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4 (e.g., γ1, γ2, γ3, γ4). Antibodies of this type can be prepared by employing a transgenic mouse or other transgenic non-human mammal comprising at least one human light chain (e.g., IgG, IgA, and IgM) transgenes as described herein and/or as known in the art. In another embodiment, the anti-IL-23 human antibody comprises an IgG1 heavy chain and an IgG1 light chain.

An antibody binds at least one specified epitope specific to at least one IL-12/IL-23p40 or IL-23 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein.

Generally, the human antibody or antigen-binding fragment will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. The CDR sequences may be derived from human germline sequences or closely match the germline sequences. For example, the CDRs from a synthetic library derived from the original non-human CDRs can be used. These CDRs may be formed by incorporation of conservative substitutions from the original non-human sequence. In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3.

Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-IL-12/IL-23p40 or IL-23 specific antibody can comprise at least one of a heavy or light chain variable region having a defined amino acid sequence. For example, in a preferred embodiment, the anti-IL-12/IL-23p40 or IL-23 antibody comprises an anti-IL-12/IL-23p40 antibody with a heavy chain variable region comprising the amino acid sequence of SEQ ID NO:7 and a light chain variable region comprising the amino acid sequence of SEQ ID NO:8. The anti-IL-12/IL-23p40 or IL-23 specific antibody can also comprise at least one of a heavy or light chain having a defined amino acid sequence. In another preferred embodiment, the anti-IL-12/IL-23p40 or IL-23 antibody comprises an anti-IL-12/IL-23p40 antibody with a heavy chain comprising the amino acid sequence of SEQ ID NO:10 and a light chain comprising the amino acid sequence of SEQ ID NO:11. Antibodies that bind to human IL-12/IL-23p40 or IL-23 and that comprise a defined heavy or light chain variable region can be prepared using suitable methods, such as phage display (Katsube, Y., et al., *Int J Mol. Med*, 1(5):863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human IL-12/IL-23p40 or IL-23 or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human IL-12/IL-23p40 or IL-23 with high affinity (e.g., $K_D$ less than or equal to about $10^{-9}$M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include, without limitation, replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes

The amino acids that make up anti-IL-12/IL-23p40 or IL-23 antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

| SINGLE LETTER CODE | THREE LETTER CODE | NAME | THREE NUCLEOTIDE CODON(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

SEQUENCES

Example Anti-IL-12/IL-23p40 Antibody Sequences—STELARA® (ustekinumab)

Amino acid sequence of anti-IL-12/IL-23p40 antibody complementarity determining region heavy chain 1 (CDRH1): (SEQ ID NO:1)

TYWLG

Amino acid sequence of anti-IL-12/IL-23p40 antibody complementarity determining region heavy chain 2 (CDRH2): (SEQ ID NO:2)

IMSPVDSDIRYSPSFQG

Amino acid sequence of anti-IL-12/IL-23p40 antibody complementarity determining region heavy chain 3 (CDRH3): (SEQ ID NO:3)

Amino acid sequence of anti-IL-12/IL-23p40 antibody complementarity determining region light chain 1 (CDRL1): (SEQ ID NO:4)

RRPGQGYFDF

Amino acid sequence of anti-IL-12/IL-23p40 antibody complementarity determining region light chain 2 (CDRL2): (SEQ ID NO:5)

RASQGISSWLA

Amino acid sequence of anti-IL-12/IL-23p40 antibody complementarity determining region light chain 3 (CDRL3): (SEQ ID NO:6)

AASSLQS

Amino acid sequence of anti-IL-12/IL-23p40 antibody variable heavy chain region (CDRs underlined): (SEQ ID NO:7)

QQYNIYPYT

```
  1 EVQLVQSGAE VKKPGESLKI SCKGSGYSFT TYWLGWVRQM PGKGLDWIGI MSPVDSDIRY
 61 SPSFQGQVTM SVDKSITTAY LQWNSLKASD TAMYYCARRR PGQGYFDFWG QGTLVTVSS
```

Amino acid sequence of anti-IL-12/IL-23p40 antibody variable light chain region (CDRs underlined): (SEQ ID NO:8)

```
  1 DIQMTQSPSS LSASVGDRVT ITCRASQGIS SWLAWYQQKP EKAPKSLIYA ASSLQSGVPS
 61 RFSGSGSGTD FTLTISSLQP EDFATYYCQQ YNIYPYTFGQ GTKLEIKR
```

Amino acid sequence of anti-IL-12/IL-23p40 antibody heavy chain (CDRs underlined): (SEQ ID NO:10)

```
  1 EVQLVQSGAE VKKPGESLKI SCKGSGYSFT TYWLGWVRQM PGKGLDWIGI MSPVDSDIRY
 61 SPSFQGQVTM SVDKSITTAY LQWNSLKASD TAMYYCARRR PGQGYFDFWG QGTLVTVSSS
121 STKGPSVFPL APSSKSTSGG TAALGCLVKD YFPEPVTVSW NSGALTSGVH TFPAVLQSSG
181 LYSLSSVVTV PSSSLGTQTY ICNVNHKPSN TKVDKRVEPK SCDKTHTCPP CPAPELLGGP
241 SVFLFPPKPK DTLMISRTPE VTCVVVDVSH EDPEVKFNWY VDGVEVHNAK TKPREEQYNS
301 TYRVVSVLTV LHQDWLNGKE YKCKVSNKAL PAPIEKTISK AKGQPREPQV YTLPPSRDEL
361 TKNQVSLTCL VKGFYPSDIA VEWESNGQPE NNYKTTPPVL DSDGSFFLYS KLTVDKSRWQ
421 QGNVFSCSVM HEALHNHYTQ KSLSLSPGK
```

Amino acid sequence of anti-IL-12/IL-23p40 antibody light chain (CDRs underlined): (SEQ ID NO:11)

```
  1 DIQMTQSPSS LSASVGDRVT ITCRASQGIS SWLAWYQQKP EKAPKSLIYA ASSLQSGVPS
 61 RFSGSGSGTD FTLTISSLQP EDFATYYCQQ YNIYPYTFGQ GTKLEIKRTV AAPSVFIFPP
121 SDEQLKSGTA SVVCLLNNFY PREAKVQWKV DNALQSGNSQ ESVTEQDSKD STYSLSSTLT
181 LSKADYEKHK VYACEVTHQG LSSPVTKSFN RGEC
```

Amino Acid Sequence IL-12

Amino acid sequence of human interleukin (IL)-12 with alpha and beta subunits: (SEQ ID NO:9)

```
  1 RNLPVATPDP GMFPCLHHSQ NLLRAVSNML QKARQTLEFY PCTSEEIDHE DITKDKTSTV
 61 EACLPLELTK NESCLNSRET SFITNGSCLA SRKTSFMMAL CLSSIYEDLK MYQVEFKTMN
121 AKLLMDPKRQ IFLDQNMLAV IDELMQALNF NSETVPQKSS LEEPDFYKTK IKLCILLHAF
181 RIRAVTIDRV MSYLNASIWE LKKDVYVVEL DWYPDAPGEM VVLTCDTPEE DGITWTLDQS
```

```
241 SEVLGSGKTL TIQVKEFGDA GQYTCHKGGE VLSHSLLLLH KKEDGIWSTD ILKDQKEPKN

301 KTFLRCEAKN YSGRFTCWWL TTISTDLTFS VKSSRGSSDP QGVTCGAATL SAERVRGDNK

361 EYEYSVECQE DSACPAAEES LPIEVMVDAV HKLKYENYTS SFFIRDIIKP DPPKNLQLKP

421 LKNSRQVEVS WEYPDTWSTP HSYFSLTFCV QVQGKSKREK KDRVFTDKTS ATVICRKNAS

481 ISVRAQDRYY SSSWSEWASV PCS
```

An anti-IL-12/IL-23p40 or IL-23 antibody used in the method of the present invention can include one or more amino acid substitutions, deletions or additions, either from natural mutations or human manipulation, as specified herein.

The number of amino acid substitutions a skilled artisan would make depends on many factors, including those described above. Generally speaking, the number of amino acid substitutions, insertions or deletions for any given anti-IL-12/IL-23p40 or IL-23 antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-IL-12/IL-23p40 or IL-23 specific antibody that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one IL-12/IL-23p40 or IL-23 neutralizing activity. Sites that are critical for antibody binding can also be identified by structural analysis, such as crystallization, nuclear magnetic resonance or photoaffinity labeling (Smith, et al., J. Mol. Biol. 224:899-904 (1992) and de Vos, et al., Science 255:306-312 (1992)).

Anti-IL-12/IL-23p40 or IL-23 antibodies can include, but are not limited to, at least one portion, sequence or combination selected from 5 to all of the contiguous amino acids of at least one of SEQ ID NOs 1, 2, 3, 4, 5, 6, 7, 8, 10, or 11.

IL-12/IL-23p40 or IL-23 antibodies or specified portions or variants can include, but are not limited to, at least one portion, sequence or combination selected from at least 3-5 contiguous amino acids of the SEQ ID NOs above; 5-17 contiguous amino acids of the SEQ ID NOs above, 5-10 contiguous amino acids of the SEQ ID NOs above, 5-11 contiguous amino acids of the SEQ ID NOs above, 5-7 contiguous amino acids of the SEQ ID NOs above; 5-9 contiguous amino acids of the SEQ ID NOs above.

An anti-IL-12/IL-23p40 or IL-23 antibody can further optionally comprise a polypeptide of at least one of 70-100% of 5, 17, 10, 11, 7, 9, 119, 108, 449, or 214 contiguous amino acids of the SEQ ID NOs above. In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of the SEQ ID NOs above. For example, the amino acid sequence of a light chain variable region can be compared with the sequence of the SEQ ID NOs above, or the amino acid sequence of a heavy chain CDR3 can be compared with the SEQ ID NOs above. Preferably, 70-100% amino acid identity (i.e., 90, 91, 92, 93, 94, 95, 96, 97, 98, 99, 100 or any range or value therein) is determined using a suitable computer algorithm, as known in the art.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing:Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, MD).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990)). The BLAST X program is publicly available from NCBI and other sources (BLAST Manual, Altschul, S., et al., NCBINLM NIH Bethesda, Md. 20894: Altschul, S., et al., J. Mol. Biol. 215:403-410 (1990). The well-known Smith Waterman algorithm may also be used to determine identity.

Preferred parameters for polypeptide sequence comparison include the following:
(1) Algorithm: Needleman and Wunsch, J. Mol Biol. 48:443-453 (1970) Comparison matrix: BLOSSUM62 from Hentikoff and Hentikoff, Proc. Natl. Acad. Sci, USA. 89:10915-10919 (1992)
Gap Penalty: 12
Gap Length Penalty: 4
A program useful with these parameters is publicly available as the "gap" program from Genetics Computer Group, Madison Wis. The aforementioned parameters are the default parameters for peptide sequence comparisons (along with no penalty for end gaps).

Preferred parameters for polynucleotide comparison include the following:

(1) Algorithm: Needleman and Wunsch, J. Mol Biol. 48:443-453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid sequence comparisons.

By way of example, a polynucleotide sequence may be identical to another sequence, that is 100% identical, or it may include up to a certain integer number of nucleotide alterations as compared to the reference sequence. Such alterations are selected from the group consisting of at least one nucleotide deletion, substitution, including transition and transversion, or insertion, and wherein the alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the sequence by the numerical percent of the respective percent identity (divided by 100) and subtracting that product from the total number of nucleotides in the sequence, or: $n_n \le x_n - (x_n \cdot y)$,
wherein $n_n$ is the number of nucleotide alterations, $x_n$ is the total number of nucleotides in sequence, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting from $x_n$.

Alterations of a polynucleotide sequence encoding the the SEQ ID NOs above may create nonsense, missense or frameshift mutations in this coding sequence and thereby alter the polypeptide encoded by the polynucleotide following such alterations. Similarly, a polypeptide sequence may be identical to the reference sequence of the SEQ ID NOs above, that is be 100% identical, or it may include up to a certain integer number of amino acid alterations as compared to the reference sequence such that the percentage identity is less than 100%. Such alterations are selected from the group consisting of at least one amino acid deletion, substitution, including conservative and non-conservative substitution, or insertion, and wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the SEQ ID NOs above by the numerical percent of the respective percent identity (divided by 100) and then subtracting that product from the total number of amino acids in the SEQ ID NOs above, or: $n_a \le x_a - (x_a \cdot y)$, wherein $n_a$ is the number of amino acid alterations, $x_a$ is the total number of amino acids in the SEQ ID NOs above, and y is, for instance 0.70 for 70%, 0.80 for 80%, 0.85 for 85% etc., and wherein any non-integer produce of $x_a$ and y is rounded down to the nearest integer prior to subtracting it from $x_a$.

Exemplary heavy chain and light chain variable regions sequences and portions thereof are provided in the SEQ ID NOs above. The antibodies of the present invention, or specified variants thereof, can comprise any number of contiguous amino acid residues from an antibody of the present invention, wherein that number is selected from the group of integers consisting of from 10-100% of the number of contiguous residues in an anti-IL-12/IL-23p40 or IL-23 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and, preferably, at least 50%, 60%, or 70%, and, most preferably, at least 80%, 90%, or 95%-100% or more (including, without limitation, up to 10 times the specific activity) of that of the native (non-synthetic), endogenous or related and known antibody. Methods of assaying and quantifying measures of enzymatic activity and substrate specificity are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-$\Delta$9-octadecanoate ($C_{18}$, oleate), all cis-$\Delta$5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NETS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, CA (1996)). An activating group can be bonded directly to the organic group (e.g., hydrophilic polymer, fatty acid, fatty acid ester), or through a linker moiety, for example, a divalent $C_1$-$C_{12}$ group wherein one or more carbon atoms can be replaced by a heteroatom, such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified antibodies can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, CA (1996).

The method of the present invention also uses an anti-IL-12/IL-23p40 or IL-23 antibody composition comprising at least one, at least two, at least three, at least four, at least five, at least six or more anti-IL-12/IL-23p40 or IL-23 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-IL-12/IL-23p40 or IL-23 antibody amino acid sequence selected from the group consisting of 70-100% of the contiguous amino acids of the SEQ ID NOs above, or specified fragments, domains or variants thereof. Preferred anti-IL-12/IL-23p40 or IL-23 antibody compositions include at least one or two full length, fragments, domains or variants as at least one CDR or LBP containing portions of the anti-IL-12/IL-23p40 or IL-23 antibody sequence described herein, for example, 70-100% of the SEQ ID NOs above, or specified fragments, domains or variants thereof. Further preferred compositions comprise, for example, 40-99% of at least one of 70-100% of the SEQ ID NOs above, etc., or specified fragments, domains or variants thereof. Such composition percentages are by weight, volume, concentration, molarity, or molality as liquid or dry solutions, mixtures, suspension, emulsions, particles, powder, or colloids, as known in the art or as described herein.

Antibody Compositions Comprising Further Therapeutically Active Ingredients

The antibody compositions used in the method of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, 21$^{st}$ edition, Springhouse Corp., Springhouse, PA, 2001; Health Professional's Drug Guide 2001, ed., Shannon, Wilson, Stang, Prentice-Hall, Inc, Upper Saddle River, NJ; Pharmcotherapy Handbook, Wells et al., ed., Appleton & Lange, Stamford, CT, each entirely incorporated herein by reference).

By way of example of the drugs that can be combined with the antibodies for the method of the present invention, the anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The at least one cephalosporin can be at least one selected from cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef.

The at least one coricosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system.

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, 6-mercaptopurine, methotrexate, mizoribine, and tacrolimus.

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (See, e.g., pp. 1098-1136 of Nursing 2001 Drug Handbook.)

Anti-IL-12/IL-23p40 or IL-23 antibody compositions can further comprise at least one of any suitable and effective amount of a composition or pharmaceutical composition comprising at least one anti-IL-12/IL-23p40 or IL-23 antibody contacted or administered to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), an immunization, an immunoglobulin, an immunosuppressive (e.g., basiliximab, cyclosporine, daclizumab), a cytokine or a cytokine antagonist. Non-limiting examples of such cytokines include, but are not limited to, any of IL-1 to IL-23 et al. (e.g., IL-1, IL-2, etc.). Suitable dosages are well known in the art. See, e.g., Wells et al., eds., Pharmacotherapy Handbook, $2^{nd}$ Edition, Appleton and Lange, Stamford, CT (2000); PDR Pharmacopoeia, Tarascon Pocket Pharmacopoeia 2000, Deluxe Edition, Tarascon Publishing, Loma Linda, CA (2000), each of which references are entirely incorporated herein by reference.

Anti-IL-12/IL-23p40 or IL-23 antibody compounds, compositions or combinations used in the method of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences,* $18^{th}$ Edition, Mack Publishing Co. (Easton, PA) 1990. Pharmaceutically acceptable carriers can be routinely selected that are suitable for the mode of administration, solubility and/or stability of the anti-IL-23 antibody, fragment or variant composition as well known in the art or as described herein.

Pharmaceutical excipients and additives useful in the present composition include, but are not limited to, proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-12/IL-23p40 or IL-23 antibody compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, anti-IL-12/IL-23p40 or IL-23 antibody compositions can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-IL-12/IL-23p40 or IL-23 antibody, portion or variant compositions according to the invention are known in the art, e.g., as listed in "Remington: The Science & Practice of Pharmacy," $19^{th}$ ed., Williams & Williams, (1995), and in the "Physician's Desk Reference," $52^{nd}$ ed., Medical Economics, Montvale, NJ (1998), the disclosures of which are entirely incorporated herein by reference. Preferred carrier or excipient materials are carbohydrates (e.g., saccharides and alditols) and buffers (e.g., citrate) or polymeric agents. An exemplary carrier molecule is the mucopolysaccharide, hyaluronic acid, which may be useful for intraarticular delivery.

Formulations

As noted above, the invention provides for stable formulations, which preferably comprise a phosphate buffer with saline or a chosen salt, as well as preserved solutions and formulations containing a preservative as well as multi-use preserved formulations suitable for pharmaceutical or veterinary use, comprising at least one anti-IL-12/IL-23p40 or IL-23 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the method of the invention uses an article of manufacture, comprising packaging material and at least one vial comprising a solution of at least one anti-IL-12/IL-23p40 or IL-23 antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further uses an article of manufacture, comprising packaging material, a first vial comprising lyophilized anti-IL-12/IL-23p40 or IL-23 antibody, and a second vial comprising an aqueous diluent of prescribed buffer or preservative, wherein said packaging material comprises a label that instructs a patient to reconstitute the anti-IL-12/IL-23p40 or IL-23 antibody in the aqueous diluent to form a solution that can be held over a period of twenty-four hours or greater.

The anti-IL-12/IL-23p40 or IL-23 antibody used in accordance with the present invention can be produced by recombinant means, including from mammalian cell or transgenic preparations, or can be purified from other biological sources, as described herein or as known in the art.

The range of the anti-IL-12/IL-23p40 or IL-23 antibody includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an antimicrobial effect. Such concentrations are dependent on the preservative selected and are readily determined by the skilled artisan.

Other excipients, e.g., isotonicity agents, buffers, antioxidants, and preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol)

or non-ionic surfactants, such as polysorbate 20 or 80 or poloxamer 184 or 188, Pluronic® polyls, other block co-polymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations can be prepared by a process which comprises mixing at least one anti-IL-12/IL-23p40 or IL-23 antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-12/IL-23p40 or IL-23 specific antibody and preservative in an aqueous diluent is carried out using conventional dissolution and mixing procedures. To prepare a suitable formulation, for example, a measured amount of at least one anti-IL-12/IL-23p40 or IL-23 antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The formulations can be provided to patients as clear solutions or as dual vials comprising a vial of lyophilized anti-IL-12/IL-23p40 or IL-23 specific antibody that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present articles of manufacture are useful for administration over a period ranging from immediate to twenty-four hours or greater. Accordingly, the presently claimed articles of manufacture offer significant advantages to the patient. Formulations of the invention can optionally be safely stored at temperatures of from about 2° C. to about 40° C. and retain the biologically activity of the protein for extended periods of time, thus allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of anti-IL-12/IL-23p40 or IL-23 specific antibody can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-IL-12/IL-23p40 or IL-23 specific antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-IL-12/IL-23p40 or IL-23 specific antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising single vial systems include pen-injector devices for delivery of a solution, such as BD Pens, BD Autojector®, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, Smartject® e.g., as made or developed by Becton Dickensen (Franklin Lakes, NJ, www.bectondickenson.com), Disetronic (Burgdorf, Switzerland, www.disetronic.com; Bioject, Portland, Oregon (www.bioject.com); National Medical Products, Weston Medical (Peterborough, UK, www.weston-medical.com), Medi-Ject Corp (Minneapolis, MN, www.mediject.com), and similary suitable devices. Recognized devices comprising a dual vial system include those pen-injector systems for reconstituting a lyophilized drug in a cartridge for delivery of the reconstituted solution, such as the HumatroPen®. Examples of other devices suitable include pre-filled syringes, auto-injectors, needle free injectors, and needle free IV infusion sets.

The products may include packaging material. The packaging material provides, in addition to the information required by the regulatory agencies, the conditions under which the product can be used. The packaging material of the present invention provides instructions to the patient, as applicable, to reconstitute the at least one anti-IL-12/IL-23p40 or IL-23 antibody in the aqueous diluent to form a solution and to use the solution over a period of 2-24 hours or greater for the two vial, wet/dry, product. For the single vial, solution product, pre-filled syringe or auto-injector, the label indicates that such solution can be used over a period of 2-24 hours or greater. The products are useful for human pharmaceutical product use.

The formulations used in the method of the present invention can be prepared by a process that comprises mixing an anti-IL-12/IL-23p40 or IL-23 antibody and a selected buffer, preferably, a phosphate buffer containing saline or a chosen salt. Mixing the anti-IL-23 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The method of the invention provides pharmaceutical compositions comprising various formulations useful and acceptable for administration to a human or animal patient. Such pharmaceutical compositions are prepared using water at "standard state" as the diluent and routine methods well known to those of ordinary skill in the art. For example, buffering components such as histidine and histidine monohydrochloride hydrate, may be provided first followed by the addition of an appropriate, non-final volume of water diluent, sucrose and polysorbate 80 at "standard state." Isolated antibody may then be added. Last, the volume of the pharmaceutical composition is adjusted to the desired final volume under "standard state" conditions using water as the diluent. Those skilled in the art will recognize a number of other methods suitable for the preparation of the pharmaceutical compositions.

The pharmaceutical compositions may be aqueous solutions or suspensions comprising the indicated mass of each constituent per unit of water volume or having an indicated pH at "standard state." As used herein, the term "standard state" means a temperature of 25° C.+/−2° C. and a pressure of 1 atmosphere. The term "standard state" is not used in the art to refer to a single art recognized set of temperatures or pressure, but is instead a reference state that specifies temperatures and pressure to be used to describe a solution or suspension with a particular composition under the reference "standard state" conditions. This is because the volume of a solution is, in part, a function of temperature and pressure. Those skilled in the art will recognize that pharmaceutical compositions equivalent to those disclosed here can be produced at other temperatures and pressures. Whether such pharmaceutical compositions are equivalent to those disclosed here should be determined under the "standard state" conditions defined above (e.g. 25° C.+/−2° C. and a pressure of 1 atmosphere).

Importantly, such pharmaceutical compositions may contain component masses "about" a certain value (e.g. "about 0.53 mg L-histidine") per unit volume of the pharmaceutical composition or have pH values about a certain value. A component mass present in a pharmaceutical composition or pH value is "about" a given numerical value if the isolated antibody present in the pharmaceutical composition is able to bind a peptide chain while the isolated antibody is present in the pharmaceutical composition or after the isolated antibody has been removed from the pharmaceutical composition (e.g., by dilution). Stated differently, a value, such as a component mass value or pH value, is "about" a given numerical value when the binding activity of the isolated antibody is maintained and detectable after placing the isolated antibody in the pharmaceutical composition.

Competition binding analysis is performed to determine if the IL-12/IL-23p40 or IL-23 specific mAbs bind to similar or different epitopes and/or compete with each other. Abs are individually coated on ELISA plates. Competing mAbs are added, followed by the addition of biotinylated hrIL-12 or IL-23. For positive control, the same mAb for coating may be used as the competing mAb ("self-competition"). IL-12/IL-23p40 or IL-23 binding is detected using streptavidin. These results demonstrate whether the mAbs recognize similar or partially overlapping epitopes on IL-12/IL-23p40 or IL-23.

One aspect of the method of the invention administers to a patient a pharmaceutical composition comprising In one embodiment of the pharmaceutical compositions, the isolated antibody concentration is from about 77 to about 104 mg per ml of the pharmaceutical composition. In another embodiment of the pharmaceutical compositions the pH is from about 5.5 to about 6.5.

The stable or preserved formulations can be provided to patients as clear solutions or as dual vials comprising a vial of lyophilized at least one anti-IL-23 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stabilizing the anti-IL-23 antibody may result in other than a clear solution of lyophilized powder comprising the antibody. Among non-clear solutions are formulations comprising particulate suspensions, said particulates being a composition containing the anti-IL-23 antibody in a structure of variable dimension and known variously as a microsphere, microparticle, nanoparticle, nanosphere, or liposome. Such relatively homogenous, essentially spherical, particulate formulations containing an active agent can be formed by contacting an aqueous phase containing the active agent and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active agent and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymers selected from the group consisting of gleatin agar, starch, arabinogalactan, albumin, collagen, polyglycolic acid, polylactic aced, glycolide-L(−)lactide poly(episilon-caprolactone, poly(epsilon-caprolactone-CO-lactic acid), poly(epsilon-caprolactone-CO-glycolic acid), poly(β-hydroxy butyric acid), polyethylene oxide, polyethylene, poly (alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(−) lactide poly(episilon-caprolactone, poly(epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization, such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968. The antibody-based dry powder compositions may be produced by spray drying solutions or slurries of the antibody and, optionally, excipients, in a solvent under conditions to provide a respirable dry powder. Solvents may include polar compounds, such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO 9916419. The stabilized dispersions may be administered to the lung of a patient using a metered dose inhaler. Equipment useful in the commercial manufacture of spray dried medicaments are manufactured by Buchi Ltd. or Niro Corp.

An anti-IL-23 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating lupus, in a cell, tissue, organ, animal, or patient, as known in the art or as described herein, using at least one IL-23 antibody of the present invention, e.g., administering or contacting the cell, tissue, organ, animal, or patient with a therapeutic effective amount of IL-12/IL-23p40 or IL-23 specific antibody.

Any method of the present invention can comprise administering an effective amount of a composition or pharmaceutical composition comprising an anti-IL-23 antibody to a cell, tissue, organ, animal or patient in need of such modulation, treatment or therapy. Such a method can optionally further comprise co-administration or combination therapy for treating such diseases or disorders, wherein the administering of said at least one anti-IL-23 antibody, specified portion or variant thereof, further comprises administering, before concurrently, and/or after, at least one selected from at least one TNF antagonist (e.g., but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, etanercept (Enbrel™), adalimulab (Humira™), CDP-571, CDP-870, afelimomab, lenercept, and the like), an antirheumatic (e.g., methotrexate, auranofin, aurothioglucose, azathioprine, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, CT (2000); PDR Pharmacopoeia, Tarascon Pocket Pharmacopoeia 2000, Deluxe Edition, Tarascon Publishing, Loma Linda, CA (2000); Nursing 2001 Handbook of Drugs, $21^{st}$ edition, Springhouse Corp., Springhouse, PA, 2001; Health Professional's Drug Guide 2001, ed., Shannon, Wilson, Stang, Prentice-Hall, Inc, Upper Saddle River, NJ, each of which references are entirely incorporated herein by reference.

Therapeutic Treatments

Typically, treatment of lupus is affected by administering an effective amount or dosage of an anti-IL-12/23p40 or anti-IL-23 antibody composition that total, on average, a range from at least about 0.01 to 500 milligrams of an anti-IL-12/23p40 or anti-IL-23 antibody per kilogram of patient per dose, and, preferably, from at least about 0.1 to 100 milligrams antibody/kilogram of patient per single or multiple administration, depending upon the specific activity of the active agent contained in the composition. Alternatively, the effective serum concentration can comprise 0.1-5000 µg/ml serum concentration per single or multiple administrations. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and, preferably, 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or, alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or, alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.001 milligram to about 500 milligrams of active ingredient per unit or container. In these pharmaceutical compositions, the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes can be used according to the present invention for administering pharmaceutically effective amounts of an anti-IL-23 antibody. While pulmonary administration is used in the following description, other modes of administration can be used according to the present invention with suitable results. IL-12/IL-23p40 or IL-23 antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semi-synthtetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

Alternative Delivery

The invention further relates to the administration of an anti-IL-12/IL-23p40 or IL-23 antibody by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. An anti-IL-12/IL-23p40 or IL-23 antibody composition can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

Having generally described the invention, the same will be more readily understood by reference to the following Examples, which are provided by way of illustration and are not intended as limiting. Further details of the invention are illustrated by the following non-limiting Examples. The disclosures of all citations in the specification are expressly incorporated herein by reference.

EXAMPLES

A Multicenter, Randomized, Double-Blind, Placebo-Controlled, Proof-of-Concept Study of Ustekinumab in Subjects with Active Systemic Lupus Erythematosus

Synopsis

STELARA® (ustekinumab) is a fully human G1 kappa monoclonal antibody that binds with high affinity and specificity to the shared p40 subunit of human interleukin (IL)-12 and IL-23 cytokines. The binding of ustekinumab to the IL-12/23p40 subunit blocks the binding of IL-12 or IL-23 to the IL-12Rβ1 receptor on the surface of natural killer and $CD4^+$ T cells, inhibiting IL-12- and IL-23-specific intracellular signaling and subsequent activation and cytokine production. Abnormal regulation of IL-12 and IL-23 has been associated with multiple immune-mediated diseases including Systemic Lupus Erythematosus (SLE). Therefore, inhibition of IL-12 and IL-23 has the potential to be effective in the treatment of SLE.

Objective and Hypothesis

Primary Objective

The primary objective is to evaluate the efficacy of ustekinumab as measured by a reduction in disease activity for subjects with active SLE.

Secondary Objectives

The secondary objectives are to evaluate:
The safety and tolerability of ustekinumab in subjects with SLE.
The effect of ustekinumab administration on health-related quality of life in subjects with SLE.
The effects of ustekinumab on cutaneous manifestations of SLE.
Pharmacokinetics and immunogenicity of ustekinumab in subjects with SLE.

Exploratory Objective

The exploratory objectives are to evaluate:
Safety and efficacy during long-term administration of ustekinumab.
Reduction in corticosteroid dosing during long-term administration of ustekinumab.
Additional composite clinical endpoints or methods of calculation of clinical response with potential for greater sensitivity to improvement and/or worsening of SLE.
Biomarkers related to lupus disease (genetic, systemic, and skin-related).

Hypothesis

The hypothesis is that dosing with ustekinumab is significantly superior to placebo as measured by the Systemic Lupus Erythematosus Disease Activity Index 2000 (SLEDAI-2K) Responder Index (SRI-4) composite measure at Week 24.

Overview of Study Design

CNTO1275SLE2001 is a Phase 2a, proof-of-concept, multicenter, randomized, double-blind, placebo-controlled study of the efficacy and safety of ustekinumab added to standard of care background in subjects with active SLE. Subjects to be enrolled must have SLE according to Systemic Lupus International Collaborating Clinics (SLICC) criteria and Systemic Lupus Erythematosus Disease Activity Index 2000 (SLEDAI-2K) score ≥6, despite conventional treatment (e.g., immunomodulators, antimalarial drugs, corticosteroids, nonsteroidal anti-inflammatory drugs, anti-hypertensive drugs, and/or topical medications). In addition, subjects must have at least 1 positive autoantibody test (antinuclear antibodies [ANA], anti-double stranded deoxyribonucleic acid (anti-dsDNA) antibodies, and/or anti-Smith antibodies) observed during screening, as well as a well-documented positive autoantibody test in medical history. Subjects must also demonstrate at least 1 British Isles Lupus Assessment Group (BILAG) A and/or 2 BILAG B domain scores observed during screening. In addition, subjects must have a clinical SLEDAI-2K score ≥4 (excluding laboratory results) at week 0, prior to randomization.

Approximately 100 subjects will be randomly assigned in a 3:2 ratio to receive either ustekinumab or placebo through Week 24. Following randomization at Week 0, subjects will receive an initial body weight-range based IV dose approximating 6 mg/kg of ustekinumab (ustekinumab 260 mg [weight ≥35 kg to ≤55 kg]; ustekinumab 390 mg [weight >55 kg and ≤85 kg]; ustekinumab 520 mg [weight >85 kg]) followed by 90 mg SC administered every 8 weeks (q8w).

At Week 24, subjects receiving placebo will cross-over and all subjects will receive ustekinumab 90 mg SC at Weeks 24, 32, and 40 followed by safety follow-up through Week 56 in a blinded fashion for 16 weeks (i.e., approximately 5 half-lives) after last study agent SC administration.

A placebo comparator (added to standard of care background therapy) will be used through Week 24 for the evaluation of the efficacy and safety of ustekinumab in subjects with SLE. From Week 24 through Week 40, the placebo group will cross-over to receive ustekinumab 90 mg SC q8w. This cross-over design will permit placebo subjects to receive study agent and provide experience with ustekinumab 90 mg SC without the IV loading dose in subjects with SLE. The 40-Week dosing period will be useful to understand the longer-term safety and time course of potential clinical response of ustekinumab in the SLE population.

Every reasonable effort should be made to keep concomitant medications stable as defined in the protocol. All concomitant therapies must be recorded throughout the study beginning at entry into screening and any changes must be recorded throughout the study.

All subjects with cutaneous disease will be evaluated using Cutaneous Lupus Erythematosus Disease Area and Severity Index (CLASI) scoring. Additionally, subjects with cutaneous disease who consent to participate in the cutaneous lupus substudy will have other assessments including collection of skin biopsies (optional consent) and/or photographs of a cutaneous lesion or area of active disease (optional consent). There will not be any restrictions on the number of subjects with cutaneous disease who can enroll into either the main study or the cutaneous lupus substudy.

Interim analyses (IA) will be conducted when approximately ⅓ and ⅔ of subjects reach Week 24. In the first IA, only an assessment of notable efficacy will be performed. In the second IA, evidence for notable efficacy as well as treatment futility will be analyzed. Database locks (DBLs) will occur at Weeks 24 and following the last subject's Week 56 visit, or the final subject's Week 16 safety follow-up visit from the main study. In addition, an independent data monitoring committee (DMC) will review interim safety data periodically including a formal review when approximately ⅓ and ⅔ of subjects reach Week 24, as well as at the Week 24 DBL. The DMC will make a recommendation to the Sponsor committee whether the study should be stopped for futility or for safety concerns or if data meet prespecified criteria demonstrating notable efficacy. The content of the summaries, the DMC role and responsibilities, and the general procedures (including communications) will be defined in the DMC charter.

The amended study design will continue to provide open-label ustekinumab 90 mg q8w SC administration through Week 104. Subjects will be eligible to continue study treatment through Week 104 if they meet the study inclusion criteria (Section 4.1.3) including:

must not have permanently discontinued study treatment on or before their Week 40 visit, and are able to continue q8 week study treatment at approximately 8 weeks (±2 weeks) after their Week 40 visit or are able to resume study treatment with no more than 16 weeks (±2 weeks) since their Week 40 visit.

In addition to the DBL planned after the final subject's Week 56 visit, or after the last subject's Week 16 safety follow-up visit from the main study, there will be an additional DBL at the end of the study extension (following Study Extension 16-week safety follow-up visit).

Subject Population

Screening for eligible subjects must be performed no more than 6 weeks prior to the randomization visit (Week 0). The target study population is subjects with SLE according to SLICC criteria and SLEDAI-2K score ≥6, despite conventional treatment (e.g., immunomodulators, antimalarial drugs, corticosteroids, nonsteroidal anti-inflammatory drugs, anti-hypertensive drugs, and/or topical medications). In addition, subjects must have at least 1 positive autoantibody test (ANA, anti-dsDNA antibodies, and/or anti-Smith antibodies) observed during screening, as well as a well-documented positive autoantibody test in medical history. Subjects must also have at least 1 BILAG A and/or 2 BILAG B domain scores observed during screening prior to first administration of study agent.

In addition, to be eligible for study participation, subjects must have a clinical SLEDAI-2K score ≥4 (excluding laboratory results) for clinical features at Week 0 (prior to randomization) and have received approval for study randomization following review and adjudication of screening lupus assessments by the Sponsor and/or Sponsor-selected independent reviewer(s).

SLE subjects enrolling into the main study with active cutaneous lupus (including subjects with discoid lupus erythematosus, subacute cutaneous lupus erythematosus, alopecia or SLE malar rash or other SLE skin lesions characterized by erythema and or scale) will be evaluated using CLASI scoring. In addition, subjects who provide consent will be enrolled in the cutaneous lupus substudy evaluating the histology of cutaneous biopsies and/or skin photographs. Subjects participating in the cutaneous lupus substudy are not required to undergo biopsies, and may allow only photographs to document changes in an identified lesion or area of active disease.

Dosage and Administration

All subjects will receive a body weight range-based IV administration of study agent (placebo or ustekinumab) at Week 0 and then SC administration of placebo or ustekinumab at Weeks 8 and 16, followed by all subjects receiving ustekinumab dosing at Weeks 24, 32, and 40. Every reasonable effort should be made to keep concomitant medications stable at least through Week 28, with some adjustments allowed beyond Week 28 through the 8-Week Safety Follow-Up or study extension as defined in the protocol. A concomitant medication may be reduced or medication temporarily discontinued because of abnormal laboratory values, side effects, concurrent illness, or the performance of a surgical procedure, but the change and reason for the medication change should be clearly documented in the subject's medical record. If concomitant medications have been adjusted after randomization as allowed per protocol, every effort should be made to return subject back to the baseline (Week 0) dose level by the Week 12 visit; or increased medication use may render a subject to be considered a treatment failure.

Subjects who are enrolled in the study extension will continue to receive ustekinumab 90 mg SC administration every 8 weeks through Week 104. With the exception of corticosteroids, concomitant medications should be maintained at stable doses through the study extension.

Week 0 up to Week 24 (Blinded Study Agent Administration Phase)

Group 1: Subjects will receive weight-range based IV dosing of approximately 6 mg/kg of ustekinumab at Week 0 followed by ustekinumab 90 mg SC administrations at Weeks 8 and 16.

Group 2: Subjects will receive weight-range based IV dosing of placebo at Week 0 followed by placebo SC administrations at Weeks 8 and 16.

Week 24 to Week 40 (Cross-over Administration Phase)

Group 1: Subjects will receive an ustekinumab 90 mg SC administration at Week 24 followed by q8w administrations through Week 40.

Group 2: Subjects in the placebo dosing group will cross-over to ustekinumab 90 mg SC administrations at Week 24 followed by q8w administrations through Week 40.

After Week 40 to 16-Week Safety Follow-Up (Safety Follow-up Phase)

Groups 1 and 2: Subjects who do not participate in the study extension are expected to return for safety follow-up visits at Week 44 and for 8- and 16-weeks safety follow up.

Study Extension (Week 48/Week 56 Through Week 120)

Subjects who meet the study extension inclusion criteria (Section 4.1.3) will receive an additional 1 year of open label ustekinumab administration for the purpose of expanding the safety experience and maintenance of efficacy in lupus patients exposed to ustekinumab 90 mg q8w. Subjects who continue dosing in the extended study starting at Week 48 or at Week 56 will receive open-label ustekinumab SC dosing through Week 104. If the development of ustekinumab in SLE is terminated, then the study extension will also be discontinued.

Efficacy Evaluations

The primary efficacy endpoint of this study is to compare the proportion of subjects with a composite SRI-4 response at Week 24 for subjects receiving ustekinumab as compared to placebo treatment.

Efficacy evaluations and patient reported quality of life measures include:
SLEDAI-2K
S2K RI-50
BILAG
CLASI
Physician's Global Assessment of Disease Activity
Patient's Global Assessment of Disease Activity
Short-form 36 questionnaire
Fatigue Severity Scale
Patient's Assessment of Pain

Pharmacokinetic and Immunogenicity Evaluations

Serum samples will be used to evaluate the pharmacokinetics of ustekinumab, as well as the immunogenicity of ustekinumab (antibodies to ustekinumab).

Biomarker Evaluations and Serologic Markers

The collection, preparation, storage and shipment of skin biopsies, blood, serum and urine are detailed in the Laboratory Manual. Biomarkers may include, but are not limited to, inflammatory markers, ribonucleic acid (RNA), cell surface markers, autoantibodies, T cell and B cell repertoire, target specific markers, and other categories of biomarkers potentially involved in the development and the progression of lupus.

Serum Analyses

Serum will be analyzed for levels of specific proteins including but not limited to soluble CD40 ligand (sCD154), interleukin (IL)-6, IL-12p40, IL-17, IL-21, IL-22, IL-23p19, C-X-C motif chemokine 10 (CXCL10), B cell activating factor (BAFF), interferons, autoantibodies and other inflammation-related molecules.

Skin Biopsy Analyses

Skin biopsies will be utilized for cellular, molecular, and gene expression analyses.

Whole Blood Gene Expression Analyses

Whole blood will be collected from all subjects for RNA, flow cytometry, T cell and B cell repertoire and epigenetics analysis (e.g., deoxyribonucleic acid [DNA] methylation).

Serologic Markers

Autoantibodies (e.g., ANA, anti-dsDNA, etc.), complement C3 and C4 will be collected as described in the Table of Events (Table 1).

Pharmacogenomic (DNA) Evaluations

DNA samples will be used for research related to this study (CNTO1275SLE2001). Specific genomic testing will be undertaken for consenting subjects (subjects participating in this portion of the study must sign a separate informed consent form. The procedure will involve taking a blood sample that may be analyzed for specific target genes that may play a role in lupus. Any genomic assessments will be performed in strict adherence to current subject confidentiality standards for genetic testing. Refusal to participate in genomics testing will not result in ineligibility for participation in the rest of the clinical study.

Cutaneous Lupus Substudy

All subjects with cutaneous disease will be evaluated using CLASI scoring. Additionally, subjects with cutaneous disease who consent to participate in the cutaneous lupus substudy will have other assessments including collection of skin biopsies (optional consent) and/or photographs of an identified cutaneous lesion or area of active disease (optional consent). There will not be any restrictions on the number of subjects with cutaneous disease who can enroll into either the main study or the cutaneous lupus substudy.

Subjects who provide consent will be enrolled in the cutaneous lupus substudy evaluating the histology of cutaneous biopsies and/or skin photographs. Biopsy samples (2 samples, 4 mm size) from consenting subjects will be collected prior to dosing at Week 0 and at Week 24 from a single lesion or area of active cutaneous disease. Photographs and skin biopsies can target a different area of active disease, but the follow-up photographs or biopsies should re-evaluate the same area of active disease as originally assessed at week 0. Subjects participating in the cutaneous lupus substudy are not required to undergo biopsies, and may allow only photographs to document changes in an identified lesion or area of active disease. Subjects with cutaneous lupus deemed unsuitable for biopsy (e.g., malar rash or alopecia) can also be enrolled in the substudy, and may be evaluated by photography.

Independent of cutaneous biopsy collection, subjects who participate in the cutaneous lupus substudy will be requested to provide consent for photographs to be collected from an identified lesion or area of active disease. The photographs are for exploratory purposes only. The photographs will be used to assist in a qualitative evaluation of clinical response. Confidentiality of the subjects involved in this study will be maintained; specifically photographs of subjects in this study will not be published or otherwise made public without blocking adequate portions of the subject's face or body so that the individual cannot be identified.

Safety Evaluations

Safety assessments include vital signs, general physical exam and skin evaluations, adverse events (AE), serious AEs, concomitant medication review, pregnancy testing, infusion reactions, chemistry and hematology laboratory tests, and antibodies to ustekinumab. Chest x-ray and tuberculosis, human immunodeficiency virus, hepatitis B, and hepatitis C testing will be required at time of screening. Any clinically significant abnormalities persisting at the end of the study will be followed by the investigator until resolution or until a clinically stable endpoint is reached. Subject diary cards will be used to capture medication changes that occur in between study visits during the main portion of this study. Safety data collected up to 16 weeks after the final administration of study agent will be evaluated.

Statistical Methods

Sample Size Determination

Approximately 100 subjects will be randomly assigned in a 3:2 ratio to receive either ustekinumab or placebo through Week 24. Approximately sixty subjects treated with ustekinumab and approximately 40 subjects with placebo is projected to give approximately 80% power to detect a significant difference in response rate compared with placebo (assume 35% and 60% response rates in placebo and ustekinumab respectively, which translates to 25% absolute increase over placebo or an odds ratio of 2.79) with an alpha level of 0.1.

Efficacy Analyses

The primary endpoint of this study is the proportion of subjects with a composite measure of SLE disease activity (SLE Responder Index [SRI]-4 response) at Week 24. The primary analysis will be based upon the primary endpoint and will be conducted on the modified intent-to-treat (mITT) population, which includes all randomized subjects who receive at least 1 dose of study agent, have at least 1 measurement prior to the administration, and have at least 1 post-baseline SRI-4 measurement.

Last observation carried forward (LOCF) procedure will be used to impute the missing SRI-4 component if the subjects have data for at least 1 SRI-4 component at Week 24. If the subjects do not have data for any SRI components at Week 24, the subjects will be considered not to have achieved the SRI-4 response.

In addition, subjects who meet any of a variety of treatment failure criteria, such as receiving a dose of immunomodulator that is higher at Week 24 than at baseline, or initiated prohibited treatment (dose or timing) with corticosteroids, or discontinued study agent due to a lack of efficacy will be considered to have not achieved the primary endpoint, SRI-4 response at Week 24.

Logistic regression, adjusting for baseline stratifications and baseline SLEDAI, will be used to analyze the primary endpoint. The baseline SLEDAI value is defined as the closest non-missing measurement taken prior to the Week 0 infusion. If significant non-normality is observed, appropriate nonparametric tests will be used to evaluate the differences between treatments.

The study will be considered positive if the primary analysis achieves statistical significance at a significance level of 0.1 (2-sided) and ustekinumab shows a positive treatment effect relative to placebo treatment.

Safety Analyses

Safety will be assessed by analyses of the incidence and type of AEs, SAES, reasonably related AEs, infections, and infusion reactions. Safety assessments will also include analyses of laboratory parameters and change from baseline in laboratory parameters (hematology and chemistry) and incidence of abnormal laboratory parameters (hematology and chemistry).

TABLE 1

Time and Events Schedule for Main Study (Screening through 8-Week/16-Week Safety Follow-up)

| Week | Screening[a] | Blinded Study Agent Administration Phase | | | | | | | Cross-over Administration Phase | | | | 8-Week Safety Follow-up[k] | 16-Week Safety Follow-up/ Final Visit[b] |
|---|---|---|---|---|---|---|---|---|---|---|---|---|---|---|
| | | 0 | 4 | 8 | 12 | 16 | 20 | 24 | 28 | 32 | 36 | 40 | 44 | | |
| Study Procedures[c] | | | | | | | | | | | | | | | |
| Screening/Administrative | | | | | | | | | | | | | | | |
| Informed consent | X | | | | | | | | | | | | | | |
| Inclusion/exclusion criteria | X | X[a] | | | | | | | | | | | | | |
| Medical history and demographics | X | | | | | | | | | | | | | | |
| SLE classification by SLICC criteria | X | | | | | | | | | | | | | | |
| Study Drug Administration | | | | | | | | | | | | | | | |
| Randomization | | X | | | | | | | | | | | | | |
| Study agent administration | | X[d] | X | | X | | X | | X | X | | X | | | |
| Diary card | | | | | | | | | | | | | | | |
| Train on diary card and distribute | X | | | | | | | | | | | | | | |
| Collect, review and distribute diary cards | | X | X | X | X | X | X | X | X | X | X | X | X | X | X |
| Safety Assessments | | | | | | | | | | | | | | | |
| Physical examination | X | | | | | | | X | | | | | | | |
| HIV, HBV, and HCV | X | | | | | | | | | | | | | | |
| QuantiFERON ®-TB Gold test | X | | | | | | | | | | | | | | |
| Tuberculin skin test[e] | X | | | | | | | | | | | | | | |
| TB evaluation[f] | X | X | | X | | X | | X | | X | | X | | X | X |
| Serum pregnancy test[g] | X | | | | | | | | | | | | | | |
| Urine pregnancy test[g] | | X | | X | | X | | X | | X | | X | | X | X |
| Vital signs | X | X | X | X | X | X | X | X | X | X | X | X | X | X | X |
| Height | | X | | | | | | | | | | | | | |
| Weight | X | X | | | | | | X | | | | | | | |
| Chest x-ray[j] | X | | | | | | | | | | | | | | |
| Concomitant therapy | X | X | X | X | X | X | X | X | X | X | X | X | X | X | X |
| Adverse Events | X | X | X | X | X | X | X | X | X | X | X | X | X | X | X |
| Urinalysis (dipstick, all study subjects)[h] | X | X | X | X | X | X | X | X | X | X | X | X | X | X | X |
| Urine sample for biomakers (all subjects) | | X | X | X | | | X | X | X | | X | | X | X | |
| Protein/Creatinine ratio[s] | X | X | X | X | X | X | X | X | X | X | X | X | X | X | X |
| Microscopy of urine sediment[g] | X | X | X | X | X | X | X | X | X | X | X | X | X | X | X |

TABLE 1-continued

Time and Events Schedule for Main Study (Screening through 8-Week/16-Week Safety Follow-up)

| Week | Screening[a] | Blinded Study Agent Administration Phase | | | | | | Cross-over Administration Phase | | | | | 8-Week Safety Follow-up[b] | 16-Week Safety Follow-up/ Final visit[b] |
|---|---|---|---|---|---|---|---|---|---|---|---|---|---|---|
| | | 0 | 4 | 8 | 12 | 16 | 20 | 24 | 28 | 32 | 36 | 40 | 44 | |
| Pharmacokinetics/Immunogenicity | | | | | | | | | | | | | | |
| Serum ustekinumab concentrations[s,t] | | 2X[v] | X | X | X | X | | X | X | X | | X | | X | X |
| Antibodies to study agent[s,t] | | X | | X | X | X | | X | | | | X | | | X |
| Pharmacogenomics (DNA)[u] | | | | | | | | | | | | | | | |
| Whole blood DNA | | X | | | | | | | | | | | | | |
| Biomarkers | | | | | | | | | | | | | | | |
| Serum sample | X | X | X | X | X | | | X | X | X | | X | | X | X |
| Whole blood for RNA gene expression | X | X | X | | X | | | X | X | | | X | | X | X |
| T cell and B cell repertoire | | X | | | X | | | X | | | | | | X | |
| Epigenetics | | X | | | X | | | X | | | | | | X | |
| Flow cytometry[v] | | X | | | X | | | X | | | | | | X | |

[a]Screening visit must be performed no more than 6 weeks prior to randomization visit (Week 0). To be eligible for study participation, subjects must have SLEDAI score ≥ 4 (excluding laboratory results) for clinical feature at Week 0 and have received approval for study randomization following review and adjudication of screening lupus assessments by the Sponsor and/or Sponsor-selected independent reviewer(s).
[b]Subjects, who discontinue study agent administrations on or before the Week 40 visit, must return approximately 8 and 16 weeks after last study agent achninistration for safety follow-up visits. The 8-Week and/or 16-week safety follow-up visit are not required for subjects who continue treatment in the study extensim within 8 (±2 weeks) or 16 (±2 weeks) weeks, respectively, of their Week 40 visit (refer to Table 2).
[c]All assessments (except for injection-site evaluation) are to be completed prior to study agent admtration, unless otherwise specified.
[d]Intravenous administration of study agent at Week 0, all other doses will be SC.
[e]Only required if QuantiFERON ®-TB is not registered/approved locally or the tuberculin skin test (TST) is mandated by local health authorities.
[f]If TB is suspected at any time during the study, a chest x-ray (local), and QuantiFERON ®-TB Gold test should be performed. A TST is additionally required if the QuantiFERON ®-TB Gold test is not registered/approved locally or the TST is mandated by local health authorities.
[g]In addition to the Screening evaluation, the pregnancy test may be repeated at any time at the discretion of investigator or subject
[h]May conduct urine pregnancy test more frequently (eg. monthly basis) if required by local regulations.
[i]Posterior/anterior and lateral views must be taken within 3 months prior to the first administration of study agent for TB detection.
[j]Subjects should be monitored for the occurrence of infusion or injection-site reactions for 30 Minutes after the infusion (IV administration) or injection.
[k]Only for subjects who consented to participate in the cutaneous lupus substudy for biopay and/or photograph collection.
[l]All visit-specific patient reported outcome assessments should be conducted before any tests, procedures, or other consultations for that visit to prevent influencing subjects' perceptions.
[m]Complete SLEDAI-2K (Baseline) will be evaluated during screening and at Week 0, although at Week 0 only the clinical (non-laboratory) features will be considered to confirm eligibility for study enrollment. The photographs and skin biopsies can target a different location of active disease but the follow-up photographs or biopsies should re-evaluate the same area of active disease as originally assessed at week 0.
[n]CLASI scoring will be obtained for all enrolled subjects with cutaneous lupus regardless of enrollment in the cutaneous lupus regardless of enrollment in the cutaneous lupus substudy.
[o]Also perform B cell analyses at screening for subjects previously exposed to B cell depleting therapies.
[p]If abnormal test result is not obtained at screening or at Week 0, no additional follow-up testing is required. However, additional testing may be performed if needed.
[q]These tests will be performed on-site or at local lab(s).
[r]Anti-dsDNA should be analyzed at every specified visit. If the other autoantibody tests are negative at both screening and Week 0 visits, then those autoantibody tests need only be analyzed again at Weeks 24 and 48. However, if the other auto antibodies tests are positive at either screening or Week 0, then they should be analyzed at all visits.
[s]The same blood draw will be used for the measurement of ustekinumab concentration and detection of antibodies to ustekinumab. For visits with study agent administration, all blood samples for assessing pre-dose ustekinumab concentration and antibodies to ustekinumab MUST be collected BEFORE the administration of the study agent.
[t]At week 0 visit, 2 separate samples for serum ustekinumab concentrations (indicated by "2X" in the Schedule above) will be collected (1 sample will be collected prior to IV infusion and the other collected 1 hour after the end of the infusion) for all subjects.
[u]Only for the subjects who consent to allow genomic analyses.
[v]Flow cytometry samples will be analyzed from subjects at selected sites.
[w]Biopsies are allowed to occur 1-2 days prior to randomization and at the Week 24 visit
[x]Photographs do no need to be taken at the same area of active disease as the biopsy; however, follow-up photographs or biopsies should re-evaluated the same area of active disease as originally assessed at week 0.

TABLE 2

Time and Events Schedule in Study Extension (Week 48/56 through Extension Safety Follow-up)

| Week | Study Extension | | | | | | | | Extension Safety Follow-up[a] | |
|---|---|---|---|---|---|---|---|---|---|---|
| | | | | | | | | | Extension 8-Week Safety Follow-up | Extension 16-Week Safety Follow-up/ Final Visit |
| | Wk 48 | Wk 56 | Wk 64 | Wk 72 | Wk 80 | Wk 88 | Wk 96 | Wk 104 | | |
| Study Procedures[b] | | | | | | | | | | |
| Screening/Administrative | | | | | | | | | | |
| Informed consent[c] | X | X | | | | | | | | |

TABLE 2-continued

Time and Events Schedule in Study Extension (Week 48/56 through Extension Safety Follow-up)

| Week | Study Extension | | | | | | | | Extension Safety Follow-up[a] | |
|---|---|---|---|---|---|---|---|---|---|---|
| | Wk 48 | Wk 56 | Wk 64 | Wk 72 | Wk 80 | Wk 88 | Wk 96 | Wk 104 | Extension 8-Week Safety Follow-up | Extension 16-Week Safety Follow-up/ Final Visit |
| Study Drug Administration | | | | | | | | | | |
| Study agent administration | X[c] | X[c] | X | X | X | X | X | X | | |
| Safety Assessments | | | | | | | | | | |
| Physical examination | X | | X | | X | | | X | X | X |
| TB evaluation[d] | X | X | X | X | X | X | X | X | X | X |
| Urine pregnancy test[e] | X | X | X | X | X | X | X | X | X | X |
| Vital signs | X | X | X | X | X | X | X | X | X | X |
| Concomitant therapy | X | X | X | X | X | X | X | X | X | X |
| Adverse Events | X | X | X | X | X | X | X | X | X | X |
| Injection-site reaction evaluation[f] | X | X | X | X | X | X | X | X | | |
| Efficacy Assessments[g] | | | | | | | | | | |
| S2K RI-50 | X | | X | | X | | X | | X | |
| CLASI[h] | X | | X | | X | | X | | X | |
| BILAG | X | | X | | X | | X | | X | |
| Physician's Global Assement of Disease Activity | X | | X | | X | | X | | X | |
| Patient's Global Assessments (Pain and Disease Activity) | X | | X | | X | | X | | X | |
| SF-36 | X | | X | | | | X | | X | |
| Fatigue Severity Scale | X | | X | | | | X | | X | |
| Clinical Laboratory Assessments | | | | | | | | | | |
| Hematology[i] | X | X | X | X | X | X | X | X | X | X |
| C3, C4 | X | X | X | X | X | X | X | X | X | X |
| Coombs direct test[k] (as needed) | X | | | X | | | | X | X | X |
| Coagulation Labs (as needed)[i,j] | X | | | X | | | | X | X | X |
| Chemistry[k] | X | X | X | X | X | X | X | X | X | X |
| Anti-dsDNA | X | X | X | X | X | X | X | X | X | X |
| Other autoantibodies[l] | X | | | X[l] | | | | X | | |
| Anti-phospholipid antibodies[j] | X | | | X | | | | X | | |
| Ig isotype profile | X | | | | | | | X | | |
| Urine Analyses (spot urine)[i] | | | | | | | | | | |
| Urinalysis (dipstick, all study subjects)[k] | X | X | X | X | X | X | X | X | X | X |
| Urine sample for biomarkers (all subjects) | X | | | X | | | | X | X | X |
| Protein/Creatinine ratio[j] | X | X | X | X | X | X | X | X | X | X |
| Microscopy of urine sediment[k,m] | X | X | X | X | X | X | X | X | X | X |
| Pharmacokinetics/Immunogenicity | | | | | | | | | | |
| Serum ustekinumab concentrations[n] | X | | | X | | | | X | X | X |
| Antibodies to study agent[n] | X | | | X | | | | X | X | X |

TABLE 2-continued

Time and Events Schedule in Study Extension (Week 48/56 through Extension Safety Follow-up)

| | Study Extension | | | | | | | | Extension Safety Follow-up[a] | |
|---|---|---|---|---|---|---|---|---|---|---|
| | | | | | | | | | Extension 8-Week | Extension 16-Week Safety |
| Week | Wk 48 | Wk 56 | Wk 64 | Wk 72 | Wk 80 | Wk 88 | Wk 96 | Wk 104 | Safety Follow-up | Follow-up/ Final Visit |
| Biomarkers | | | | | | | | | | |
| Serum sample | X | | | X | | | X | | X | X |
| Whole blood for RNA gene expression | X | | | X | | | X | | X | X |

[a]Subjects, who complete all scheduled doses or discontinue study agent administration before the end of the study extension, must return at approximately 8 and 16 weeks after last study agent administration for safety follow-up visits.
[b]All assessements (except for injection-site evaluation) are to be completed prior to study agent administration.
[c]Prior to dosing in the study extension, subjects must sign a revised ICF indicating agreement to participate in the extended study.
[d]TB evaluation includes an assessment of recent exposure risk of TB including new or chronic cough, fever, night sweats, unintentional weight loss or recent contact with someone with active TB. If TB is suspected at any time during the study, a chest x-ray (local), and QuantiFERON®-TB Gold test should be performed. A TST is additionally required if the QuantiFERON®-TB Gold test is not registered/approved locally or the TST is mandated by local health authorities.
[e]In addition to scheduled urine dipstick testing, a serum or urine pregnancy test may be conducted at any time at the discretion of investigator or subject, or if required by local regulations.
[f]Subjects should be monitored for the occurence of injection-site reaction for 30 minutes after the injection.
[g]All visit-specific patient reported outcome assessment should be conducted before any tests, procedures, or other consultations for that visit to prevent influencing subjects' perception.
[h]CLASI scoring will be obtained for all enrolled subjects who have cutaneous lupus.
[i]If clinical concerns or abnormal results from prior visit observed in these assessments, then strong consideration should be given to more frequent testing (at least q4 week assessments) until normalized.
[j]If history of abnormal test result was observed in main study, then follow scheduled assessments. Additional testing my be performed if needed.
[k]These tests will be performed on-site or local lab(s).
[l]if the "other autoantibody" tests were routinely negative prior to Week 48, then those autoantibody tests need only be analyzed annually. However, if the other autoantibodies tests were positive at either screening or Week 0, then they should be analyzed every 6 months as shown.
[m]Urine sediment analyses to be performed at study site or local lab if possible. If necessary, with agreement from study sponsor, urine sediment analyses can be conducted at the Central Lab for specific sites that cannot arrange local analyses.
[n]The same blood draw will be used for the measurement of ustekinumab concentration and antibodies to ustekinumab MUST be collected BEFORE the administration of the study agent.

ABBREVIATIONS

ACE angiotensin-converting enzyme
AE adverse event
ANA antinuclear antibodies
ANCOVA analysis of covariance
anti-dsDNA anti-double stranded deoxyribonucleic acid
anti-HBc total HBV core antibody total
anti HBs HBV surface antibody
ARB angiotensin II receptor blocker
AZA/6 MP azathioprine/6 mercaptopurine
BAFF B cell activating factor, also known as B lymphocyte stimulator (BLyS)
BCG Bacille Calmette-Guérin
β-hCG β human chorionic gonadotropin
BICLA BILAG-based Combined Lupus Assessment
BILAG British Isles Lupus Assessment Group
BLyS B lymphocyte stimulator, also known as B cell activating factor (BAFF)
CLASI Cutaneous Lupus Erythematosus Disease Area and Severity Index
CLE cutaneous lupus erythematosus
CNS central nervous system
COX-2 cyclooxygenase-2
CD Crohn's disease
CTCAE Common Terminology Criteria for Adverse Events
CXCL10 C-X-C motif chemokine 10
DMC data monitoring committee
DNA deoxyribonucleic acid
eDC Electronic Data Capture
EDTA ethylenediaminetetraacetic acid
ELISA enzyme-linked immunosorbent assay
FSS Fatigue Severity Scale
FVP Final Vialed Product
GCP Good Clinical Practice
HBsAg HBV surface antigen
HBV hepatitis B virus
HCV hepatitis C virus
HIV human immunodeficiency virus
IA interim analyses
ICF informed consent form
ICH International Conference on Harmonisation
IEC Independent Ethics Committee
Ig Immunoglobulin
IL Interleukin
IM Intramuscular
IP Investigative Product
IRB Institutional Review Board
IV Intravenous
IWRS interactive web response system
JAK j anus kinase
mITT modified intent to-treat
MMF mycophenolate mofetil
MPA mycophenolic acid
MTX Methotrexate
NAbs neutralizing antibodies
NSAIDs nonsteroidal anti inflammatory drugs
PFS prefilled syringe
PGA Physician's Global Assessment of Disease Activity
PK Pharmacokinetic
PQC product quality complaint
PROs patient reported outcomes
PsA psoriatic arthritis
PtGA Patient's Global Assessment of Disease Activity
q8w every 8 weeks RA rheumatoid arthritis
RNA ribonucleic acid
RNP Ribonucleoprotein
S2K RI-50 SLEDAI-2K Responder Index
SAE serious AE
SAP statistical analysis plan
SC Subcutaneous
SF Short-form
SLE Systemic Lupus Erythematosus
SLEDAI Systemic Lupus Erythematosus Disease Activity Index
SLEDAI-2K Systemic Lupus Erythematosus Disease Activity Index 2000
SLICC Systemic Lupus International Collaborating Clinics
SRI-4 SLE Responder Index
SSA anti-Sjögren's-syndrome-related antigen A
SSB anti-Sjögren's-syndrome-related antigen B
TB Tuberculosis
Th T helper
TNFα tumor necrosis factor alpha
ULN upper limit of normal
VAS visual analogue scale
WBC white blood cells

1. Introduction

STELARA® (ustekinumab) is a fully human G1 kappa monoclonal antibody that binds with high affinity and specificity to the shared p40 subunit of human interleukin (IL)-12 and IL-23 cytokines. The binding of ustekinumab to the IL-12/23p40 subunit blocks the binding of IL-12 or IL-23 to the IL-12Rβ1 receptor on the surface of natural killer and CD4+ T cells, inhibiting IL-12- and IL-23-specific intracellular signaling and subsequent activation and cytokine production. Abnormal regulation of IL-12 and IL-23 has been associated with multiple immune-mediated diseases including systemic lupus erythematosus (SLE). Therefore, inhibition of IL-12 and IL-23 has the potential to be effective in the treatment of SLE.

Systemic lupus erythematosus is a complex, chronic heterogeneous autoimmune disease of unknown etiology that can affect almost any organ system, and which follows a waxing and waning disease course. Systemic lupus erythematosus occurs much more often in women than in men, up to 9 times more frequently in some studies, and often appears during the child-bearing years between ages 15 and 45. This disease is more prevalent in Afro-Caribbean, Asian, and Hispanic populations. In SLE, the immune system attacks the body's cells and tissue, resulting in inflammation and tissue damage which can harm the heart, joints, skin, lungs, blood vessels, liver, kidneys and nervous system. About half of the subjects diagnosed with SLE present with organ-threatening disease, but it can take several years to diagnose subjects who do not present with organ involvement. Some of the primary complaints of newly diagnosed lupus patients are arthralgia (62%) and cutaneous symptoms (new photosensitivity; 20%), followed by persistent fever and malaise.[39] The estimated annual incidence of lupus varies from 1.8 to 7.6 cases per 100,000 and the worldwide prevalence ranges from 14 to 172 cases per 100,000 people.[39] Patients with mild disease have mostly skin rashes and joint pain and require less aggressive therapy; regimens include nonsteroidal anti-inflammatory drugs (NSAIDs), anti-malarials (e.g., hydroxychloroquine, chloroquine, or quinacrine) and/or low dose corticosteroids. With more severe disease patients may experience a variety of serious conditions depending on the organ systems involved, including lupus nephritis with potential renal failure, endocarditis or myocarditis, pneumonitis, pregnancy complications, stroke, neurological complications, vasculitis and cytopenias with associated risks of bleeding or infection. Common treatments for more severe disease include immunomodulatory agents, such as methotrexate (MTX), azathioprine, cyclophosphamide, cyclosporine, high dose corticosteroids, biologic B cell cytotoxic agents or B cell modulators, and other immunomodulators. Patients with serious SLE have a shortening of life expectancy by 10 to 30 years, largely due to the complications of the disease, of standard of care therapy, and/or accelerated atherosclerosis. In addition, SLE has a substantial impact on quality of life, work productivity, and healthcare expenditures. Existing therapies for SLE are generally either cytotoxic or immunomodulatory, and may have notable safety risks. Newer treatments for SLE have provided only modest benefits over standard of care therapy. Thus, there is a large unmet need for new alternative treatments that can provide significant benefit in this disease without incurring a high safety risk.

The long-term outcome for patients with lupus depends on a variety of factors including whether they have organ involvement, the presence of certain laboratory measures (such as anti-phospholipid antibodies), race, gender, age of consent, access to health care, adherence to treatment, education and other comorbidities. Only about 5% of patients who are diagnosed with SLE will demonstrate a spontaneous remission without treatment. A variety of new therapeutic agents are being evaluated for the treatment of subjects with refractory lupus, however to date very few have demonstrated notable clinical efficacy beyond those medications currently considered standard of care for patients with this disease.

In this study, the target population is subjects with SLE according to Systemic Lupus International Collaborating Clinics (SLICC) criteria and Systemic Lupus Erythematosus Disease Activity Index (SLEDAI)[11] score ≥6, despite conventional treatment (e.g., immunomodulators, antimalarial drugs, corticosteroids, NSAIDs, anti-hypertensive drugs, and/or topical medications). In addition, subjects must have at least 1 positive autoantibody test (antinuclear antibodies [ANA], anti-double stranded deoxyribonucleic acid [anti-dsDNA] antibodies, and/or anti-Smith antibodies) observed during screening, as well as a well-documented positive autoantibody test in medical history. Subjects must also demonstrate at least 1 British Isles Lupus Assessment Group (BILAG)[38] A and/or 2 BILAG B domain scores during screening. In addition, subjects must have a SLEDAI score ≥4 at Week 0 (prior to randomization) for clinical features (excluding laboratory results). This level of disease activity is consistent with prior studies that have investigated an experimental therapy for systemic lupus.[36]

1.1. Background

To date, ustekinumab has received marketing approval globally, including countries in North America, Europe, South America, and the Asia-Pacific region, for the treatment of adult patients including those with chronic moderate to severe plaque psoriasis and/or active psoriatic arthritis. Ustekinumab is also being evaluated in a Phase 3 studies for Crohn's disease (CD).

1.2. Overall Rationale for the Study

1.2.1. Scientific Rationale for Use of Anti-IL-12/23p40 Therapy in Systemic Lupus Erythematosus Systemic lupus erythematosus is a complex, immune-mediated inflammatory disorder exhibiting dysregulated B lymphocytes that produce destructive autoantibodies. B cell targeted therapies (e.g., belimumab) for SLE, however, have shown only modest clinical results beyond a limited standard of care control,[22] suggesting that additional immune pathways play an important role in SLE pathogenesis. Chronic immune activation in SLE leads to the increased production of inflammatory cytokines that contribute actively to local inflammation and to processes that mediate tissue damage. Many SLE patients, for example, have a characteristic type I interferon signature observed in their blood cells.[2] Interferon signatures have also been observed to occur more frequently in lupus families and may be a risk factor for development of SLE.[23] Several studies have also reported an elevation of IL-12, IL-6, and IL-23 in both serum and tissues of patients,[4,20,24,26,30,44] suggesting that the inflammatory environment in SLE is prone to induce T helper (Th)1 and Th17 cells. Increased levels of IL-17 in the serum have been observed in SLE patients,[3,31,36,44,45,46] but the correlation of IL-17 levels to disease activity is not strong.[37,46] No direct genetic links have been established in SLE to the IL-12/IL-23/Th17 pathway,[18,28,29] although genome-wide association studies in SLE have identified STAT4, which mediates IL-12 signaling, as a susceptibility gene in both the Caucasian and Asian populations.[12,16] In patients with active SLE, messenger RNA levels of p19, p40, and p35 were significantly higher compared with those in the inactive SLE patients.[14] Targeting IL-12/23p40 with ustekinumab has been shown in 3 separate case reports to be associated with a marked improvement of cutaneous lupus.[5,6,43] Taken together, there is accumulating evidence to demonstrate the importance of the IL-12 and IL-23 cytokine pathways in SLE pathogenesis, warranting further clinical investigation of ustekinumab as an interventional therapy in this disease.

In addition, 2 disease-related groups, the Alliance for Lupus Research and Lupus Research Institute, independently commissioned a scientific review of a large set of commercially available lupus drug candidates, from which ustekinumab was recommended to be evaluated in SLE based on its molecular mechanism, which further supports the scientific rationale for a placebo-controlled clinical study to evaluate the efficacy and safety of ustekinumab in subjects with active SLE.

1.1.2.1. Subgroup of Subjects with Active Cutaneous Manifestations of Systemic Lupus Erythematosus The above-mentioned case reports of patients with refractory cutaneous lupus responding to ustekinumab treatment prompts an evaluation of the effects of ustekinumab on cutaneous lesions. Given the relatively common occurrence of cutaneous manifestations in SLE, the feasibility of repeated punch biopsy and/or photographs of an identified lesion or area of active disease, and the availability of cutaneous lupus erythematosus (CLE)-specific disease assessment tools, this patient population may provide useful data regarding the effects of ustekinumab on SLE and the symptoms of cutaneous disease. All subjects with cutaneous disease will be evaluated using CLASI scoring. Additionally, subjects with cutaneous disease who consent to participate in the cutaneous lupus substudy will be requested to provide potential collection of skin biopsies (optional consent) and/or photographs of an identified lesion or area of active disease (optional consent). There are no pre-specified numbers of subjects to be enrolled with cutaneous disease for either the main study or the cutaneous lupus substudy.

1.3. Justification for Dosing Regimen

The dosing regimen for this study was selected based on experience with the use of ustekinumab in the treatment of subjects with moderately to severely active CD (C0743T26, CNTO1275CRD3001, and CNTO1275CRD3002). Both CD and SLE are immune-mediated inflammatory diseases, which are commonly treated with immunomodulators, such as methotrexate (MTX), azathioprine and corticosteroids, and thus this indication serves as a useful model for risk assessment of ustekinumab in lupus. Although the dosing rationale has not changed, additional safety and efficacy information has become available from the ustekinumab Phase 3 CD (UNITI) studies which supports amending the protocol to further extend treatment with ustekinumab 90 mg SC q8w for an additional year. These results from the UNITI CD studies are summarized later in this section.

Although the dosing rationale has not changed, some additional safety and efficacy information has become available from the ustekinumab Phase 3 CD (UNITI) studies which supports the treatment extension planned for this study. These results from the UNITI CD studies are summarized later in this section (Section 1.3).

In the Phase 2b dose ranging study C0743T26, a single IV ustekinumab dose of 6 mg/kg was the highest loading dose tested in subjects with CD. In this study, the 6 mg/kg IV dose was shown to be effective in inducing clinical response through Week 8 and was well tolerated with a safety profile generally comparable to the other treatment groups. Results from ustekinumab CD studies also suggest that an IV loading dose may provide a rapid onset of clinical response following IL-12 and IL-23 inhibition. In the Phase 3 studies CNTO1275CRD3001 and CNTO1275CRD3002, body weight-range dosing approach (ustekinumab 260 mg [weight ≤55 kg]; ustekinumab 390 mg [weight >55 kg and ≤85 kg]; ustekinumab 520 mg [weight >85 kg]) was used to approximate the IV loading dose of 6 mg/kg. The body weight-range based dosing allows administration of complete vials to patients to simplify dose calculation and reduce the potential for errors in dosing. This weight range dosing is intended to achieve drug exposure similar to that observed with 6 mg/kg weight-adjusted dosing. Thus, in this study, a strategy of IV loading dose based on body weight range at Week 0 will be evaluated to assess the ability of the drug to rapidly reduce the disease activity of SLE without causing significant concern for increased safety risk based on data obtained from previous studies.

The ustekinumab maintenance dosing regimen of 90 mg SC every 8 weeks (q8w) was studied in subjects with CD (C0743T26). The results from C0743T26 study suggest that ustekinumab 90 mg SC q8w was safe and effective in maintaining subjects in clinical remission. The q8w dosing frequency is selected to maintain sufficient ustekinumab exposure to determine if treatment with ustekinumab can provide sustained clinical response. In addition, SC administration is considered more convenient compared with IV administration. A 16-week follow-up period following last ustekinumab study dose was selected to allow more than 5 half-lives for drug elimination and adequate safety follow-up.

In addition, there were also 3 Phase 3 studies in subjects with CD initiated in 2011 that have recently provided additional safety and efficacy data; UNITI-1, UNITI 2, and IM-UNITI. UNITI-1 and UNITI-2 were 8-week induction studies and were identical in design but studied distinct patient populations. UNITI-1 studied subjects who had failed or were intolerant to anti-TNF agents while UNITI-2 studied subjects who had not failed a TNF antagonist but who had failed conventional immunomodulator or steroid therapies. The IM-UNITI study evaluated maintenance treatment for patients enrolled from both UNITI-1 and UNITI-2 studies. The UNITI studies randomized 1,367 subjects to either placebo, 130 mg IV or approximately 6 mg/kg IV. After Week 8 of therapy, subjects in both UNITI-1 and UNITI-2 studies could enter into IM-UNITI, which primarily evaluated two maintenance regimens of 90 mg every 8 or 12 weeks compared to placebo in induction responders. While the IM-UNITI study is still ongoing in long-term extension phase, the primary results of all 3 studies have been published,[7] and the results supported the approval of ustekinumab in patients with active moderate to severe CD. The approved dose in induction is a single IV weight-based dose approximating 6 mg/kg and the approved maintenance dose is 90 mg either every 8 or 12 weeks depending on the approval region. The results of these studies are particularly relevant to the CNTO1275SLE2001 SLE study in that a similar dose is being evaluated. In addition, similar to the SLE population, about ⅓ of the CD patients enrolled into the UNITI studies were using concomitant immunomodulators (e.g MTX, AZA, 6-MP) and approximately 46% were on concomitant glucocorticoids. The results of these studies are reviewed in detail. in the primary publication[7] and the highlights are presented below:

- In the 2 UNITI induction studies, the primary endpoint and all major secondary endpoints were met for both doses studied including the 6 mg/kg dose.
- In the IM-UNITI maintenance study, both the 90 mg every 8 or every 12 week regimens were superior to placebo in maintaining response or achieving remission compared to placebo at Week 44.
- Importantly, the safety profiles of both maintenance doses were comparable to placebo over 44 weeks and no new safety signals were identified. The safety profile was similar to that seen in the psoriatic indications.

In summary, these CD studies support the dosing regimen planned for this proof-of concept SLE study including body weight-range based IV loading dose approximating 6 mg/kg followed by 90 mg SC q8w to ensure a high level of systemic exposure of ustekinumab to inhibit the actions of IL-12/23.

Open label 90 mg SC q8w ustekinumab dosing will be provided to subjects starting at Week 24 though Week 40. Per the amended study design, subjects who are able to continue q8w study treatment at approximately 8 weeks (±2 weeks) after their Week 40 visit, or are able to resume study treatment with no more than 16 weeks (±2 weeks) since their Week 40 visit will be eligible for continued 90 mg SC q8w ustekinumab treatment through Week 104, followed by an additional 16-week safety follow-up period.

2. Objectives and Hypothesis 2.1. Objectives

Primary Objective

The primary objective is to evaluate the efficacy of ustekinumab as measured by a reduction in disease activity for subjects with active SLE.

Secondary Objectives

The secondary objectives are to evaluate:
The safety and tolerability of ustekinumab in subjects with SLE.
The effect of ustekinumab administration on health-related quality of life in subjects with SLE.
The effects of ustekinumab on cutaneous manifestations of SLE.
Pharmacokinetics and immunogenicity of ustekinumab in subjects with SLE.

Exploratory Objectives

The exploratory objectives are to evaluate:
Safety and efficacy during long-term administration of ustekinumab.
Reduction in corticosteroid dosing during long-term administration of ustekinumab.
Additional composite clinical endpoints or methods for calculation of response with potential for greater sensitivity to improvement and/or worsening of SLE.
Biomarkers related to lupus disease (genetic, systemic, and skin-related).

2.2. Hypothesis

The hypothesis is that ustekinumab is significantly superior to placebo as measured by the Systemic Lupus Erythematosus Disease Activity Index 2000 (SLEDAI-2K) Responder Index (SRI-4) composite measure at Week 24.

3. Study Design and Rationale

A complete list describing all efficacy evaluations and endpoints, and which evaluations are included in the composite endpoints is provided in Appendix 1. The main study is defined from the original protocol as screening through the Main Study 8-week and 16-week safety follow-up visits. Note that the Main Study 8-week and 16-week safety follow-up visits were previously described in the original protocol as the Week 48 and Week 56 visits. However, with this amendment, the Week 48 and Week 56 visits will only be used to describe treatment visits for those subjects who are participating in the study extension. The study extension (applicable to subjects meeting the inclusion criteria) is defined as the Week 48 or Week 56 visits through the Study Extension 16-week safety follow-up visit.

3.1. Overview of Study Design

CNTO1275SLE2001 is a Phase 2a, proof-of-concept, multicenter, randomized, double-blind, placebo-controlled study of the efficacy and safety of ustekinumab added to standard of care background therapy in subjects with active SLE. Subjects between 18 and 75 years of age must have SLE according to SLICC criteria and SLEDAI-2K score ≥6, despite conventional treatment (e.g., immunomodulators, antimalarial drugs, corticosteroids, NSAIDs, anti-hypertensive drugs, and/or topical medications). In addition, subjects must have at least 1 positive autoantibody test (ANA, anti-dsDNA antibodies, and/or anti-Smith antibodies) observed during screening, as well as a well-documented positive autoantibody test in their medical history. Subjects must also demonstrate at least 1 BILAG A and/or 2 BILAG B domain scores observed during screening. In addition, subjects must have a clinical SLEDAI-2K score >4 (excluding laboratory results) at week 0, prior to randomization.

Subject randomization will be stratified according to consent for skin biopsy collection (y/n), and other features (e.g., presence of lupus nephritis [y/n], baseline SLE medications and SLEDAI score), site/region, and race, or concomitant medications as described in Section 8.

Approximately 100 subjects will be randomly assigned by 3:2 ratio to receive either ustekinumab or placebo through Week 24. Following randomization at Week 0, subjects will receive an initial body weight-range based IV dose approximating 6 mg/kg of ustekinumab (ustekinumab 260 mg [weight ≥35 kg to ≤55 kg]; ustekinumab 390 mg [weight >55 kg and ≤85 kg]; ustekinumab 520 mg [weight >85 kg]) followed by 90 mg SC administered q8w (Section 6). At Week 24, subjects receiving placebo will cross-over and all subjects will receive ustekinumab 90 mg SC at Weeks 24, 32, and 40 followed by safety follow-up through Week 56 in a blinded fashion for 16 weeks (i.e., approximately 5 half-lives) after last study agent SC administration.

A placebo comparator (added to standard of care background therapy) will be used through Week 24 for the evaluation of the efficacy and safety of ustekinumab in subjects with SLE. From Week 24 through Week 40, the placebo group will cross-over to ustekinumab 90 mg SC q8w. This cross-over design will permit placebo subjects to receive study agent and provide experience with ustekinumab 90 mg SC without the IV loading dose in subjects with SLE. The 40-Week dosing period will be useful to understand the longer-term safety and time course of potential clinical response of ustekinumab in the SLE population.

Every reasonable effort should be made to keep concomitant medications stable as defined in the protocol. All concomitant therapies must be recorded throughout the study beginning at entry into screening and any changes must be recorded throughout the study.

All subjects with cutaneous disease will be evaluated using CLASI scoring. Additionally, subjects with cutaneous disease who consent to participate in the cutaneous lupus substudy will have other assessments including collection of skin biopsies (optional consent) and/or photographs of an identified cutaneous lesion or area of active disease (optional consent). There will not be any restrictions on the number of subjects with cutaneous disease who can enroll into either the main study or the cutaneous lupus substudy.

Interim analyses (IA) will be conducted when approximately ⅓ and ⅔ of subjects reach Week 24. In the first IA, only evidence for notable efficacy will be assessed. In the second IA, evidence for notable efficacy as well as treatment futility will be analyzed. Variations in placebo effect across regions will be incorporated into the interim analyses. Database locks (DBLs) will occur at Weeks 24 and after the final subject's Week 56 visit or following the last subject's 16-week safety follow-up visit from the main study. In addition, an independent data monitoring committee (DMC) will review interim safety data periodically including a formal review when approximately ⅓ and ⅔ of subjects reach Week 24, as well as at the Week 24 DBL. The DMC will make a recommendation to the Sponsor committee whether the study should be stopped for futility or for safety concerns or if data meet prespecified criteria demonstrating notable efficacy. The content of the summaries, the DMC role and responsibilities, and the general procedures (including communications) will be defined in the DMC charter.

The amended study design will continue to provide open-label ustekinumab 90 mg q8w SC administration through Week 104 (study extension). Subjects will be eligible to continue study treatment through Week 104 if they meet the study inclusion criteria (Section 4.13):

must not have permanently discontinued study treatment on or before their Week 40 visit, and are able to continue q8 week study treatment at approximately 8 weeks (±2 weeks) after their Week 40 visit or are able to resume study treatment with no more than 16 weeks (±2 weeks) since their Week 40 visit In addition to the DBL planned following the last subject's Week 56 visit or the final 16-week safety follow-up visit from the main study, there will be an additional DBL following the Extension 16-Week Safety Follow-up period.

Figure 2:
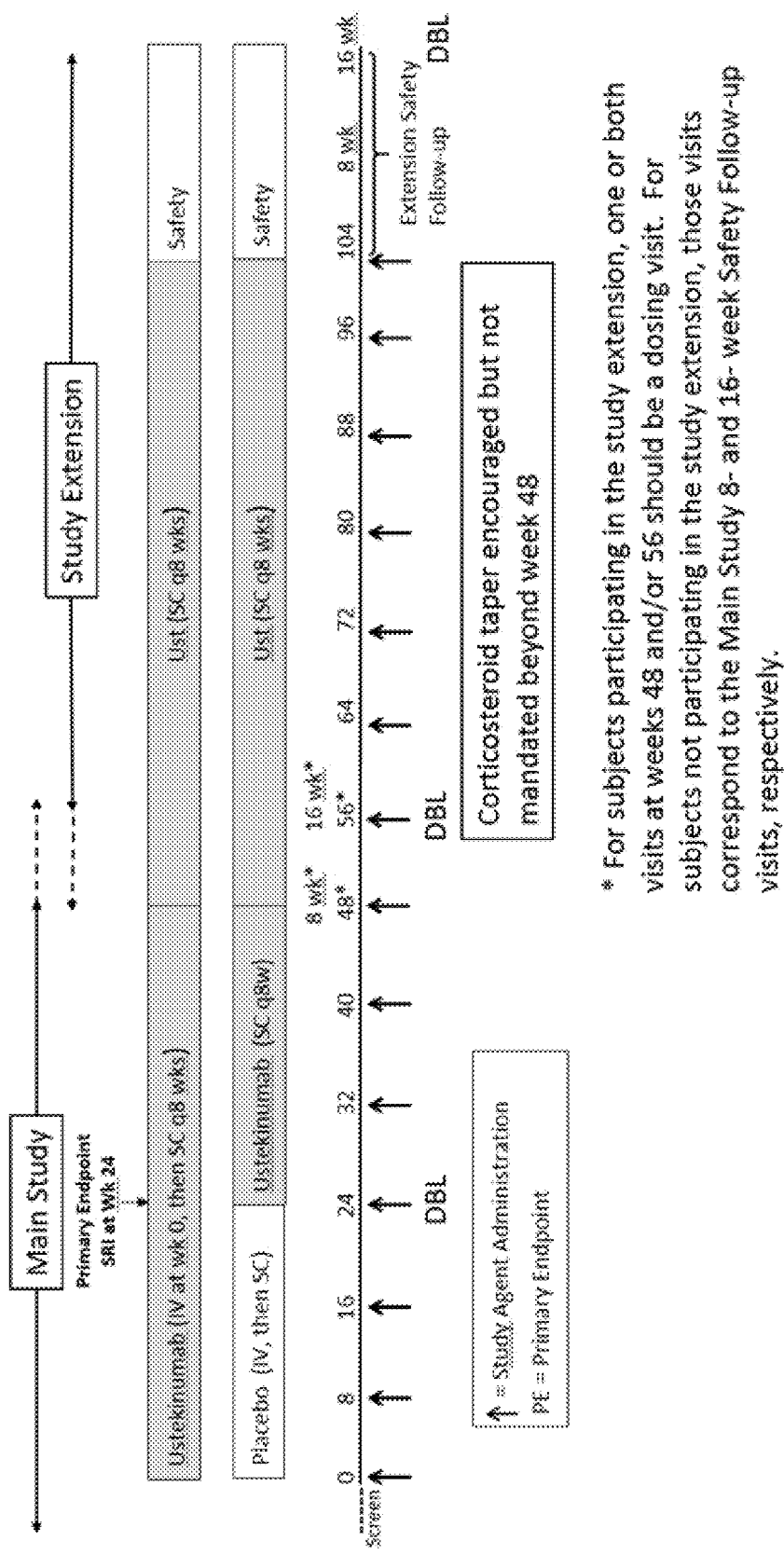
FIG. 2: Shows a Schematic Overview of the Study Including the Study Extension. Abbreviations: DBL=database lock; FU=follow-up; IV=intravenous; PE=primary endpoint; PL=placebo; q8w=every 8 weeks; SC=subcutaneous; SLE=systemic lupus erythematosus; SRI=SLEDAI-2K Responder Index; Wks=weeks.
Figure 3:
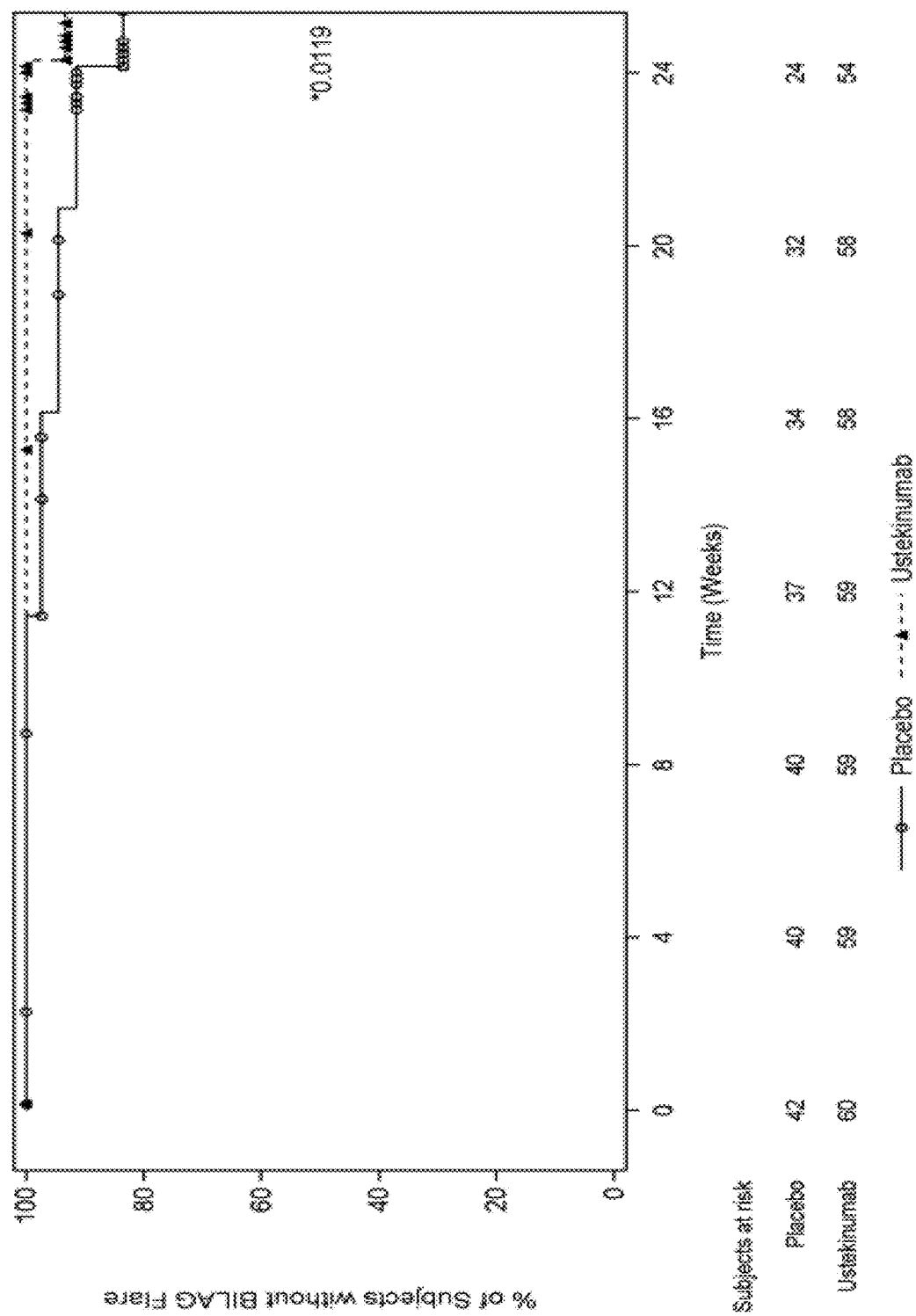
FIG. 3: Shows a Kaplan Meier Plot of BILAG Flare Free Time from Week 12 Through Week 24; Full Analysis Set. BILAG flare defined as at least 1 new BILAG A or 2 new BILAG B scores (from scores <B). Counts include subjects available for analysis at a given visit. Values for subjects meeting treatment failure criteria are set to missing from the point of treatment failure forward. *Test for greater treatment effect in ustekinumab over placebo performed using a log-rank test.

A diagram of the main study design is provided in FIG. 1, and a diagram of the extended study is provided in FIG. 2.

3.2. Study Design Rationale

Blinding, Control, Study Phase/Periods, Treatment Groups

A placebo control will be used to establish the frequency and magnitude of changes in clinical endpoints that may occur in the absence of active treatment. Randomization will be used to minimize bias in the assignment of subjects to treatment groups, to increase the likelihood that known and unknown subject attributes (e.g., demographic and baseline characteristics) are evenly balanced across treatment groups, and to enhance the validity of statistical comparisons across treatment groups. Blinded treatment will be used to reduce potential bias during data collection and evaluation of clinical endpoints.

DNA and Biomarker Collection

It is recognized that genetic variation can be an important contributory factor to interindividual differences in drug distribution and response and can also serve as a marker for disease susceptibility and prognosis. Pharmacogenomic research may help to explain interindividual variability in clinical outcomes and may help to identify population subgroups that respond differently to a drug. The goal of the pharmacogenomic component is to collect deoxyribonucleic acid (DNA) to allow the identification of genetic factors that may influence the pharmacokinetics, pharmacodynamics, efficacy, safety, or tolerability of ustekinumab and to identify genetic factors associated with SLE.

Biomarker samples will be collected to evaluate the mechanism of action of ustekinumab or help to explain inter-individual variability in clinical outcomes or may help to identify population subgroups that respond differently to a drug. The goal of the biomarker analyses is to evaluate the pharmacodynamics of ustekinumab and aid in evaluating the drug-clinical response relationship.

DNA and Biomarker samples may be used to help address emerging issues and to enable the development of safer, more effective, and ultimately individualized therapies.

4. Subject Population

The target study population is subjects with SLE according to SLICC criteria and SLEDAI-2K score >6, despite conventional treatment (e.g., immunomodulators, antimalarial drugs, corticosteroids, NSAIDs, anti-hypertensive drugs, and/or topical medications). Subjects must have at least 1 BILAG A and/or 2 BILAG B domain scores observed during screening. In addition, subjects must have at least 1 positive autoantibody test (ANA, anti-dsDNA antibodies, and/or anti-Smith antibodies) observed during screening, as well as a well-documented positive autoantibody test in their medical history, and they must also have a clinical SLEDAI-2K score ≥4 (excluding laboratory results) prior to randomization at week 0.

The inclusion and exclusion criteria for enrolling subjects in this study are described in the following 2 subsections. If there is a question about the inclusion or exclusion criteria, the investigator should consult with the appropriate Sponsor representative before enrolling a subject in the study.

Subjects with SLE enrolling into the main study with active cutaneous lupus (including subjects with discoid lupus erythematosus, subacute cutaneous lupus erythematosus, or SLE malar rash or other SLE skin lesions characterized by erythema and/or scale) will be evaluated using CLASI scoring. In addition, subjects who provide consent will be enrolled in the cutaneous lupus substudy evaluating the histology of cutaneous biopsies and/or skin photographs. Biopsy samples (2 samples, 4 mm size) from consenting subjects will be collected prior to dosing at Week 0 and at Week 24 from a lesion demonstrating active cutaneous disease. Subjects participating in the cutaneous lupus substudy are not required to undergo biopsies, and may allow only photographs to document changes in an identified cutaneous lesion or area of active disease. Subjects with cutaneous lupus deemed unsuitable for biopsy (e.g., malar rash or alopecia) can also be enrolled in the substudy, and may be evaluated by photography.

If a subject has failed screening and investigator wishes to rescreen the subject, this should be discussed with the study Sponsor and/or their designee. Only 1 rescreening is allowed per subject (also see Section 9.1.2).

The study extension population will be comprised of those subjects who have not permanently discontinued study treatment before or at the Week 40 dose and for whom the investigators judge that there is a potential benefit that outweighs the potential risks to continued ustekinumab treatment.

For a discussion of the statistical considerations of subject selection, refer to Section 11.2, Sample Size Determination.

4.1. Inclusion Criteria

4.1.1. Inclusion Criteria Applicable to All Subjects

Each potential subject must satisfy all of the following criteria to be enrolled in the study.
1. Subject must be between 18 (or older as per local requirements) and 75 years of age, inclusive, and weigh at least 35 kg.
2. Subjects must have documented medical history to meet SLICC classification criteria for SLE for a minimum of 3 months prior to first dose (Table 3).

Subjects eligible for enrollment in this study must qualify as having SLE by meeting the SLICC classification criteria for SLE25 based upon 1 or both of the following:
   Meeting 4 criteria with at least 1 clinical criterion and at least 1 immunologic criterion, or
   A diagnosis of lupus nephritis with presence of at least 1 of the immunological variables

TABLE 3

Clinical and Immunological Criteria Used in the SLICC Classification Criteria*[25]

| Clinical Criteria | | Specific Criteria |
|---|---|---|
| 1. | Acute Cutaneous Lupus including lupus malar rash (do not count if malar discoid) | Bullous lupus<br>Toxic epidermal necrolysis variant of SLE<br>Maculopapular lupus rash<br>Photosensitive lupus rash (in absence of dermatomyositis)<br>Subacute cutaneous lupus (nonindurated psoriaform and/or annular polycyclic lesions that resolve without scarring, although occasionally with postinflammatory dyspigmentation or telangiectasias) |
| 2. | Chronic cutaneous lupus including classical discoid rash | Localized (above the neck)<br>Generalized (above and below the neck)<br>Hypertrophic (verrucous) lupus<br>Lupus panniculitis (profundus)<br>Mucosal lupus<br>Lupus erythematosus tumidus<br>Chilblains lupus<br>Discoid lupus/lichen planus overlap |
| 3. | Oral ulcers: palate | Buccal<br>Tongue<br>Nasal<br>In the absence of other causes such as vasculitis, Behcets, infection (herpes), inflammatory bowel disease, reactive arthritis, and acidic foods |
| 4. | Non-scarring alopecia (diffuse thinning or hair fragility with visible broken hairs) | In the absence of other causes such as alopecia areata, drugs, iron deficiency and androgenic alopecia |

TABLE 3-continued

Clinical and Immunological Criteria Used in the SLICC Classification Criteria*[25]

| Clinical Criteria | | Specific Criteria |
|---|---|---|
| 5. | Synovitis involving two or more joints | Characterized by swelling or effusion OR tenderness in 2 or more joints and thirty minutes or more of morning stiffness |
| 6. | Serositis | Typical pleurisy for more than 1 day<br>Or pleural effusions<br>Or pleural rub<br>Typical pericardial pain (pain with recumbency improved by sitting forward) for more than 1 day<br>Or pericardial effusion<br>Or pericardial rub<br>Or pericarditis by EKG<br>In the absence of other causes such as infection, uremia and Dressier's pericarditis |
| 7. | Renal | Urine protein/creatinine (or 24-hour urine protein) representing 500 mg of protein/24 hour, or<br>Red blood cell casts |
| 8. | Neurologic | Seizures<br>Psychosis<br>Mononeuritis multiplex (in the absence of other known causes such as primary vasculitis)<br>Myelitis<br>Peripheral or cranial neuropathy (in the absence of other known causes such as primary vasculitis, infection and diabetes mellitus)<br>Acute confusional state (in the absence of other causes including toxic-metabolic, uremia, drugs) |
| 9. | Hemolytic anemia | Presence |
| | 10a. Leukopenia ($<4000/mm^3$ at least once), or | In the absence of other known causes such as Felty's, drugs, and portal hypertension |
| | 10b. Lymphopenia ($<1000/mm3$ at least once) | In the absence of other known causes such as corticosteroids, drugs, and infection |
| | 11. Thrombocytopenia ($<100,000/mm^3$ at least once) | In the absence of other known causes such as drugs, portal hypertension, and TTP |
| Immunological Criteria | | Specific Criteria |
| 1. | ANA | above laboratory reference range |
| 2. | Anti-dsDNA | above laboratory reference range, except ELISA; twice above laboratory reference range |
| 3. | Anti-Smith | Presence |
| 4. | Anti-phospholipid antibody (any shown to right) | Lupus anticoagulant<br>False-positive RPR<br>Medium or high titer anticardiolipin (IgA, IgG or IgM)<br>Anti-$\beta_2$ glycoprotein 1 (IgA, IgG or IgM) |
| 5. | Low Complement | Low C3<br>Low C4<br>Low CH50 |
| 6. | Direct Coombs test | In the absence of hemolytic anemia |

*Criteria are cumulative and do not need to be present concurrently

3. To be eligible for study enrollment, subjects must have:
   At least 1 well-documented (subject file, referring physician letter, or laboratory result) unequivocally positive, documented test for autoantibodies in medical history including either of the following: ANA, and/or anti dsDNA antibodies, and/or anti Smith antibodies (Section 9.1.2).
   At least 1 unequivocally positive autoantibody test including ANA and/or anti dsDNA antibodies and/or anti Smith antibodies (Section 9.1.2) detected during screening.
   At least 1 BILAG A and/or 2 BILAG B domain scores observed during screening prior to first administration of study agent.

4. Demonstrate active disease based on SLEDAI-2K score ≥6 observed during screening and assessed approximately 2 to 6 weeks prior to randomization. Must also have SLEDAI-2K ≥4 for clinical features (i.e., SLEDAI excluding laboratory results) at Week 0 prior to the first administration of study agent.
5. Data from the SLICC, SLEDAI and BILAG evaluations will be reviewed and adjudicated by the Sponsor and/or the Sponsor-selected independent reviewer(s). For subjects to receive their first administration of study agent, approval must be received by the Sponsor and/or Sponsor-selected independent reviewers.
6. If using oral corticosteroids, subjects must be receiving this medication for at least 6 weeks and on a stable dose equivalent to an average dose of ≤20 mg/day of prednisone for at least 4 weeks prior to the first administration of study agent. If currently not using corticosteroids, must have not received oral corticosteroids for at least 6 weeks prior to the first administration of study agent.
7. If using antimalarials (e.g., chloroquine, hydroxychloroquine, or quinacrine), subjects must have used the medication for ≥8 weeks and be on a stable dose for at least 6 weeks prior to the first administration of study agent.
8. If using immunomodulatory drugs (mycophenolate mofetil [MMF]/mycophenolic acid [MPA] ≤2 g/day, azathioprine/6 mercaptopurine (AZA/6 MP) ≤2 mg/kg/day and/or MTX ≤25 mg/wk with concomitant folic acid [recommend ≥5 mg/wk]), subjects must be receiving a stable dose for at least 6 weeks prior to the first administration of study agent.
9. If receiving regular treatment with NSAIDs or other analgesics, subjects must be receiving stable dosing for at least 2 weeks prior to first administration of study agent.
10. Before randomization, a woman must be either:
    Not of childbearing potential: premenarchal; postmenopausal (>45 years of age with amenorrhea for at least 12 months); permanently sterilized (e.g., tubal occlusion, hysterectomy, bilateral salpingectomy); or otherwise be incapable of pregnancy.
    Of childbearing potential and practicing a highly effective method of birth control consistent with local regulations regarding the use of birth control methods for subjects participating in clinical studies: e.g., established use of oral, injected or implanted hormonal methods of contraception associated with inhibition of ovulation; placement of an intrauterine device or intrauterine system; male partner sterilization (the vasectomized partner should be the sole partner for that subject); true abstinence (when this is in line with the preferred and usual lifestyle of the subject).
    Note: If the childbearing potential changes after start of the study (e.g., woman who is not heterosexually active becomes active, premenarchal woman experiences menarche) a woman must begin a highly effective method of birth control, as described above.
11. A woman of childbearing potential must have a negative serum pregnancy test β-human chorionic gonadotropin [β-hCG]) at screening, and a negative urine pregnancy test at Week 0 before the first administration of study agent.
12. Women of childbearing potential must be willing to remain on a highly effective method of birth control during the study and for 4 months after receiving the last study agent. Also, women of childbearing potential must agree to not donate eggs (ova, oocytes) for the purposes of assisted reproduction during the study and for 4 months after receiving the last dose of study agent.
13. A man who is sexually active with a woman of childbearing potential and has not had a vasectomy must agree to use a barrier method of birth control e.g., either condom with spermicidal foam/gel/film/cream/suppository or partner with occlusive cap (diaphragm or cervical/vault caps) with spermicidal foam/gel/film/cream/suppository, and all men must also not donate sperm during the study and for 4 months after receiving the last dose of study agent.
14. Are considered eligible according to the following tuberculosis (TB) screening criteria:
    a. Have no history of latent or active TB prior to screening. An exception is made for subjects who have a history of latent TB and are currently receiving treatment for latent TB, will initiate treatment for latent TB prior to first administration of study agent, or have documentation of having completed appropriate treatment for latent TB within 3 years prior to the first administration of study agent. It is the responsibility of the investigator to verify the adequacy of previous anti-tuberculous treatment and provide appropriate documentation.
    b. Have no signs or symptoms suggestive of active TB upon medical history and/or physical examination.
    c. Have had no recent close contact with a person with active TB or, if there has been such contact, will be referred to a physician specializing in TB to undergo additional evaluation and, if warranted, receive appropriate treatment for latent TB prior to the first administration of study agent.
    d. Within 6 weeks prior to the first administration of study agent, have a negative QuantiFERON®-TB Gold test result, or have a newly identified positive QuantiFERON®-TB Gold test result in which active TB has been ruled out and for which appropriate treatment for latent TB has been initiated prior to the first administration of study agent. Within 6 weeks prior to the first administration of study agent, a negative tuberculin skin test, or a newly identified positive tuberculin skin test in which active TB has been ruled out and for which appropriate treatment for latent TB has been initiated prior to the first administration of study agent, is additionally required if the QuantiFERON®-TB Gold test is not approved/registered in that country or the tuberculin skin test is mandated by local health authorities.
        i. Subjects with persistently indeterminate QuantiFERON®-TB Gold test results may be enrolled without treatment for latent TB, if active TB is ruled out, their chest radiograph shows no abnormality suggestive of TB (active or old, inactive TB), and the subject has no additional risk factors for TB as determined by the investigator. This determination must be promptly reported to the Sponsor's medical monitor and recorded in the subject's source documents and initialed by the investigator.
        ii. The QuantiFERON®-TB Gold test and the tuberculin skin test are not required at screening for subjects with a history of latent TB and ongoing treatment for latent TB or documentation of having completed adequate treatment as described above; Subjects with documentation of having completed adequate treatment as described above are not required to initiate additional treatment for latent TB.
    e. Subjects who test positive for TB by a TB test other than QuantiFERON®-TB Gold and TB skin test and who have no evidence of TB on chest radiograph will in the context of this protocol be considered latent TB positive and be required to undergo evaluation by a TB specialist and receive treatment for TB to be eligible for this study.
    f. Have a chest radiograph (both posterior-anterior and lateral views) taken within 3 months prior to the first administration of study agent and read by a qualified radiologist or pulmonologist, with no evidence of current, active TB or old, inactive TB.
15. Have laboratory test results within the following parameters at screening:

| | | |
|---|---|---|
| Hemoglobin | ≥8.5 g/dL | (SI: ≥85 g/L) |
| Lymphocytes | ≥0.5 × 10³/μL | (SI: ≥0.5 GI/L) |
| Neutrophils | ≥1.0 × 10³/μL | (SI: ≥1.0 GI/L) |
| Platelets | ≥75 × 10³/μL | (SI: ≥75 GI/L) |
| Serum creatinine | ≤1.8 mg/dL | (SI: ≤159 μmol/L) |
| White blood cells | ≥2.0 × 10³/μL | (SI: ≥2.0 GI/L) |

The aspartate aminotransferase, alanine aminotransferase, and alkaline phosphatase levels must be within 2× upper limit of normal (ULN) range for the laboratory conducting the test. For subjects within the range of 1.5 to 2×ULN for transaminases, the subject may be included only if the investigator judges the abnormalities or deviations from normal to not be clinically significant or to be appropriate and reasonable for the population under study. This determination must be promptly reported to the Sponsor's medical monitor and recorded in the subject's source documents and initialed by the investigator.

Subjects with other marked disease-associated laboratory abnormalities may be included only if the investigator judges the abnormalities or deviations from normal to be not clinically significant or to be appropriate and reasonable for the population under study. This determination must be promptly reported to the Sponsor's medical monitor and recorded in the subject's source documents and initialed by the investigator.

16. Subject must be willing and able to adhere to the prohibitions and restrictions specified in this protocol.
17. Each subject must sign an informed consent form (ICF) indicating that he or she understands the purpose of and procedures required for the study and are willing to participate in the study.
18. Each subject must sign a separate informed consent form if he or she agrees to provide an optional DNA sample for research (where local regulations permit). Refusal to give consent for the optional DNA research sample does not exclude a subject from participation in the study.

4.1.2. Additional Inclusion Criteria for the Cutaneous Lupus Substudy

To be enrolled in the cutaneous lupus substudy, an SLE subject must satisfy all previously listed inclusion criteria (Section 4.1.1) in addition to the criteria listed below:
1. Have diagnosis of active CLE at screening as well as documented cutaneous disease prior to study enrollment, including subjects with discoid lupus erythematosus, subacute cutaneous lupus erythematosus, or SLE malar rash or other SLE skin lesions including those characterized by erythema and/or scale.
2. Subjects taking systemic, topical, or intra-lesional medications for CLE must be on a stable dose or treatment regimen for 4 weeks prior to first study agent administration.
3. Subjects who consent to participate in the cutaneous lupus substudy will be asked to provide biopsies of an active CLE target lesion prior to dosing at Weeks 0 and 24. An active CLE lesion is characterized by scale and/or erythema, excluding previously scarred tissue. In addition, separate consent will be obtained to collect photographs of a cutaneous lesion or area of active disease according to the schedule defined in Table 1.
4. Subjects with cutaneous lupus deemed unsuitable for biopsy (e.g., malar rash or alopecia) can also be enrolled in the substudy, and may be evaluated by photography.

4.1.3. Inclusion Criteria Applicable to All Subjects Entering into the Study Extension (Week 48 or Week 56 Visits)

Any subjects who do not meet the inclusion criteria for the study extension must follow the Time and Events schedule for the main study design (Table 1), and have safety follow-up visits conducted at 8 and 16 weeks following their Week 40 or final study dose.
1. Subjects must not have permanently discontinued study treatment on or before their Week 40 visit, and are able to either continue q8w SC dosing at approximately 8 weeks (±2 weeks) after their Week 40 visit, or are able to resume dosing at Week 56 with no more than 16 weeks (±2 weeks) since their Week 40 visit.
2. In the judgment of the study investigator, the potential benefit of continuing ustekinumab long-term treatment outweighs the potential risks for the subject.
3. Each subject must sign a revised informed consent indicating agreement to participate in the extended study.

4.2. Exclusion Criteria

Any potential subject who meets any of the following criteria will be excluded from participating in the study.
1. Have other inflammatory diseases that might confound the evaluations of efficacy, including but not limited to rheumatoid arthritis (RA), psoriatic arthritis (PsA), RA/lupus overlap, psoriasis, or active Lyme disease.
2. Are pregnant, nursing, or planning a pregnancy or fathering a child while enrolled in the study or within 4 months after receiving the last administration of study agent.
3. Have received systemic or topical cream/ointment preparations of cyclosporine A or other systemic immunomodulatory agents other than those described in inclusion criteria within the past 3 months prior to first administration of study agent (Section 4.1). Corticosteroids are not included in this criterion; see Sections 4.3 and 8.3 regarding corticosteroids.
4. Have received a single B cell targeting agent within 3 months prior to first study agent administration; or received more than 1 previous B cell targeting therapy including belimumab or epratuzamab within 6 months prior to first administration of the study agent; or received B cell depleting therapy (e.g., rituximab) within 12 months prior to first administration of the study agent or have evidence of continued B cell depletion following such therapy.
5. Have ever received ustekinumab.
6. Have received prior immunomodulatory biologic therapy for lupus not described in Exclusion Criterion #4 including, but not limited to, tocilizumab, alefacept, efalizumab, natalizumab, abatacept, anakinra, brodalumab, secukinumab, ixekizumab, or inhibitors of TNF, IL-1, IL-6, IL-17, or interferon pathways, less than 5 half-lives or 3 months, whichever is longer, prior to first administration of the study agent.

7. Have a known hypersensitivity to human immunoglobulin (Ig) proteins (e.g., intravenous Ig).
8. Have used oral cyclophosphamide within 90 days or IV cyclophosphamide within 180 days of starting screening.
9. Have a history of active granulomatous infection, including histoplasmosis, or coccidioidomycosis, prior to screening. Refer to inclusion criteria for information regarding eligibility with a history of latent TB.
10. Have had a Bacille Calmette-Guérin (BCG) vaccination within 12 months of screening.
11. Have a chest radiograph within 3 months prior to the first administration of study agent that shows an abnormality suggestive of a malignancy or current active infection, including TB.
12. Have had a nontuberculous mycobacterial infection or opportunistic infection (e.g., cytomegalovirus, pneumocystosis, aspergillosis) within 6 months prior to screening.
13. Have received, or are expected to receive, any live virus or bacterial vaccination within 3 months before the first administration of study agent, during the study, or within 3 months after the last administration of study agent. For BCG vaccination criterion, see Exclusion Criterion 10 and Prohibition/Restriction Criterion 8.
14. Have had a serious infection (including but not limited to, hepatitis, pneumonia, sepsis, or pyelonephritis), or have been hospitalized for an infection, or have been treated with intravenous antibiotics for an infection within 2 months prior to first administration of study agent. Less serious infections (e.g., acute upper respiratory tract infection, simple urinary tract infection) need not be considered exclusionary at the discretion of the investigator.
15. Have a history of, or ongoing, chronic or recurrent infectious disease, including but not limited to, chronic renal infection, chronic chest infection (e.g., bronchiectasis), sinusitis, recurrent urinary tract infection (e.g., recurrent pyelonephritis), an open, draining, or infected skin wound, or an ulcer.
16. Subject has a history of human immunodeficiency virus (HIV) antibody positive, or tests positive for HIV at screening.
17. Has a hepatitis B infection. Subjects must undergo screening for hepatitis B virus (HBV). At a minimum, this includes testing for HBsAg (HBV surface antigen), anti HBs (HBV surface antibody), and anti-HBc total (HBV core antibody total).
18. Subjects who are seropositive for antibodies to hepatitis C virus (HCV), unless they have 2 negative HCV RNA test results 6 months apart prior to screening and have a third negative HCV RNA test result at screening.
19. Subjects having experienced a recent single dermatomal herpes zoster eruption within the past 4 months are excluded. Those with multi-dermatomal herpes zoster or central nervous system (CNS) zoster within the past 5 years are excluded.
20. Subjects with a history or suspected occurrence of drug-induced lupus.
21. Have urinary protein >4 g/day or protein/creatinine ratio >4.
22. Have inherited complement deficiency or combined variable immunodeficiency.
23. Have end-stage renal disease, or severe or rapidly progressive glomerulonephritis, including severe, active lupus nephritis reported in recent biopsy and/or other assessments such as active urinary sediment, rapidly increasing creatinine, or other factors that suggest severe or rapidly progressing nephritis (see also limits on serum creatinine in Inclusion Criterion #15).
24. Have severe CNS lupus including but not limited to seizures, psychosis, transverse myelitis, CNS vasculitis and optic neuritis.
25. Have severe, progressive, or uncontrolled hepatic, hematological, gastrointestinal, endocrine, pulmonary, cardiac, neurologic/cerebral, or psychiatric disease, or current signs and symptoms thereof.
26. Have a known history of lymphoproliferative disease, including lymphoma, or signs and symptoms suggestive of possible lymphoproliferative disease, such as lymphadenopathy of unusual size or location, clinically significant splenomegaly, or history of monoclonal gammopathy of undetermined significance.
27. Subject has a history of malignancy within 5 years before screening (exceptions are squamous and basal cell carcinomas of the skin that has been treated with no evidence of recurrence for at least 3 months before the first study agent administration and carcinoma in situ of the cervix that has been surgically cured).
28. Has known allergies, hypersensitivity, or intolerance to ustekinumab, its excipients or latex (contained in the syringe needle cover, see Section 14.1).
29. Are currently receiving venom immunotherapy (honeybee, wasp, yellow jacket, hornet, or fire ant).
30. Has received an investigational drug that is not previously defined in other exclusion criteria (including investigational vaccines or other medications specified in section 4.3, Prohibition/Restriction No. 3) within 5 half lives or 3 months, whichever is longer, or used an invasive investigational medical device within 3 months before the planned first dose of study drug, or is currently enrolled in an interventional study.
31. Has any condition for which, in the opinion of the investigator and/or Sponsor, participation would not be in the best interest of the subject (e.g., compromise the well being) or that could prevent, limit, or confound the protocol-specified assessments including a previous pattern of non-compliance with medical follow-up or being deemed unlikely to be compliant with a study visit schedule.
32. Has had major surgery, (e.g., requiring general anesthesia) within 1 month before screening, or will not have fully recovered from surgery, or has major surgery (e.g., requiring general anesthesia) planned during the time the subject is expected to participate in the study or within 1 month after the last dose of study drug administration.

Note: Subjects with planned minor surgical procedures to be conducted under local anesthesia may participate.

33. Have a transplanted organ (with the exception of a corneal transplant performed >3 months prior to first administration of study agent).
34. Have or have had a substance abuse (drug or alcohol) problem within the previous 3 years.
35. Are unwilling or unable to undergo multiple venipunctures because of poor tolerability or lack of easy venous access.
36. Subject is an employee of the investigator or study site (i.e. personnel to whom the investigator has delegated a role or responsibility for conducting the study), with direct involvement in the proposed study or other studies under the direction of that investigator or study site, as well as family members of the employees or the investigator.

37. Lives in an institution on court or authority order, unless permitted by local regulations.

NOTE: Investigators should ensure that all study enrollment criteria have been met at screening. If a subject's status changes (including laboratory results or receipt of additional medical records) after screening but before the first dose of study drug is given such that he or she no longer meets all eligibility criteria, then the subject should be excluded from participation in the study. Sponsor reserves the right to discontinue the subject for any operational or safety reasons.

4.3. Prohibitions and Restrictions

Potential subjects must be willing and able to adhere to the following prohibitions and restrictions during the course of the study (including the study extension) to be eligible for continued dosing in the study:
1. If a woman is capable of pregnancy, she must remain on a highly effective method of birth control during the study and for 4 months after receiving the last study agent. The exception to this restriction is if the subject or her male partner is sterilized; this situation does not require birth control. A woman must not donate eggs (ova, oocytes) for the purposes of assisted reproduction during the study and for 4 months after receiving the last dose of study agent.
2. If a man, he is to use an effective method of birth control and not donate sperm during the study and for 4 months after receiving the last dose of study agent. The exception to this is if the subject or his female partner is sterilized; this situation does not require birth control.
3. Use of additional immunosuppressants or immunomodulators, other than those explicitly allowed in the inclusion/exclusion criteria, are prohibited including but not limited to the following:
    Biologic agents targeted at reducing TNF☐ (including but not limited to infliximab, golimumab, certolizumab pegol, etanercept, yisaipu, CT-P13 [Remsima®] and adalimumab)
    B cell depleting agents (anti-CD20 [e.g., rituximab], anti-B cell activating factor [BAFF], also known as B lymphocyte stimulator [BLyS], [e.g., belimumab], or anti CD22 [e.g., epratuzumab])
    Interleukin-1 inhibitors (e.g., canakinumab)
    Interferon inhibitors
    IL-1ra (e.g., anakinra)
    Tocilizumab or any other biologic targeting IL-6 or IL-6 receptor
    Tofacitinib or any other j anus kinase (JAK) inhibitor
    Abatacept
    Anti-IL-17 agents (e.g., brodalumab, secukinumab, and ixekizumab)
    Leflunomide
    Cyclosporine A (oral or topical ointment/cream preparations)
    Tacrolimus or picrolimus, oral or topical preparations
    Toll-like receptor inhibitors
    Thalidomide or lenalidomide
    Dapsone
    Adrenocorticotropic hormone (ACTH) by injection
4. Use of cytotoxic drugs is prohibited including, but not limited to, cyclophosphamide, chlorambucil, nitrogen mustard, or other alkylating agents.
5. Multiple administrations of high doses of corticosteroids, and initiation of medium or high potency topical corticosteroids, are prohibited during the study as defined in Section 8.3.
6. The initiation of a new permitted immunomodulatory agent (MTX, azathioprine, 6-mercaptopurine, mycophenolate mofetil/mycophenolic acid) in addition to an ongoing immunomodulatory therapy is prohibited.
7. Initiation of new angiotensin II receptor blocker (ARB) or angiotensin-converting enzyme (ACE) inhibitor therapy after first dose of study agent is not permitted for the treatment of lupus-related disease through Week 28.
8. Must agree not to receive a live virus or live bacterial vaccination during the study. Subjects must also agree not to receive BCG vaccination for 12 months after last dose of study agent, or any other live vaccine for 3 months after receiving the last administration of study agent.
9. Must agree not to receive an investigational medical device or an investigational drug other than study agent for the duration of this study.
10. The use of complementary therapies that may trigger activation of lupus or mitigate the symptoms of SLE, including but not limited to, traditional medicine (e.g., herbal/alternative preparations [e.g., Echinacea], Chinese, acupuncture, ayurvedic) is prohibited through Week 40.
11. Study subjects should avoid excessive sun exposure and may not participate in commercial ultraviolet tanning or ultraviolet phototherapy during the study.
12. Skin concealers or topical tan preparations should be avoided due to their potential to obscure skin disease activity.
13. Sulfa-based antibiotics, where reasonable, should generally be avoided.

5. Treatment Allocation and Blinding 5.1. Procedures for Randomization

Dynamic central randomization will be implemented in conducting this study. Subjects will be assigned to 1 of 2 treatment groups based on a minimization randomization algorithm implemented in the interactive web response system (IWRS) before the study. Dynamic central randomization targets to balance the distribution of subjects to achieve the randomization ratio (3:2) at the study level and within the levels of each individual stratification factor: skin biopsy (y/n, when n<16 for y), presence of lupus nephritis (y/n), baseline SLE medications and SLEDAI-2K score (combined factor)*, site, region (approximately 4 categories), and race (3 categories). Based on the algorithm, each subject will be assigned to the treatment group which will produce minimum total imbalance score with a high probability, where the total imbalance score is a weighted average of the imbalance scores for each stratification factor and for the whole study. The IWRS will the assign a unique treatment code, which will dictate the treatment assignment for the subject.

The baseline SLE medications and SLEDAI-2K score will be calculated as a combined factor, including:
    SLEDAI-2K score (<10 or ≥10) combined with
    Baseline medications:
        High medications defined as ≥15 mg/wk MTX, or ≥1.5 mg/kg/day AZA/6-MP, or ≥1.5 g/day MMF/MPA, and/or ≥15 mg/day prednisone.

Low medications defined as <15 mg/wk MTX, or <1.5 mg/kg/day AZA/6-MP, or <1.5 g/day MMF/MPA, and/or <15 mg/day prednisone.

5.2. Blinding

The investigator will not be provided with randomization codes. The codes will be maintained within the IWRS, which has the functionality to allow the investigator to break the blind for an individual subject.

Under normal circumstances, the blind should not be broken until all subjects have completed the study at Week 56 or terminated study participation, and the database is finalized. Otherwise, the blind should be broken only if specific emergency treatment/course of action would be dictated by knowing the treatment status of the subject. In such cases, the investigator may in an emergency determine the identity of the treatment by contacting IWRS. It is recommended that the investigator contact the Sponsor or its designee if possible to discuss the particular situation, before breaking the blind. Telephone contact with the Sponsor or its designee will be available 24 hours per day, 7 days per week. In the event the blind is broken, the Sponsor must be informed as soon as possible. The date and reason for the unblinding must be documented by the IWRS. The documentation received from the IWRS indicating the code break must be retained with the subject's source documents in a secure manner.

Subjects who have had their treatment assignment unblinded may be discontinued from further administration of study agent and should return for safety follow-up.

In general, randomization codes will be disclosed fully only if the study is completed and the clinical database is closed. The Sponsor will be blinded through the Week 24 evaluation and until the database is cleaned and finalized for planned analyses. The clinical site, subjects, investigators, and site personnel will remain blinded through the end of the study until Week 56 data are finalized. Data that may potentially unblind the treatment assignment will be handled with special care.

6. Dosage and Administration

6.1. IV Administration

For IV administration, the study agent will be administered to each subject over a period of not less than 1 hour.

Ustekinumab 5 mg/mL Final Vialed Product (FVP) (IV) is supplied as a single-use, sterile solution in 30 mL vials with 1 dose strength (i.e., 130 mg in 26 mL nominal volume). In addition to ustekinumab, the solution contains 10 mM L-histidine, 8.5% (w/v) sucrose, 0.04% (w/v) polysorbate 80, 0.4 mg/mL L-methionine, and 20 µg/mL ethylenediaminetetraacetic acid (EDTA) disodium salt dihydrate at pH 6.0. No preservatives are present.

Placebo for FVP (IV) is supplied as single-use, sterile solution in 30 mL vials with a 26 mL nominal volume. The composition of the placebo is 10 mM L-histidine, 8.5% (w/v) sucrose, 0.04% (w/v) polysorbate 80, 0.4 mg/mL L-methionine, and 20 µg/mL EDTA disodium salt dihydrate at pH 6.0. No preservatives are present.

Body weight-range based dosing will allow administration of complete vials to patients to simplify dose calculation and reduce the potential for errors in dosing. This body weight-range based IV dosing is intended to achieve drug exposure similar to that observed with weight adjusted 6 mg/kg dosing. Comparable numbers of vials will be administered to subjects receiving placebo based on their body weight-range. The body weight-range doses are based on the following:

Body weight ≥35 kg and ≤55 kg: 260 mg ustekinumab (2 vials)
Body weight >55 kg and ≤85 kg: 390 mg ustekinumab (3 vials)
Body weight >85 kg: 520 mg ustekinumab (4 vials)

6.2. SC Administration

Ustekinumab will also be supplied as a single-use latex-free prefilled syringe (PFS) in a strength of 90 mg in 1 mL nominal volume for SC administration. Each 1 mL of ustekinumab solution in the PFS contains 90 mg ustekinumab with nominal excipient concentrations of 6.7 mM L-histidine, 7.6% (w/v) sucrose, 0.004% (w/v) polysorbate 80, at pH 6.0. No preservatives are present. The needle cover on the PFS contains dry natural rubber (a derivative of latex), which may cause allergic reactions in individuals sensitive to latex.

Placebo administrations will have the same appearance as the respective ustekinumab administrations. Liquid placebo will also be supplied in a 1 mL PFS, and have a composition 10 mM L-histidine, 8.5% (w/v) sucrose, 0.004% (w/v) polysorbate 80, at pH 6.0. No preservatives are present. The needle cover on the PFS contains dry natural rubber (a derivative of latex), which may cause allergic reactions in individuals sensitive to latex.

Week 0 up to Week 24 (Blinded Study Agent Administration Phase)

Group 1: Subjects will receive weight-range based IV dosing of approximately 6 mg/kg of ustekinumab at Week 0 followed by ustekinumab 90 mg SC administrations at Weeks 8 and 16.

Group 2: Subjects will receive weight-range based IV dosing of placebo at Week 0 followed by placebo SC administrations at Weeks 8 and 16.

Week 24 to Week 40 (Cross-over Administration Phase)

Group 1: Subjects will receive an ustekinumab 90 mg SC administration at Week 24 followed by q8w administrations through Week 40.

Group 2: Subjects will cross-over to ustekinumab 90 mg SC administrations at Week 24 followed by q8w administrations through Week 40.

After Week 40 to 16-Week Safety Follow-Up (Safety Follow-Up Phase)

Groups 1 and 2: Subjects who do not participate in the study extension are expected to return for safety follow-up visits at Weeks 44 and for 8- and 16-weeks safety follow-up.

Study Extension (Week 48/Week 56 Through Week 120)

Subjects who meet the study extension inclusion criteria will receive open-label ustekinumab administration for the purpose of expanding the safety experience and maintenance of efficacy in lupus patients continuously exposed to ustekinumab 90 mg q8w. Subjects who continue dosing in the extended study starting at Week 48 or at Week 56 will receive open-label ustekinumab SC dosing through Week 104. If the development of ustekinumab in SLE is terminated, then the study extension will also be discontinued.

7. Treatment Compliance

Study personnel will maintain a log of all study agent administrations. Study agent supplies for each subject will be inventoried and accounted for. All ongoing therapies administered at the time of screening must be recorded.

Compliance with the treatment schedule is strongly encouraged. It is understood that treatment may be interrupted for health-related or safety reasons. The Weeks 0, 24, and 48 visits are essential for assessing efficacy and safety of ustekinumab as therapy for active SLE.

Therefore, if for any reason a subject cannot receive a dose of study agent at the scheduled visits, the subjects must make every effort to come for scheduled assessments. Through the Week 32 visit, the visit and study agent administration should occur within ±7 days of the scheduled visit day (relative to Week 0). Following the Week 32 visit, the study agent administrations are allowed to occur within ±2 weeks of the scheduled visit day (relative to Week 0). The study agent administrations are scheduled to occur approximately 8 weeks apart, and cannot occur <14 days apart. If there is a delay in treatment, the subject should resume the normal study schedule relative to the baseline visit (Week 0).

All subjects will be monitored by a site monitor designated by the Sponsor. During these monitoring visits, all procedures will be evaluated for compliance with the protocol. Subject charts will be reviewed and compared with earlier data entries on the to ensure accuracy. The Sponsor must be contacted for any deviation to the timeframes above.

8. Concomitant Therapy

All prestudy therapies administered up to 90 days before entry into screening must be recorded at screening. Modification of an effective preexisting therapy should not be made for the explicit purpose of entering a subject into the study. All concomitant therapies must be recorded throughout the study beginning at entry into screening and any changes must be recorded throughout the study.

Every reasonable effort should be made to keep concomitant medications stable at least through Week 28, and if possible also through the main study 8-week safety follow-up or through the study extension (if applicable). With the exception of corticosteroids (see Section 8.3 regarding corticosteroid tapering), all other concomitant medications should be maintained at stable doses throughout the study. A concomitant medication may be reduced or medication temporarily discontinued because of abnormal laboratory values, side effects, concurrent illness, or the performance of a surgical procedure, but the change and reason for the medication change should be clearly documented in the subject's medical record. If concomitant medications have been adjusted after randomization as allowed per protocol, every effort should be made to return subject back to the baseline (Week 0) dose level by the Week 12 visit; or increased medication use (relative to baseline) may render a subject to be considered a treatment failure. Corticosteroid adjustments for cause are permitted as defined in Section 8.3.

The Sponsor must be notified in advance (or as soon as possible thereafter) of any instances in which prohibited therapies are administered.

All pharmacologic therapies (prescription or over-the-counter medications, including vaccines, vitamins, herbal supplements) different from the study agent must be recorded. Subject diary cards will be used to capture changes in subject-administered medications that occur in between study visits during the main portion of this study, and these changes must also be recorded.

8.1. Immunomodulators

If receiving immunomodulators, subjects should be receiving stable dosing from screening through Week 28. Subjects can be receiving MMF/MPA (≤2 g/day), azathioprine/6-mercaptopurine (≤2 mg/kg/day) and/or MTX (≤25 mg/wk) with concomitant folic acid (recommend ≥5 mg/wk), during screening and through Week 28. A reduction in immunomodulators from Week 12 through Week 28 is allowed only if the subject develops unacceptable side effects, with the implication that this may affect interpretation of the subjects' clinical data. A higher dose of an immunomodulator (relative to the baseline dose) or the addition of a new immunomodulator to the existing treatment regimen between the Week 12 and 24 visit will cause subjects to be considered a treatment failure for the purposes of the primary endpoint analysis. Permanent discontinuation of the study treatment must be considered for subjects receiving an increase (relative to baseline) in their immunomodulator dose. Beyond Week 28, immunomodulators should remain as stable as possible through the 8-week safety follow-up or through the study extension (if applicable); however, dose adjustment is allowed for unacceptable side effects.

8.2. Antimalarial Medications

Stable treatment with hydroxychloroquine, chloroquine, or quinacrine is permitted through the 8-week safety follow-up. Beyond Week 28, it is permitted to introduce or adjust dosing of antimalarials. Antimalarials produced by a licensed compounding pharmacy (e.g., quinacrine) in the country of administration and using pharmaceutical grade components are allowed.

8.3. Corticosteroid Therapy

Unnecessary dose changes are discouraged, and any dose adjustments should be made in increments. Changes in corticosteroids through the 8-week safety follow-up or through the study extension (if applicable) are allowed for medical necessity, but the degree and timing of the adjustment should be carefully considered as this may have an impact on the study results, especially during the period between 12 and 28 weeks.

Oral Corticosteroids*

*Rectal administration of corticosteroids, if necessary, should be short-term and using topical preparations.

If using oral corticosteroids, must be receiving this medication for at least 6 weeks and on a stable dose equivalent to an average dose of ≤20 mg of prednisone/day for at least 4 weeks prior to the first administration of study agent. Corticosteroid dose adjustment (increase or decrease) of no more than 5 mg prednisone (equivalent/day) to a maximum dose of 25 mg/day is permitted through Week 6. From Week 6 through Week 12, no corticosteroid dose increases are permitted, and within this window only a gradual decrease of up to 5.0 mg prednisone (equivalent/day) adjustment towards the baseline dose are allowed up to the Week 12 visit. No further adjustments in doses of corticosteroid for the treatment of SLE disease are permitted between Weeks 12 and 28. Following Week 28, changes in corticosteroid dosing through the 8-week safety follow up is allowed for medical necessity, but the degree and timing of the adjustment should be carefully considered as this may have an impact on the study. Dose increases of oral corticosteroids of 40 mg/day or more should be discussed with the medical monitor and may result in discontinuation of study agent administration.

Subjects may receive short courses (2 weeks or less) of oral corticosteroids for reasons such as prophylactic therapy before surgery (stress-dose corticosteroids) or therapy for limited infections, exacerbation of asthma, or chronic obstructive pulmonary disease.

Subjects likely to require multiple courses of steroids for reasons other than SLE should be excluded from study participation.

Gradual tapering of oral corticosteroid dosing in the study extension (recommended reductions of no more than 10 to 20% of the original dose per week) is encouraged starting after the Week 48 dose at the discretion of the study investigator. Tapering to the lowest possible maintenance dose of corticosteroids is recommended, including complete weaning off of corticosteroids if possible. It is recommended that subjects should be educated and monitored by study staff for symptoms of steroid deficiency (e.g., Addisonian symptoms) during periods of steroid tapering, as appropriate.

If subjects experience a worsening in their disease activity while tapering corticosteroids, further dose decreases may be suspended, and/or their oral corticosteroid dose may be temporarily increased if deemed necessary by the investigator. For subjects whose corticosteroid taper is interrupted, investigators are encouraged to resume tapering within 4 weeks.

In the event of increased corticosteroid dosing, it is recommended that the average dose should not be increased above the baseline dose unless medically necessary. Discretion should be used as any corticosteroid increases may render a subject to be considered a treatment or steroid tapering failure. Sustained oral corticosteroid doses of 40 mg/day or higher may result in discontinuation of study agent.

Epidural, Intravenous, Intramuscular, Intra-articular, and Intra-lesional Corticosteroids Epidural, IV, IM, IA, or intra-lesional administration of corticosteroids is strongly discouraged within 4 weeks prior to the first administration of study agent and is not allowed for the treatment of SLE through Week 28. Drugs that induce release of endogenous steroids such as ACTH administered by injection are not allowed within 3 months prior to the first administration of study agent and throughout the study. Short-term (≤2 weeks) epidural, IV, IM, IA, or intra-lesional corticosteroid use for the treatment of indications other than SLE should be limited to situations where, in the opinion of the treating physician, there are no adequate alternatives. If clinically necessary, a total of 1 or 2 IA injections may be permitted up to the Week 16 dosing, however this would render those joints unevaluable for subsequent assessments. For conditions other than SLE, corticosteroid therapy should be limited to situations in which, in the opinion of the treating physician, there are no adequate alternatives. Intravenous corticosteroids of >625 mg prednisone equivalent/day for 2 or more days total in the 24-week period will be evaluated for treatment failure as per the statistical analysis plan (SAP).

Inhalation Corticosteroids

Corticosteroids administered by bronchial or nasal inhalation for treatment of conditions other than SLE may be given as needed.

Corticosteroid Use in Cutaneous Lupus Substudy

For subjects in the cutaneous lupus substudy, the initiation of, or an increase from baseline in, the use of potent topical corticosteroids, or intra-lesional corticosteroid injections, is not allowed and should be avoided through the 8-week safety follow-up or in the study extension.

8.4. Nonsteroidal Anti-inflammatory Drugs

Subjects treated with NSAIDs, including aspirin and selective cyclooxygenase-2 (COX-2) inhibitors, and other analgesics should receive the usual marketed doses approved in the country in which the study is being conducted. Prescriptions of NSAIDs and other regularly administered analgesics should not be adjusted for at least 2 weeks prior to the first administration of the study drug and through Week 28, and may be changed only if the subject develops unacceptable side effects. After Week 16 and through Week 28 the addition of new NSAIDs to the treatment regimen is not permitted. Minor adjustments in NSAID therapy are allowed after Week 28 although it is recommended that the use of any NSAIDS remain as stable as possible, and any notable changes should be recorded.

8.5. Anti-hypertensive Medications

Subjects are permitted to receive stable doses of ARB or ACE inhibitors for the treatment of hypertension and lupus. Initiation of new ARB or ACE inhibitor therapy after first dose of study agent is not permitted for the treatment of lupus-related disease through Week 28. Subjects should not initiate any new ARB or ACE inhibitor therapy between randomization and Week 28. New or adjusted ARB or ACE inhibitor therapy is allowed beyond Week 28.

8.6. Topical Medications

Topical medications are permitted; however, topical compounds cannot include a prohibited medication. Topical ointments or creams of cyclosporine A are prohibited through Week 28; however ophthalmic use is permitted. Low potency topical steroids are allowed except on day of study visit. Medium to high potency topical corticosteroids are disallowed for all subjects through the 8-week safety follow-up, and high potency topical corticosteroids are not allowed during the study extension. For subjects in the cutaneous lupus substudy, topical treatment of target lesions should remain stable during the cutaneous lupus substudy period. For 72 hours prior to study visit, topical medications should not be applied to lesions under evaluation.

9. Study Evaluations

9.1. Study Procedures

9.1.1. Overview

The Time and Events Schedule summarizes the frequency and timing of efficacy, pharmacokinetics, antibodies to ustekinumab, pharmacodynamics, pharmacogenomics, health-related quality of life, safety, and other measurements applicable to this study.

Additional serum or urine pregnancy tests may be performed, as determined necessary by the investigator or required by local regulation, to establish the absence of pregnancy at any time during the subject's participation in the study.

The total blood volume to be collected from each subject over the course of the main portion of the study will be approximately 640 mL. The total blood volume to be collected in the study extension between Weeks 48 and 120 will be approximately 250 mL.

Repeat or unscheduled samples may be taken for safety reasons or for technical issues with the collection or analysis of specific samples.

A blood sample will be collected from subjects who have consented to participate in the pharmacogenomics component of the study. In the event of DNA extraction failure, a replacement pharmacogenomics blood sample may be requested from the subject. A separate informed consent would not be required to obtain a replacement sample.

Subjects who have consented to participate in the cutaneous lupus substudy will be requested to allow collection of skin biopsy samples at Week 0 and at Week 24. In addition, photographs will be taken of a target cutaneous lesion or area of active disease as noted in the Time and Events Schedule (Table 1). For additional detail regarding the cutaneous lupus substudy, refer to Section 9.7.

9.1.2. Screening Phase

9.1.2.1. Screening Procedures

Written informed consent must be obtained and reviewed by investigator before any screening data is collected.

Screening procedures will be performed as indicated in the Time and Events Schedule (Table 1). The screening visit must be performed no more than 6 weeks prior to the randomization visit (Week 0). In addition, to be eligible for study participation, subjects must have SLEDAI score 4 for clinical features at Week 0 and have received approval for study randomization following review and adjudication of screening lupus assessments by the Sponsor and/or Sponsor-selected independent reviewer(s).

Subjects will be trained on how to complete the Diary cards. Diary cards will be distributed to subjects for completion during the screening period.

Women of childbearing potential must have a negative serum β-hCG pregnancy test at screening and a negative urine β-hCG pregnancy test before randomization. Women of childbearing potential and men must consent to use highly effective methods of contraception (see inclusion criteria, Section 4.1) and continue to use contraception for the duration of the study and for 4 months after the last study agent administration. The method(s) of contraception used by each subject must be documented.

All screening evaluations establishing subject eligibility will be performed and reviewed by investigator before subject can be randomized. Although the SLICC criteria may not have been formally assessed, to be eligible for enrollment subjects must have demonstrated symptoms (documented in subject file) of SLE sufficient to meet SLICC criteria for a minimum of 3 months prior to first dose of study agent. Subjects eligible for enrollment in this study must qualify as having SLE by meeting the SLICC classification criteria for SLE based upon 1 or both of the following (as described in Inclusion Criterion #2):

- Meeting 4 criteria with at least 1 clinical criterion and at least 1 immunologic criterion, or
- A diagnosis of lupus nephritis with presence of at least 1 of the immunological variables, Subjects must also have 1 well-documented (subject file, referring physician letter, or laboratory result) medical historical value for unequivocally positive ANA, anti-dsDNA antibodies, and/or anti-Smith antibodies. Medical historical documentation of a positive test of ANA (e.g., ANA by HEp-2 titer, ANA by enzyme-linked immunosorbent assay) or anti-dsDNA (e.g., anti-dsDNA by Farr assay or ELISA) must include the date and type of the test, the testing laboratory name, numerical reference range, and a key that explains that the values provided are positive versus negative/equivocal or borderline. Only unequivocally positive values as defined in the laboratory's reference range are acceptable; borderline values will not be accepted.

In addition, in order to assess the stability of SLE disease activity, subjects must demonstrate SLEDAI-2K score ≥6, despite conventional treatment (e.g., immunomodulators, antimalarial drugs, corticosteroids, NSAIDs, anti-hypertensive drugs, and/or topical medications). In addition, subjects must have at least 1 positive autoantibody test (ANA, anti-dsDNA antibodies, and/or anti-Smith antibodies) observed during screening. Subjects must also demonstrate at least 1 BILAG A and/or 2 BILAG B domain scores observed prior to first administration of study agent.

9.1.2.2. Retesting

If a subject has signed the ICF and failed to meet at least 1 entry requirement, a one-time retest of screening laboratory test(s) will be allowed in the event of suspected error in sample collection or analysis performance, or a study entry procedure may be repeated once during the screening period if needed. A request to use a local test to replace the central lab test should be discussed with the medical monitor prior to retesting. This is inclusive of only 1 additional blood draw to be completed for retesting, regardless of whether an additional laboratory value is found to be out of range. The goal of the retest procedure is to assess if the subject is eligible for randomization within the screening window or should be screen failed. Subjects that have laboratory values that do not meet entry criteria following the retest or do not meet disease activity criteria following the repeat procedure are to be deemed a screen failure. Exceptions to this are positive QuantiFERON®-TB Gold, hepatitis C or B, or HIV tests; unless there is a suspected error in sample collection or analysis performance, these tests may not be repeated to meet eligibility criteria.

9.1.2.3. Rescreening

If a subject has failed screening and investigator wishes to rescreen the subject, this should be discussed with the study Sponsor and/or their designee. Only 1 rescreening is allowed per subject. Subjects who are rescreened will be assigned a new subject number, undergo the informed consent process, and then restart a new screening phase.

9.1.3. Double-Blind Treatment Phase

9.1.3.1. Week 0/Day of Randomization

At Week 0, eligible subjects will be randomly assigned by the IWRS in a 3:2 ratio to receive either ustekinumab or placebo in a blinded manner. Assessments will be performed as indicated in the Time and Events Schedule (Table 1). Subjects participating in the cutaneous lupus substudy will have baseline, pre-treatment photographs and/or skin biopsies collected. Subject's diary card which was distributed during screening will be reviewed at Week 0, and a new card will be provided at each study visit to record medication changes during the subsequent 4 weeks through the main portion of the study.

9.1.3.2. Placebo-Controlled Treatment Period (Through Week 24)

After randomization and the first administration of study agent by IV infusion, subjects will have blinded study agent administrations SC q8w through the Week 24 visit. Assessments will be performed as indicated in the Time and Events Schedule (Table 1).

9.1.4. Cross-Over Treatment (Through Week 40)

At Week 24, subjects in the placebo group will cross-over to receive ustekinumab dosing, and all subjects will continue to receive SC administrations q8w through Week 40. All subjects will continue to remain blinded to study treatment received during the placebo-controlled treatment period as described in Section 9.1.3.2.

9.1.5. Study Extension (Week 48/Week 56 Through Week 104)

Subjects who qualify for participation in the study extension through Week 104 will continue ustekinumab 90 mg q8w SC dosing at approximately 8 weeks (±2 weeks) after their Week 40 visit, or resume ustekinumab dosing at Week 56 with no more than 16 weeks (±2 weeks) since their Week 40 visit.

9.1.6. Subjects Withdrawing from Study Participation

Subjects who withdraw from study participation will not be required to return for any follow-up assessments.

9.1.7. Post-Treatment Safety Follow-Up

Subjects who permanently discontinue study agent at or before Week 40, or permanently discontinue at or before Week 104 if they are participating in the study extension, but do not withdraw from study participation, should be followed for approximately 16 weeks (5 half-lives) after the last study agent administration according to the visit schedule and assessments indicated in the appropriate Time and Events Schedules (Table 1 and Table 2). Follow-up visits should occur approximately 8 weeks and 16 weeks after the last study agent administration. Subjects who permanently discontinue study agent before or at Week 40 will not be eligible to participate in the study extension.

Telephone contact will be made to determine reasons for study discontinuation for up to 16 weeks after the last dose of study drug, unless the subject is lost to follow-up, or has withdrawn consent. If the information on reason for discontinuation is obtained via telephone contact, written documentation of the communication must be available for review in the source documents. If the subject has died, the date and cause of death will be collected and documented.

9.2. Efficacy

All efficacy evaluations should be consistently performed by the study investigator or sub-investigator to achieve comparable measures over time. Independent adjudication by Sponsor or Sponsor-designated independent reviewer(s) will be performed for key lupus assessments (e.g., SLEDAI, BILAG, and CLASI). These data will be reviewed at every visit that these data are collected and may require reconciliation of inconsistencies across assessments.

9.2.1. Evaluations

A complete list describing all efficacy evaluations and endpoints, and which evaluations are included in the composite endpoints is provided in Appendix 1.

9.2.1.1. SLEDAI-2K and S2K RI-50

The SLE disease activity index 2000 (SLEDAI-2K/S2K RI-50 [Baseline]) is an established, validated SLE activity index. It is based on the presence of 24 features in 9 organ systems and measures disease activity in SLE patients in the previous 30 days. It is weighted according to the feature. At screening, features are scored by the assessing physician if present within the last 30 days with more severe features having higher scores, and then simply added to determine the total SLEDAI-2K score, which ranges from 0 to 105.[33] At baseline, the features assessed in the SLEDAI-2K are used for comparison to the S2K RI-50 index described below.

The SLEDAI-2K has been adapted and developed into the SLEDAI-2K Responder Index (S2K RI-50 [Follow-up])[35], a measure that can document partial improvement in the 24 disease features between SLEDAI-2K assessments.[34] A threshold of 50% improvement was judged to reflect clinically significant improvement and is scored as half the weight for the feature. "When a descriptor is recorded as present at the initial visit, 1 of 3 situations can follow: (1) the descriptor achieves complete remission at follow-up, in which case the score would be "0"; (2) the descriptor does not achieve a minimum of 50% improvement at follow-up, in which case the score would be identical to its corresponding SLEDAI-2K value; or (3) the descriptor improves by ≥50% (according to the S2K RI-50 definition) but has not achieved complete remission, in which case the score is evaluated as one-half the score that would be assigned for SLEDAI-2K."[32] The S2K RI-50 score is the sum of the 24 scored items, which ranges from 0 to 105.

9.2.1.2. BILAG

The BILAG[13,17] index scores subjects based on the need for alterations or intensification of therapy. The assessing physician will evaluate 97 items divided into the following 9 organ/systems domains.
Constitutional
Mucocutaneous
Neuropsychiatric
Musculoskeletal
Cardiorespiratory
Gastrointestinal
Ophthalmic
Renal
Hematological
The assessing physician ought to consider each item as to its presence in the past 4 weeks, and answer 0=not present, 1=improving, 2=same, 3=worse, or 4=new as compared with a specified reference visit. Each organ/system domain is classified as BILAG A, B, C, D, or E based upon organ/system specific items and criteria specific to the domain.

9.2.1.3. CLASI

Cutaneous lupus erythematosus disease activity will be measured by the CLASI. The CLASI is an instrument the assessing physician will use to assess the disease activity and damage caused to the skin for CLE patients with or without systemic involvement. The CLASI consists of 2 scores; the first summarizes the activity of the disease while the second is a measure of the damage done by the disease. Activity is scored on the basis of erythema, scale/hyperkeratosis, mucous membrane involvement, acute hair loss and non-scarring alopecia. Damage is scored in terms of dyspigmentation and scarring, including scarring alopecia. The scores are calculated by simple addition based on the extent of the symptoms.[1] Higher activity and damage scores indicate worse disease activity.

9.2.1.4. Physician Global Assessment of Disease Activity

The physician must complete the Physician Global Assessment of Disease Activity[8] independent of subjects' assessment. The assessments will be recorded on a visual analogue scale (VAS; 0 to 10 cm). The scale for the assessment ranges from "no Lupus activity" (0) to 'extremely active Lupus" (10).

The physician assessor should preferably be the same person at every study visit for a given subject.

9.2.1.5. Patient Global Assessments

The subject must complete the Patient Global Assessment of Disease Activity and Patient's Assessment of Pain independent of the Physician's Global Assessment of Disease Activity.

9.2.1.5.1 Patient Global Assessment of Disease Activity

The Global Assessment of Disease Activity will be recorded on a visual analogue scale (VAS; 0 to 10 cm). The scale for the assessment ranges from "very well" (0) to "very poor" (10).

9.2.1.5.2. Patient Assessment of Pain

The Patient's Assessment of Pain is used to assess the patient reported pain intensity. The patient's will be asked to assess their average pain during the past week on a visual analogue scale (VAS; 0 to 10 cm). The anchors of the instrument include 0 to represent 'no pain' and 10 to represent 'the worst possible pain'.

9.2.1.6. Short-Form-36

The RAND short-form (SF)-36 questionnaire is a self-administered multi-domain scale with 36 items. Eight health domains cover a range of functioning:
Limitations in physical function
Limitations in usual role activities
Bodily pain
General mental health (psychological distress and well-being)
Vitality (energy and fatigue)
Limitations in social functioning due to physical or mental health problems
Limitations in usual role activities due to personal or emotional problems
General health perception The subscales are scored from 0 to 100. The scoring yields a Physical Component Summary score and a Mental Component Summary score, a total score, and subscale scores. Higher scores represent better outcomes. It is appropriate for persons over the age of 14 and may be completed in 5 to 10 minutes. Translations are available in most languages; the instrument has undergone extensive linguistic and cultural validation. Version 2 acute will be used in the study.

The concepts measured by the SF-36 are not specific to any age, disease, or treatment group, allowing comparison of relative burden of different diseases and the benefit of different treatments.[42] A change of 3 points in any of the subscales or 5 points for the component score is associated with clinically meaningful change.[27,41,40] The SF-36 has been used extensively in clinical trials providing evidence of psychometric properties. Reliability estimates for physical and mental component summary scores exceeded 0.90 in early studies[21] and have been further confirmed in later studies. Construct validation was established through comparison to several other generic health surveys.

9.2.1.7. Fatigue Severity Scale

The Fatigue Severity Scale (FSS) is a 9-item questionnaire designed to assess the severity of fatigue and its impact on daily living using 7 response options (1=Completely Disagree, 7=Completely Agree) during a recall period of the past week. It can be completed within 5 minutes by the subject. Scores above 36 of the total possible score of 63 reflect increasing severity of fatigue. The scale was developed for use in SLE.[19] The scores on the scale correlate with patient reported pain, sleep, depression, and with each subscale of the SF-36. The FSS has shown a high internal consistency, and differentiates patients from controls in studies with SLE subjects. The instrument was translated from the original English version and is available in several languages.

9.2.2. Definitions

A complete list describing all efficacy evaluations and endpoints, and which evaluations are included in the composite endpoints is provided in Appendix 1.

9.2.2.1. SRI-4

Systemic Lupus Erythematosus Disease Activity Index 2000 SRI-4 response is defined as a composite endpoint requiring at least a 4 point reduction in SLEDAI 2K score (Section 9.2.1.1), no worsening (<10 mm increase) from baseline in the Physician's Global Assessment of Disease Activity score (PGA) (Section 9.2.1.4), and no new BILAG Domain A and no more than 1 new BILAG Domain B scores (Section 9.2.1.2).[9] SRI-5 and SRI-6 are similarly defined with response requiring a ≥5 point reduction or ≥6 point reduction in SLEDAI 2K, respectively. SRI-5 and SRI-6 are similarly defined with response requiring a ≥5 point reduction or ≥6 point reduction in SLEDAI-2K, respectively.

9.2.2.2. BILAG-based Combined Lupus Assessment

The BILAG-based Combined Lupus Assessment (BICLA) requires patients to meet response criteria across 3 assessment tools: (1) the BILAG-2004 index (2) the SLEDAI index and (3) a PGA. Patients are identified as responders or non-responders based upon the following requirements:[39]

| | Requirements for BICLA Response |
|---|---|
| BILAG | BILAG improvement classified as: All BILAG A scores at baseline improved to either BILAG B, C or D All BILAG B scores at baseline improved to either BILAG C or D No worsening in disease activity defined as no new BILAG A scores and ≤1 new BILAG B score |
| SLEDAI-2K | No worsening of total SLEDAI-2K from baseline (change ≤0) |
| PGA | No significant deterioration (<10 mm increase) in 100 mm visual analogue PGA |
| Treatment Failure | No treatment failure (see SAP for definition of treatment failure) |

9.2.2.3. Flares

Flares for this study will be defined as:
SLEDAI Flare: At least a 4+ point increase in SLEDAI-2K score (includes severe flares)
Severe SLEDAI flare: At least a 7+ point increase in SLEDAI-2K score
BILAG flare: At least 1 new BILAG A or 2 new BILAG B scores (from scores <B)

9.2.2.4. S2K RI-50 Response

S2K RI-50 response is defined as a decrease of at least 6 points from baseline in the SLEDAI-2K score.

9.2.2.5. No Worsening in PGA

No worsening in PGA is defined as less than a 10 mm increase on 100 mm VAS.

9.2.3. Endpoints

Primary Endpoint

The primary endpoint of this study is the proportion of subjects with a composite SRI-4 response at Week 24.

Major Secondary Endpoints

The major secondary endpoints are listed in order of importance as specified below:
1. The change from baseline in SLEDAI-2K at Week 24.
2. The change from baseline in PGA at Week 24.
3. The proportion of subjects with BICLA response at Week 24.

Other Endpoints

Flares

4. Time to first flare (SLEDAI flare, Severe SLEDAI flare, BILAG flare) from Week 12 through Week 24 and from Week 24 through Main Study 8-week Safety Follow-up Visit/Week 48 as well as from Week 48 through Week 104.
5. Number of flare (SLEDAI flare, Severe SLEDAI flare, BILAG flare) free visits from Week 12 through Week 24 and from Week 24 through Main Study 8-week Safety Follow-up Visit/Week 48 as well as from Week 48 through Week 104.

SLE Disease Activity

6. The proportion of subjects with responses in SRI-4, SRI-5, SRI-6, S2K RI-50 response and BICLA over time.
7. The proportion of subjects with no worsening in SLEDAI, BILAG, PGA, and Patient's Global Assessment of Disease Activity (PtGA) over time.
8. The proportion of subjects with improvement in SLEDAI (4, 5, and 6, points), BILAG, and PGA over time.
9. The absolute change from baseline in SLEDAI-2K, S2K RI-50, PGA over time.
10. The percent change in serological activity (e.g., ANA, anti-dsDNA, other autoantibodies, C3, C4) or SLEDAI feature measurements over time.
11. Shift table of BILAG by organ domain over time.
12. The percent change in CLASI scores (activity and damage) in subjects with cutaneous disease over time.

PRO Outcomes

13. The change in patient reported outcomes (PROs) (Pain VAS scale, FSS, SF-36 physical and mental component summary scores and individual domains) over time.
14. The proportion of subjects with clinically (the minimally clinical important difference) in PROs (i.e., FSS, improvement in SF-36) over time.
15. The change from baseline in PtGA at Week 24.

Medications

16. The proportion of subjects with meaningful changes in selected SLE medications from Week 12 through Main Study 8-week Safety Follow-up Visit/Week 48.
17. Change in corticosteroid dose from Week 48 through Week 104 for subjects who participate in the study extension.

Development and analyses of the new endpoint(s) will be included in a separated technical report.

9.3. Pharmacokinetics and Immunogenicity

Serum samples will be used to evaluate the pharmacokinetics (PK) of ustekinumab, as well as the immunogenicity of ustekinumab (antibodies to ustekinumab). Serum collected for PK and immunogenicity analyses may additionally be used to evaluate safety or efficacy aspects that address concerns arising during or after the study period. Genetic analyses will not be performed on these serum samples. Subject confidentiality will be maintained.

9.3.1. Serum Collection and Handling

Venous blood samples will be collected at the time points shown in the Time and Events Schedule for the determination of serum ustekinumab concentrations and antibodies to ustekinumab. Serum samples will also be collected at the final visit from subjects who terminate study participation early. At visits where PK and immunogenicity will be evaluated, 1 blood draw of sufficient volume can be used. Each sample will be split into 3 aliquots (1 aliquot for serum ustekinumab concentration, 1 aliquot for antibodies to ustekinumab, and 1 aliquot as a back-up). Samples must be collected before study drug administration at visits when study drug administration is scheduled. The exact dates and times of blood sample collection must be recorded in the laboratory requisition form.

9.3.2. Analytical Procedures

Serum samples will be analyzed to determine ustekinumab concentrations using a validated, specific, and sensitive immunoassay method by Sponsor's bioanalytical facility or under the supervision of the Sponsor. The Sponsor, or its designee, under conditions in which the subjects' identity remains blinded, will assay these samples.

9.3.3. Immunogenicity Assessments

Antibodies to ustekinumab will be detected using a validated immunoassay method in serum samples collected from all subjects. Serum samples that test positive for antibodies to ustekinumab will be further characterized to determine if antibodies to ustekinumab could neutralize the biological effects of ustekinumab in vitro (i.e., neutralizing antibodies [NAbs] to ustekinumab). All samples will be tested by the Sponsor or Sponsor's designee.

9.4. Biomarkers

The collection, preparation, storage and shipment of skin biopsies, blood, serum and urine are detailed in the Time and Events schedule (Table 1) and the Laboratory Manual. Biomarkers may include, but are not limited to, inflammatory markers, RNA, cell surface markers, auto-antibodies, T cell and B cell repertoire, target specific markers, and other categories of biomarkers potentially involved in the development and the progression of lupus.

Serum Analyses

Serum will be analyzed for levels of specific proteins including but not limited to soluble CD40 ligand (sCD154), interleukin (IL)-6, IL-12p40, IL-17, IL-21, IL-22, IL-23p19, C-X-C motif chemokine 10 (CXCL10), BAFF, interferons, auto-antibodies and other inflammation-related molecules.

Urine Samples

Urine samples will be evaluated for excreted proteins or other markers believed to have relevance in SLE.

Skin Biopsy Analyses

Skin biopsies will be utilized for cellular, molecular, and gene expression analyses.

Whole Blood Gene Expression Analyses

Whole blood will be collected from all subjects for RNA, flow cytometry (samples from selected sites will be analyzed at central laboratory or other analytical laboratory), T cell and B cell repertoire (nucleic acid analyses [RNA and DNA] for specific T and B cell receptors only) and epigenetics analysis (e.g., DNA methylation).

9.5. Pharmacogenomic Evaluations

The DNA samples will be used for research related to this study (CNTO1275SLE2001). Specific genomic testing will be undertaken for consenting subjects (subjects participating in this portion of the study must sign a separate ICF). The procedure will involve taking a blood sample that may be analyzed for specific target genes that may play a role in lupus. Any genomic assessments will be performed in strict adherence to current subject confidentiality standards for genetic testing. Refusal to participate in genomics testing will not result in ineligibility for participation in the rest of the clinical study.

9.6. Serologic Markers

Sample for autoantibodies (including ANA, anti-dsDNA, anti-Smith), complement C3, C4, and other analytes will be collected as described in the Table of Events (Table 1) and Section 9.8 Safety Evaluations (Clinical Laboratory Tests).

9.7. Cutaneous Lupus Substudy

Subjects with cutaneous disease will be evaluated using CLASI scoring. Additionally, subjects with cutaneous disease who consent to participate in the cutaneous lupus substudy will have additional assessments including collection of skin biopsies (optional consent) prior to study agent administration at Week 0 and at Week 24 and/or photographs of a cutaneous lesion or an area of active disease (optional consent) to be performed as shown in the Table of Events (Table 1). There will not be any restrictions on the number of subjects with cutaneous disease who can enroll into either the main study or the cutaneous lupus substudy.

Subjects who consent to the optional biopsy collection will have 2 skin biopsies (4 mm) excised from an active target lesion at Week 0, followed by 2 additional biopsies of the same lesion (regardless of cutaneous disease activity) at Week 24 (Cutaneous Lupus Substudy Manual). Skin biopsies will be utilized for cellular, molecular, and gene expression analyses.

Independent of cutaneous biopsy collection, subjects who participate in the cutaneous lupus substudy will be requested to provide consent for photographs to be collected from an identified cutaneous lesion or an area of active disease. Consenting subjects with cutaneous lupus unsuitable for biopsy (e.g., malar rash or alopecia) may be evaluated by photography. The photographs are for exploratory purposes only. The photographs will be used to assist in a qualitative evaluation of clinical response. The photographs and skin biopsies can target a different area of active disease, but the follow-up photographs or biopsies should re-evaluate the same area of active disease as originally assessed at week 0. Confidentiality of the subjects involved in this study will be maintained; specifically photographs of subjects in this study will not be published or otherwise made public without blocking adequate portions of the subject's face or body so that the individual cannot be identified.

9.8. Safety Evaluations

Safety assessments include vital signs, general physical examinations and skin evaluations (assessed during S2K RI-50 and CLASI evaluations), adverse events, concomitant medication review, pregnancy testing (refer to Section 12.3.3), administration reactions, chemistry and hematology laboratory tests, and antibodies to ustekinumab. Chest x-ray and TB, HIV, hepatitis B, and hepatitis C testing will be required at time of screening (Table 1).

Refer to Section 4.1 for tuberculosis screening criteria. Subject diary cards will be used to capture medication changes that occur in between study visits through the main portion of the study.

Any clinically significant abnormalities persisting at the end of the study will be followed by the investigator until resolution or until a clinically stable endpoint is reached.

The study will include the following evaluations of safety and tolerability according to the time points provided in Table 1 and Table 2 for the extended study.

Adverse Events

Adverse events (AE) will be reported by the subject (or, when appropriate, by a caregiver) for the duration of the study, and will be followed by the investigator.

Infections

Subjects will be provided an alert card of signs and symptoms for infections, and will be instructed to contact the site between scheduled visits should any signs and symptoms occur. At each site visit, investigators or other site personnel are required to evaluate subjects for any signs or symptoms of infection, and ask about symptoms of infection or other AEs that may have occurred in between site visits.

Study agent should not be administered to a subject with a clinically important, active infection. Treatment with study agent should be withheld until serious and/or severe infections are completely resolved. If a subject develops a serious or severe infection, including but not limited to sepsis or pneumonia, discontinuation of study treatment must be considered. Treatment must be permanently discontinued for subjects who develop an opportunistic infection. For active varicella-zoster infection or a significant exposure to varicella zoster infection in a subject without history of chickenpox, the subject should be evaluated for symptoms of infection and if the subject has received appropriate treatment and/or recovered or no symptoms of infection, may continue study administration after discussion with the study Sponsor.

Clinical Laboratory Tests

Blood samples for serum chemistry and hematology will be collected according to the Time and Events Schedule (Table 1 and Table 2 for the extended study). The investigator must review the laboratory report immediately upon availability, document this review, and record any clinically relevant changes occurring during the study. Coomb's direct test, urine dipstick, urine sediment microscopy and urine pregnancy test will be performed by site staff or the local laboratory. With the approval of the study Sponsor, the use of local laboratories may also be allowed in cases where initiation of treatment or safety follow-up is time-critical and the central laboratory results are not expected to be available before the need to provide study agent treatment or if actions need to be taken for safety reasons.

A one-time retest of screening laboratory test(s) analyzed by the central laboratory will be allowed in the event of suspected error in sample collection or analysis performance.

Hematology Panel
  hemoglobin
  hematocrit
  white blood cell (WBC) count with differential (basophils, eosinophils, lymphocytes, monocytes, neutrophils)
  platelet count
  CD 19 B-cell analyses during screening only if needed for subjects previously exposed to B-cell depleting therapies (Section 4.1.3)
  Coomb's direct test (local laboratories, if available)
Serology Laboratory
  Ig isotype profile (IgG, IgM, IgA levels)
  C3 and C4 Complement
  ANA
  anti-dsDNA
  anti-phospholipid antibodies including lupus anticoagulant, anti-cardiolipin, and anti-$\beta_2$-glycoprotein-I antibodies
  other autoantibodies including anti-Smith, anti-Sjögren's-syndrome-related antigen A (SSA [anti-Ro], and B (SSB [anti-La]), anti-ribonucleoprotein (anti-RNP)
Coagulation Labs
  Prothrombin Time
  Partial Thromboplastin Time
  International Normalized Ratio

| Serum Chemistry Panel | |
|---|---|
| sodium | alkaline phosphatase |
| potassium | calcium |
| chloride | phosphorous |
| bicarbonate | albumin |
| blood urea nitrogen | total protein |
| creatinine | creatinine kinase |
| glucose | aspartate aminotransferase |
| aldolase (if creatine kinase is elevated at screening then aldolase test at Week 0 and follow-up as needed) | alanine aminotransferase total bilirubin, and if total bilirubin is abnormally elevated, then direct bilirubin, and indirect bilirubin |

Urine Analyses—Fresh spot urine
  Urinalysis using urine dipstick. Urine sample will be further analyzed at
  Central laboratory.
  Urinary protein/creatinine ratio[9] will be analyzed at the central laboratory using an aliquot of spot urine collected from subjects.
  Urine Sediment Microscopy (Local Laboratory Assessment using spot urine samples)
  Red blood cells
  WBC, with note if urinary tract infection is present/absent
  epithelial cells
  crystals
  Red blood cells, WBC, or heme-granular casts
  bacteria
Serum and urine pregnancy testing for women of childbearing potential only
Viral serology (HIV antibody, HBsAg, anti-HBs, anti-HBc total, and hepatitis C virus antibody)

Vital Signs

Weight and temperature will be assessed. Blood pressure and heart rate measurements will be assessed.

Physical Examination

A full body physical examination will be performed pre-treatment and during the study as shown in Table 1 and Table 2 for the extended study.

9.9. Sample Collection and Handling

The actual dates and times of sample collection must be recorded on the laboratory requisition form.

Refer to the Time and Events Schedule (Table 1 and Table 2 for the extended study) for the timing and frequency of all sample collections.

Instructions for the collection, handling, and shipment of samples are found in the laboratory manual that will be provided for sample collection and handling.

10. Subject Completion/Withdrawal 10.1. Completion

A subject who does not enter into the study extension will be considered to have completed the main study if he or she has completed assessments through 16-week safety follow-up of the main study. A subject who has enrolled into the study extension will be considered to have completed the main portion of this study if he or she has completed assessments through the 8-week safety follow-up visit of the main study. Subjects who prematurely discontinue study treatment for any reason before the Week 8 or Week 16 safety follow-up visits (from the main study), will not be considered to have completed the main portion of the study. A subject who has enrolled into the study extension will be considered to have completed the study extension if he or she has completed assessments through Week 120.

Discontinuation of Study Treatment

If a subject's study treatment must be discontinued before or at Week 40 (for subjects who do not participate in the study extension) or before Week 104 (for subjects who do participate in the study extension), this will not result in automatic withdrawal of the subject from the study and follow-up assessments should be obtained approximately 8 and 16 weeks following the last dose of study agent.

A subject's study treatment must be permanently discontinued if any of the following occur:
1. An AE temporally associated with study agent infusion or injection, resulting in bronchospasm with wheezing and/or dyspnea requiring ventilatory support, or symptomatic hypotension with a greater than 40 mm Hg decrease in systolic blood pressure.
2. The subject withdraws consent for administration of study agent.
3. Pregnancy or planning to become pregnant within the study period or within 16 weeks after the last study agent injection.
4. The initiation of prohibited medications or treatments (as per Section 4.3).
5. Malignancy, with the exception of no more than 2 localized basal cell skin cancers that are treated with no evidence of recurrence or residual disease.
6. An opportunistic infection.
7. The investigator or Sponsor's medical monitor deems it is in the subject's best interest.
8. The subject is deemed ineligible according to the following TB criteria:

A diagnosis of active TB is made.

A subject has symptoms suggestive of active TB based on follow-up assessment questions and/or physical examination, or has had recent close contact with a person with active TB, and cannot or will not continue to undergo additional evaluation.

A subject undergoing continued screening has a chest radiograph with evidence of current active TB and/or a positive QuantiFERON®-TB Gold test and/or a positive tuberculin skin test result in countries in which the QuantiFERON®-TB Gold is not approved/registered result and/or an indeterminate QuantiFERON®-TB Gold test result on repeat testing, unless active TB can be ruled out and appropriate treatment for latent TB can be initiated either prior to or simultaneously with the next administration of study agent and continued to completion.

A subject receiving treatment for latent TB discontinues this treatment prematurely or is noncompliant with the therapy.

9. Significant worsening of SLE disease activity from baseline or having high disease activity for 2 or more consecutive visits starting at Week 16 based on overall clinical assessments; or if a subject requires the addition of a new immunomodulator to the existing treatment regimen after Week 16.

In addition, permanent discontinuation of study agent treatment must be considered for subjects who:

Receive an increase (relative to baseline) in their immunomodulator dose.

Develop any of the following adverse events that are reported as serious or severe: study agent infusion reaction, injection-site reaction, or infection.

10.3. Withdrawal from the Study

A subject will be withdrawn from the study for any of the following reasons:
Lost to follow-up
Withdrawal of consent
Death If a subject is lost to follow-up, every reasonable effort must be made by the study site personnel to contact the subject and determine the reason for discontinuation/withdrawal. The measures taken to follow-up must be documented.

When a subject withdraws before completing the study, the reason for withdrawal is to be documented. Study drug assigned to the withdrawn subject may not be assigned to another subject. Subjects who withdraw from this study will not be replaced.

A subject who withdraws from the study will have the following options regarding the optional research samples:
The collected samples will be retained and used in accordance with the subject's original informed consent for optional research samples.

The subject may withdraw consent for optional research samples, in which case the samples will be destroyed and no further testing will take place. To initiate the sample destruction process, the investigator must notify the Sponsor study site contact (or appropriate designee) of withdrawal of consent for the optional research samples and to request sample destruction. The Sponsor study site contact will, in turn, contact the biomarker representative to execute sample destruction. If requested, the investigator will receive written confirmation from the Sponsor that the samples have been destroyed.

Withdrawal from the Optional Research Samples While Remaining in the Main Study The subject may withdraw consent for optional research samples while remaining in the study. In such a case, the optional research samples will be destroyed. The sample destruction process will proceed as described above.

Withdrawal from the Use of Samples in Future Research

The subject may withdraw consent for use of samples for research (refer to Section 16.2.5, Long-Term Retention of Samples for Additional Future Research). In such a case, samples will be destroyed after they are no longer needed for the clinical study. Details of the sample retention for research are presented in the main ICF and in the separate ICF for optional research samples.

11. Statistical Methods

Statistical analysis will be done by the Sponsor or under the authority of the Sponsor. A general description of the statistical methods to be used to analyze the efficacy and safety data is outlined below. Specific details will be provided in the Statistical Analysis Plan.

11.1. Subject Information

For all subjects who receive at least 1 dose of study drug descriptive statistics will be provided for demographic data and baseline characteristics, including prior and background SLE therapies. All subjects who are randomized and received at least 1 dose of study agent will be included in the efficacy analyses according to their assigned treatment group. The safety analysis population will include those subjects who received at least 1 dose of study agent, and will be analyzed according to the actual study agent received.

11.2. Sample Size Determination

The sample size calculation is based upon the primary endpoint, proportion of SRI-4 responders at Week 24. Approximately 60 subjects treated with ustekinumab and approximately 40 subjects with placebo is projected to give approximately 80% power to detect a significant difference in response rate compared with placebo (assume 35% and 60% response rates in placebo and ustekinumab respectively, which translates to 25% absolute increase over placebo or an odds ratio of 2.79) with an alpha level of 0.1. The assumption of a 35% responder rate for placebo is based upon a previous study in which a similar SLE population was treated.[36] Recent studies have shown very high placebo rates in certain regions, thus the power for the study could be reduced.[14]

The power to detect a significant treatment difference at $\alpha=0.1$ (2-sided) is calculated under various assumptions (see Table 4).

TABLE 4

Power to Detect a Significant Treatment Difference in the Proportion of Subjects with SRI-4 Response at Week 24

| Proportion of Placebo Group with Response (%) | Absolute Increase in Response (%) | Proportion of Ustekinumab Group with Response (%) | Odds Ratio | Power |
| --- | --- | --- | --- | --- |
| 20 | 20 | 40 | 2.67 | 70% |
|    | 25 | 45 | 3.27 | 85% |
|    | 30 | 50 | 4.00 | 94% |
| 25 | 20 | 45 | 2.45 | 67% |
|    | 25 | 50 | 3.00 | 82% |
|    | 30 | 55 | 3.67 | 92% |
| 30 | 20 | 50 | 2.33 | 64% |
|    | 25 | 55 | 2.85 | 80% |
|    | 30 | 60 | 3.50 | 91% |
| 35 | 20 | 55 | 2.27 | 62% |
|    | 25 | 60 | 2.79 | 79% |
|    | 30 | 65 | 3.45 | 91% |
| 40 | 20 | 60 | 2.25 | 62% |
|    | 25 | 65 | 2.79 | 79% |
|    | 30 | 70 | 3.50 | 91% |

*Note:
SRI-4 response is defined as a ≥4-point reduction in SLEDAI-2K score, no new domain scores in either BILAG A or BILAG B and no worsening (<10 mm increase) from baseline in the PGA.[10]

11.3. Efficacy Analyses

All efficacy analyses will be performed on the modified intent-to-treat (mITT) analysis set. The mITT analysis set will include all subjects who are randomized and received at least 1 dose of study agent. The efficacy analyses will be calculated according to their assigned treatment group.

11.3.1. Primary Endpoint Analysis

The primary endpoint of this study is the proportion of subjects with a composite measure of SLE disease activity (SRI-4 response) at Week 24 (Section 9.2.2.1). The primary analysis will be based upon the primary endpoint and will be conducted on the mITT population, which includes all randomized subjects who receive at least 1 dose of study agent, have at least 1 measurement prior to the administration, and have at least 1 post-baseline SRI-4 measurement.

Last observation carried forward procedure will be used to impute the missing SRI-4 component if the subjects have data for at least 1 SRI-4 component at Week 24. If the subjects do not have data for any SRI components at Week 24, the subjects will be considered not to have achieved the SRI-4 response. In addition, subjects who meet any 1 of the following criteria will be considered to have not achieved the primary endpoint, SRI-4 response at Week 24 (full details will be provided in the SAP):

- Between the Week 12 visit and the Week 24 visit, either the dose of an immunomodulator is higher than at baseline, or a new immunomodulator has been added to the existing treatment regimen.
- The addition of a new immunomodulator to the existing treatment regimen before Week 12 and subject still was receiving that immunomodulator after Week 12.
- Initiate treatment with disallowed dose or disallowed use of oral, IV or IM or other type of corticosteroid administration for SLE, or increase the dose of oral corticosteroids for SLE above baseline between the Week 12 and 24 visits.
- Subjects who were not receiving ARB or ACE inhibitor therapy who then initiated a new ARB or ACE inhibitor therapy between Week 12 and Week 24. Subjects who substitute an ARB or ACE inhibitor for a comparable medication would not be considered treatment failures.

Discontinue study agent due to lack of efficacy for an AE of worsening of SLE prior to Week 24.

For subjects who use systemic corticosteroids for another indication, the efficacy measurement will be carried forward from the last observation prior to the initiation of the treatment, for the period of 2 weeks after initiation of the treatment. After the 2 week period, the subject's calculated value will be as measured.

Other situations may confound the primary endpoint, such as a subject initiating NSAIDs after Week 16, or using epidural, IV, IM, IA, or intra-lesional, inhaled corticosteroids, and topical medication. Data handling rules will be specified in the Statistical Analysis Plan.

Logistic regression, adjusting for baseline stratifications and baseline SLEDAI, will be used to analyze the primary endpoint. The baseline SLEDAI value is defined as the closest non-missing measurement taken prior to the Week 0 infusion. If significant non-normality is observed, appropriate nonparametric tests will be used to evaluate the differences between treatments.

The study will be considered positive if the primary analysis achieves statistical significance at a significance level of 0.1 (2-sided) and ustekinumab shows a positive treatment effect relative to placebo treatment.

In addition to the primary analysis, sensitivity analyses will be performed to explore the effects with different data handling rules. If it is deemed necessary, the primary endpoint will be analyzed on the per protocol population. Details of the inclusion/exclusion rules for per protocol population will be provided in the SAP.

Subgroup analysis based on region will be performed. This is due to potential regional differences in evaluating efficacy, and high placebo response rates in certain regions. Subgroup analysis of the primary endpoint by other selected baseline characteristics will be presented. Details will be outlined in the SAP.

11.3.2. Major Secondary Analyses

The change from baseline in SLEDAI-2K at Week 24.
The change from baseline in PGA at Week 24.
The proportion of subjects with BICLA response at Week 24.

Continuous responses will be analyzed using an analysis of covariance model with treatment group as a fixed factor and baseline stratifications (e.g., regions) as a covariate. Nonparametric methods will be adopted when the normality assumption is violated.

11.3.3. Other Planned Efficacy Analyses

For the other efficacy endpoints listed in Section 9.2.3, the following statistical methods will be applied:

Binary data will be analyzed using the same statistical method as in the primary efficacy analysis. Continuous responses will be analyzed using an analysis of covariance model with treatment group as a fixed factor and baseline stratifications (e.g., regions) as a covariate. Nonparametric methods will be adopted when the normality assumption is violated. Log-rank tests will be used to compare endpoints defined by time to an event.

11.3.4. Efficacy Analyses in the Study Extension

Long-term evaluations of efficacy including SRI-4, SLE-DAI-2K, PGA, reduction in corticosteroid dosing, and evaluations of flare over time will also be performed for those subjects who participate in the study extension.

11.4. Interim Analyses

Interim analyses (IA) will be conducted when approximately ⅓ and ⅔ of subjects reach Week 24. In the first IA, only evidence for notable efficacy will be assessed. In the second IA, evidence for notable efficacy as well as treatment futility will be analyzed. Variations in placebo effect across regions will be incorporated into the interim analyses. Details concerning the IAs are described in the IA Statistical Analysis Plan.

11.5. Pharmacokinetic Analyses

Serum ustekinumab concentrations will be summarized for each treatment group over time. Descriptive statistics, including arithmetic mean, standard deviation, median, interquartile range, minimum, and maximum will be calculated at each sampling time point.

If feasible, a population PK analysis using nonlinear mixed effects modeling may be used to characterize the disposition characteristics of ustekinumab in the current study. The influence of important variables such as body weight and antibodies to ustekinumab status on the population PK parameter estimates may be evaluated. Details will be given in a population PK analysis plan, and results of the population PK analysis will be presented in a separate technical report.

11.6. Immunogenicity Analyses

The incidence and titers of antibodies to ustekinumab will be summarized for subjects who received at least 1 administration of ustekinumab and have appropriate samples for detection of antibodies to ustekinumab (i.e., subjects with at least 1 sample obtained after their first dose of ustekinumab).

The incidence of NAbs to ustekinumab will be summarized for subjects who are positive for antibodies to ustekinumab and have samples evaluable for NAbs.

11.7. Biomarker Analyses

The following results from treated and untreated SLE subjects will be summarized:
The concentration of individual serum and urine markers.
Results from selected biomarkers in skin biopsy tissue by RNA-sequencing and immunohistochemistry.
Results from whole blood gene expression profiling, flow cytometry, T cell and B cell repertoire, and epigenetics.
Additional exploratory analyses may be performed following evaluation of the data.

The samples collected from other ongoing clinical studies may also be included in the biomarker data analyses. Results of biomarker analyses may be presented in a separate report.

11.8. Pharmacogenetics Analyses

The DNA research may consist of the analysis of 1 or more candidate genes or of the analysis of genetic markers throughout the genome (as appropriate) in relation to this study.

Results of genomic analyses will be presented in a separate report once the overall number of samples including those collected from other sources is appropriate.

11.9. Pharmacokinetic and Pharmacodynamic Analysis

If data permit, the relationships between serum ustekinumab concentration and efficacy or pharmacodynamic measures may be analyzed graphically.

11.10. Safety Analyses

Safety analyses will be based on the population of subjects who received at least 1 dose of either study agent; subjects will be summarized by the treatment they actually received.

Adverse Events (AEs)

The verbatim terms used to identify AEs will be coded using the Medical Dictionary for Regulatory Activities. All reported AEs with onset during the treatment phase (i.e., treatment-emergent AEs, and AEs that have worsened since baseline) will be included in the analysis. For each AE, the percentage of subjects who experience at least 1 occurrence of the given event will be summarized by treatment group. Routine safety evaluations will be performed. Adverse events, serious AEs (SAEs), reasonably related AEs, and AEs by severity will be summarized by treatment group.

The incidence and types of infections, infusion reaction, and inject site reactions will be analyzed for this study. An infusion reaction is defined as an AE that occurs during or within 1 hour following the infusion of study agent, with the exception of laboratory abnormalities.

Special attention will be given to those subjects who died, or who discontinued treatment due to an adverse event, or who experienced a severe or a serious adverse event (e.g., summaries, listings, and narrative preparation may be provided, as appropriate).

Clinical Laboratory Tests

Laboratory data will be summarized by the type of laboratory test. Reference ranges and Common Terminology Criteria for Adverse Events (CTCAE) will be used in the summary of laboratory data. Descriptive statistics will be calculated for each laboratory analyte at baseline and at each scheduled time point. Changes from baseline results will be presented in pre-versus post-treatment cross-tabulations (with classes for below, within, and above normal ranges based on laboratory reference ranges). The baseline is defined as the last measurement prior to the first dose of the randomized treatment. The number and percentage of subjects by Maximum CTCAE Grade will be summarized for each treatment group for each laboratory analyte. The laboratory parameters and change from baseline in selected laboratory parameters (hematology and chemistry), and the number of subjects with abnormal laboratory parameters (hematology and chemistry) based on CTCAE toxicity grading will be summarized treatment group. Listings of SAEs will also be provided. All safety analyses will be based on the population of subjects who received at least 1 dose of either study agent; subjects will be summarized by the treatment they actually received.

Urine protein and creatinine measurements will be used to calculate the urine protein to creatinine ratio. Descriptive statistics will be calculated for these ratios at baseline and at each scheduled time point.

Vital Signs

Vital sign measures at each scheduled time point and their changes from baseline will be summarized using descriptive statistics. The baseline is defined as the last measurement prior to the first dose of the randomized treatment.

11.11. Data Monitoring Committee

An independent DMC will be established to monitor data on an ongoing basis to ensure the continuing safety of the subjects enrolled in this study and to conduct interim efficacy analysis. The committee will meet at least twice to review interim data, including when ⅓ and ⅔ of subjects reach Week 24. After each review, the DMC will make a recommendation to the Sponsor committee whether the study should be stopped for safety concerns. In the first IA, Sponsor will also be notified for notable efficacy in order to advance to next trial. In the second IA, Sponsor will be notified for notable efficacy as well as futility. The details will be provided in a separate DMC charter and in the IA Statistical Plan.

The DMC will have 3 to 6 members who are independent of the Sponsor. The DMC will consist of at least 1 medical expert in the relevant therapeutic area and at least 1 statistician. The DMC responsibilities, authorities, and procedures will be documented in its charter.

The DMC will no longer be active after the assessment of the primary endpoint in this study.

12. Adverse Event Reporting

Timely, accurate, and complete reporting and analysis of safety information from clinical studies are crucial for the protection of subjects, investigators, and the Sponsor, and are mandated by regulatory agencies worldwide. The Sponsor has established Standard Operating Procedures in conformity with regulatory requirements worldwide to ensure appropriate reporting of safety information; all clinical studies conducted by the Sponsor or its affiliates will be conducted in accordance with those procedures.

12.1. Definitions

12.1.1. Adverse Event Definitions and Classifications

Adverse Event

An adverse event is any untoward medical occurrence in a clinical study subject administered a medicinal (investigational or non-investigational) product. An adverse event does not necessarily have a causal relationship with the treatment. An adverse event can therefore be any unfavorable and unintended sign (including an abnormal finding), symptom, or disease temporally associated with the use of a medicinal (investigational or non-investigational) product, whether or not related to that medicinal (investigational or non-investigational) product. (Definition per International Conference on Harmonisation [ICH])

This includes any occurrence that is new in onset or aggravated in severity or frequency from the baseline condition, or abnormal results of diagnostic procedures, including laboratory test abnormalities.

Note: The Sponsor collects adverse events starting with the signing of the ICF (refer to Section 12.3.1, All Adverse Events, for time of last adverse event recording).

Serious Adverse Event

A serious adverse event based on ICH and EU Guidelines on Pharmacovigilance for Medicinal Products for Human Use is any untoward medical occurrence that at any dose:

Results in death
Is life-threatening
(The subject was at risk of death at the time of the event. It does not refer to an event that hypothetically might have caused death if it were more severe.)
Requires inpatient hospitalization or prolongation of existing hospitalization
Results in persistent or significant disability/incapacity
Is a congenital anomaly/birth defect
Is a suspected transmission of any infectious agent via a medicinal product
Is Medically Important*
*Medical and scientific judgment should be exercised in deciding whether expedited reporting is also appropriate in other situations, such as important medical events that may not be immediately life threatening or result in death or hospitalization but may jeopardize the subject or may require intervention to prevent 1 of the other outcomes listed in the definition above. These should usually be considered serious.

If a serious and unexpected adverse event occurs for which there is evidence suggesting a causal relationship between the study drug and the event (e.g., death from anaphylaxis), the event must be reported as a serious and unexpected suspected adverse reaction.

Unlisted (Unexpected) Adverse Event/Reference Safety Information

An adverse event is considered unlisted if the nature or severity is not consistent with the applicable product reference safety information.

Adverse Event Associated With the Use of the Drug

An adverse event is considered associated with the use of the drug if the attribution is possible, probable, or very likely by the definitions.

12.1.2. Attribution Definitions

Not Related

An adverse event that is not related to the use of the drug.

Doubtful

An adverse event for which an alternative explanation is more likely, e.g., concomitant drug(s), concomitant disease(s), or the relationship in time suggests that a causal relationship is unlikely.

Possible

An adverse event that might be due to the use of the drug. An alternative explanation, e.g., concomitant drug(s), concomitant disease(s), is inconclusive. The relationship in time is reasonable; therefore, the causal relationship cannot be excluded.

Probable

An adverse event that might be due to the use of the drug. The relationship in time is suggestive (e.g., confirmed by dechallenge). An alternative explanation is less likely, e.g., concomitant drug(s), concomitant disease(s).

Very Likely

An adverse event that is listed as a possible adverse reaction and cannot be reasonably explained by an alternative explanation, e.g., concomitant drug(s), concomitant disease(s). The relationship in time is very suggestive (e.g., it is confirmed by dechallenge and rechallenge).

12.1.3. Severity Criteria

An assessment of severity grade will be made using the following general categorical descriptors:

Mild

Awareness of symptoms that are easily tolerated, causing minimal discomfort and not interfering with everyday activities.

Moderate

Sufficient discomfort is present to cause interference with normal activity.

Severe

Extreme distress, causing significant impairment of functioning or incapacitation. Prevents normal everyday activities.

The investigator should use clinical judgment in assessing the severity of events not directly experienced by the subject (e.g., laboratory abnormalities).

12.2. Special Reporting Situations

Safety events of interest on a Sponsor study drug that may require expedited reporting and/or safety evaluation include, but are not limited to:
Overdose of a Sponsor study drug
Suspected abuse/misuse of a Sponsor study drug
Inadvertent or accidental exposure to a Sponsor study drug
Medication error involving a Sponsor product (with or without subject/patient exposure to the Sponsor study drug, e.g., name confusion)
Adverse events of special interest: any newly identified malignancy, opportunistic infection (i.e., infection by an organism that normally is not pathogenic or does not cause invasive infection in immunocompetent hosts), or case of active TB occurring after the first administration of study agent in subjects participating in this clinical trial must be reported by the investigator following procedures. Investigators are also advised that active TB is considered a reportable disease in most countries. These events are to be considered serious only if they meet the definition of an SAE.
Special reporting situations should also be recorded. Any special reporting situation that meets the criteria of a serious adverse event should be recorded.

12.3. Procedures 12.3.1. All Adverse Events

All adverse events and special reporting situations, whether serious or non-serious, will be reported from the time a signed and dated ICF is obtained until completion of the subject's last study-related procedure (which may include contact for follow-up of safety). Serious adverse events, including those spontaneously reported to the investigator within 16 weeks after the last dose of study drug, must be reported using the Serious Adverse Event Form. The Sponsor will evaluate any safety information that is spontaneously reported by an investigator beyond the time frame specified in the protocol.

All events that meet the definition of a serious adverse event will be reported as serious adverse events, regardless of whether they are protocol-specific assessments.

All adverse events, regardless of seriousness, severity, or presumed relationship to study drug, must be recorded using medical terminology in the source document. Whenever possible, diagnoses should be given when signs and symptoms are due to a common etiology (e.g., cough, runny nose, sneezing, sore throat, and head congestion should be reported as "upper respiratory infection"). Investigators must record their opinion concerning the relationship of the adverse event to study therapy. All measures required for adverse event management must be recorded in the source document and reported according to Sponsor instructions.

The Sponsor assumes responsibility for appropriate reporting of adverse events to the regulatory authorities. The Sponsor will also report to the investigator (and the head of the investigational institute where required) all serious adverse events that are unlisted (unexpected) and associated with the use of the study drug. The investigator (or Sponsor where required) must report these events to the appropriate Independent Ethics Committee/Institutional Review Board (IEC/IRB) that approved the protocol unless otherwise required and documented by the IEC/IRB.

The subject must be provided with a "wallet (study) card" and instructed to carry this card with them for the duration of the study indicating the following:
  Study number
  Statement, in the local language(s), that the subject is participating in a clinical study
  Investigator's name and 24-hour contact telephone number
  Local Sponsor's name and 24-hour contact telephone number (for medical staff only)
  Site number
  Subject number
  Any other information that is required to do an emergency breaking of the blind

12.3.2. Serious Adverse Events

All serious adverse events occurring during the study must be reported to the appropriate Sponsor contact person by study-site personnel within 24 hours of their knowledge of the event.

Information regarding serious adverse events will be transmitted to the Sponsor using the Serious Adverse Event Form, which must be completed and signed by a physician from the study site, and transmitted to the Sponsor within 24 hours. The initial and follow-up reports of a serious adverse event should be made by facsimile (fax).

All serious adverse events that have not resolved by the end of the study, or that have not resolved upon discontinuation of the subject's participation in the study, must be followed until any of the following occurs:
  The event resolves
  The event stabilizes
  The event returns to baseline, if a baseline value/status is available
  The event can be attributed to agents other than the study drug or to factors unrelated to study conduct
  It becomes unlikely that any additional information can be obtained (subject or health care practitioner refusal to provide additional information, lost to follow-up after demonstration of due diligence with follow-up efforts)

Suspected transmission of an infectious agent by a medicinal product will be reported as a serious adverse event. Any event requiring hospitalization (or prolongation of hospitalization) that occurs during the course of a subject's participation in a study must be reported as a serious adverse event, except hospitalizations for the following:
  Hospitalizations not intended to treat an acute illness or adverse event (e.g., social reasons such as pending placement in long-term care facility)
  Surgery or procedure planned before entry into the study (must be documented).

The cause of death of a subject in a study within 16 weeks of the last dose of study drug, whether or not the event is expected or associated with the study drug, is considered a serious adverse event.

12.3.3. Pregnancy

All initial reports of pregnancy must be reported to the Sponsor by the study-site personnel within 24 hours of their knowledge of the event using the appropriate pregnancy notification form. This includes subject report of a positive home over-the-counter pregnancy test. Abnormal pregnancy outcomes (e.g., spontaneous abortion, stillbirth, and congenital anomaly) are considered serious adverse events and must be reported using the Serious Adverse Event Form. Any subject who becomes pregnant during the study must discontinue further study treatment, and followed for 4 months after last study dose.

Because the effect of the study drug on sperm is unknown, pregnancies in partners of male subjects included in the study will be reported by the study-site personnel within 24 hours of their knowledge of the event using the appropriate pregnancy notification form.

Follow-up information regarding the outcome of the pregnancy and any postnatal sequelae in the infant will be required.

13. Product Quality Complaint Handling

A product quality complaint (PQC) is defined as any suspicion of a product defect related to manufacturing, labeling, or packaging, i.e., any dissatisfaction relative to the identity, quality, durability, or reliability of a product, including its labeling or package integrity. A PQC may have an impact on the safety and efficacy of the product. Timely, accurate, and complete reporting and analysis of PQC information from studies are crucial for the protection of subjects, investigators, and the Sponsor, and are mandated by regulatory agencies worldwide. The Sponsor has established procedures in conformity with regulatory requirements worldwide to ensure appropriate reporting of PQC information; all studies conducted by the Sponsor or its affiliates will be conducted in accordance with those procedures.

13.1. Procedures

All initial PQCs must be reported to the Sponsor by the study-site personnel within 24 hours after being made aware of the event.

If the defect is combined with a serious adverse event, the study-site personnel must report the PQC to the Sponsor according to the serious adverse event reporting timelines (refer to Section 12.3.2, Serious Adverse Events). A sample of the suspected product should be maintained for further investigation if requested by the Sponsor.

14. Study Drug Information

14.1. Physical Description of Study Drug

14.1.1. IV Administration

Ustekinumab 5 mg/mL FVP (IV) is supplied as a single-use, sterile solution in 30 mL vials with 1 dose strength (i.e., 130 mg in 26 mL nominal volume). In addition to ustekinumab, the solution contains 10 mM L-histidine, 8.5% (w/v) sucrose, 0.04% (w/v) polysorbate 80, 0.4 mg/mL L-methionine, and 20 µg/mL EDTA disodium salt, dihydrate at pH 6.0. No preservatives are present.

Placebo for FVP (IV) is supplied as single-use, sterile solution in 30 mL vials with a 26 mL nominal volume. The composition of the placebo is 10 mM L-histidine, 8.5% (w/v) sucrose, 0.04% (w/v) polysorbate 80, 0.4 mg/mL L-methionine, and 20 µg/mL EDTA disodium salt, dihydrate at pH 6.0. No preservatives are present.

14.1.2. SC Administration

Ustekinumab will also be supplied as a single-use latex-free PFS in a strength of 90 mg in 1 mL nominal volume for SC administration. Each 1 mL of ustekinumab solution in the PFS contains 90 mg ustekinumab with nominal excipient concentrations of 6.7 mM L-histidine, 7.6% (w/v) sucrose, 0.004% (w/v) polysorbate 80, at pH 6.0. No preservatives are present. The needle cover on the PFS contains dry natural rubber (a derivative of latex), which may cause allergic reactions in individuals sensitive to latex.

Placebo administrations will have the same appearance as the respective ustekinumab administrations. Liquid placebo will also be supplied in a 1 mL PFS, and have a composition 10 mM L-histidine, 8.5% (w/v) sucrose, 0.004% (w/v) polysorbate 80, at pH 6.0. No preservatives are present. The needle cover on the PFS contains dry natural rubber (a derivative of latex), which may cause allergic reactions in individuals sensitive to latex.

CONCLUSION

Safety and Efficacy of Ustekinumab in Patients with Systemic Lupus Erythematosus: Results of a Phase 2, Randomized, Placebo-Controlled, Study

Background/Purpose

The IL-12/23 pathway has been implicated in the pathogenesis of Systemic Lupus Erythematosus (SLE). The anti-IL-12/IL-23p40 antibody ustekinumab is used in the treatment of psoriasis, psoriatic arthritis, and Crohn's disease. Here, the safety and efficacy of usetkinumab was evaluated in patients with active SLE.

Methods

A phase 2, placebo-controlled study, was conducted in 102 adults with seropositive (ANA, anti-dsDNA, and/or anti-Smith antibodies) SLE by SLICC criteria and active disease (SLEDAI-2K ≥6 and ≥1 BILAG A and/or ≥2 BILAG B scores) despite conventional therapy. Patients (n=102) were randomized (3:2) to receive ustekinumab intravenous (IV) at ~6 mg/kg or placebo at week 0, then subcutaneous (SC) injections of ustekinumab 90 mg q8w or placebo, both added to standard care; stratification factors were consent for skin biopsy (yes/no), disease features, (e.g., presence of LN, baseline concomitant SLE medications, SLEDAI score), site/region, and race. At week 24, placebo patients crossed over to ustekinumab (90 mg SC q8w). Primary endpoint was SLE response index (SRI-4) response at week 24. Major secondary endpoints at week 24 included change from baseline in SLEDAI-2K, change from baseline in Physician's Global Assessment (PGA), and proportion of patients with BICLA response. Endpoint analyses included all patients who received ≥1 dose of study agent, had ≥1 measurement prior to administration, and had ≥1 post-baseline measurement. Modified intention-to-treat (mITT) analyses across SLE disease activity measures were performed to evaluate for maintenance of response with ustekinumab between week 24 and week 48. Subjects crossing over from placebo to SC ustekinumab were also assessed for de novo clinical responses across disease activity measures. Safety was assessed through week 56. Patients with missing data and treatment failures were imputed as nonresponders.

Results

Patient demographic and disease characteristics were well-balanced between treatment groups (female=91%; mean age=41 (18-66) years; mean SLEDAI-2K=10.9). At week 24, 61.7% of patients in the ustekinumab group had an SRI-4 response vs 33.3% in the placebo group (p=0.0057), with a treatment effect favoring ustekinumab beginning at week 12. Patients in the ustekinumab group had greater median improvements from week 0 to week 24 in SLEDAI-2K and PGA vs placebo (Table 5). Furthermore, rates of SLEDAI-2K (65% at week 24 vs 66.7% at 1 year), PGA (67.9% at week 24 vs 75% at 1 year), and active joint (86.5% at week 24 vs 86.5% at 1 year) responses were also sustained from week 24 to 1 year in the ustekinumab group (Table 6). CLASI response rate plateaued by week 28 (53.1% at week 24 vs 67.7% at week 28) and was maintained through 1 year in the ustekinumab group (68.6%) (Table 6). No difference was observed in the proportion of patients achieving a BICLA composite response at week 24, although a notable difference in the proportion of patients with no BILAG worsening among BICLA nonresponders was observed. The risk of a new BILAG flare (≥1 new BILAG A or ≥2 new BILAG B) was significantly lower in the ustekinumab group vs. placebo (HR 0.12 [95% CI 0.01-0.94]; p=0.0119). Ustekinumab also demonstrated improvement in musculoskeletal and mucocutaneous disease features vs placebo. Improvements in anti-dsDNA and C3 levels were also noted through week 24 with ustekinumab. Through week 24, 78% of ustekinumab patients and 67% of placebo patients had ≥1 adverse event (Table 5). Among placebo patients who crossed over to SC ustekinumab at week 24 (n=33), 54.5% achieved an SRI-4 response at 1 year. Placebo patients who crossed over to SC ustekinumab at week 24 also demonstrated greater response rates across multiple efficacy measures including proportion of patients with ≥4 point improvement from baseline SLEDAI-2K (46% at 24 weeks vs 55% at 1 year), proportion of patients with 30% improvement from baseline PGA (56% at 24 weeks vs 77% at 1 year), proportion of patients with 50% improvement in the number of active joints at baseline (61% at week 24 vs 82% at 1 year), and proportion of patients with 50% improvement from baseline CLASI Activity Score (35% at Wk 24 vs. 47% at 1 year). Of ustekinumab-exposed patients, 81.7% had ≥1

TEAE, 15.1% had ≥1 SAE, and 7.5% had ≥1 serious infection through 1 year (Table 7). There were no deaths, malignancies, opportunistic infections, or tuberculosis cases observed in the study. The ustekinumab safety profile was consistent with earlier studies in other diseases.

Conclusion

Ustekinumab showed significantly better efficacy in many clinical and laboratory parameters in active SLE compared to placebo and comparable safety at 24 weeks. Ustekinumab also provided sustained clinical benefit in global and organ-specific SLE activity measures through 1 year. De novo increases in response rates across disease activity measures were observed in patients who crossed over from placebo to SC ustekinumab at week 24. The safety profile of ustekinumab was also consistent with other indications. Thus, ustekinumab is a clinically proven safe and clinically proven effective therapy with a novel mechanism of action for the treatment of SLE.

TABLE 5

Efficacy and Safety Results at Week 24.

|  | Placebo | Ustekinumab |
|---|---|---|
| Patients randomized, n | 42 | 60 |
| Efficacy |  |  |
| Proportion with SRI-4 response, n (%) | 14 (33.3%) | 37 (61.7%) |
| P value |  | 0.0057 |
| Median change from baseline in SLEDAI-2K | −2.0 | −6.0 |
| P value |  | 0.0265$^a$ |
| Median change from baseline in PGA | −1.6 | −2.5 |
| P value |  | 0.2110$^a$ |
| Proportion with BICLA response | 14 (33.3) | 21 (35.0) |
| P value |  | 0.9939 |
| Proportion with no BILAG worsening, n/N (%) | 11/42 (26.2) | 29/60 (48) |
| P value | .3 | 0.0281 |
| Proportion with 50% improvement from baseline joint disease activity$^b$ | 61 | 86 |
| P value |  | 0.0100$^d$ |
| Proportion with 50% improvement from baseline CLASI activity score$^c$ | 29.9 | 64.1 |
| P value |  | 0.0319$^d$ |
| Mean (SD) change from baseline in anti-dsDNA (kIU/L) | −3.7 (96.8) | −226.6 (686.5) |
| P value |  | 0.2482 |
| Complement C3 (mg/dL) | 3.6 (10.7) | 8.3 (15.1) |
| P value |  | 0.2749 |
| Adverse events |  |  |
| Proportion with ≥1 TEAE, n (%) | 29 (69.0) | 47 (78.3) |
| Most Common TEAEs, n (%) |  |  |
| Upper respiratory tract infection | 9 (21.4) | 5 (8.3%) |
| Urinary tract infection | 5 (11.9) | 6 (10.0%) |
| Nasopharyngitis | 3 (7.1) | 6 (10.0%) |
| Headache | 5 (11.9) | 4 (6.7%) |
| Proportion with ≥1 SAE, n (%) | 4 (9.5) | 5 (8.3%) |

$^a$One-sided test for no difference between two treatment groups based upon a Wilcoxon non-parametric median test for difference of location.
$^b$Patient subpopulation (~70% of total population) with at least 4 joints with pain and signs of inflammation at baseline
$^c$Patient subpopulation (~60% of total population) with CLASI activity score of at least 4 at baseline
SRI-4, SLE Response Index; SLEDAI 2K, Systemic Lupus Erythematosus Disease Activity Index; PGA, physician's global assessment; BICLA, BILAG-based Combined Lupus Assessment; BILAG, British Isles Lupus Assessment Group; TEAE, treatment emergent adverse event
$^d$Proportions of responders and p values based on a modified intention to treat analysis using a multiple imputation model for missing data from weeks 16 to 24

TABLE 6

Efficacy results at 24 weeks and 1 year in patients initially randomized to ustekinumab

|  | Ustekinumab | |
|---|---|---|
|  | Week 24 | Week 48 |
| Randomized patients (mITT) | 60 | 60 |
| SRI-4 response$^a$, n/randomized (%) | 37/60 (61.7) | 38/60 (63.3) |
| Improvement from baseline in SLEDAI-2K score$^b$, n/randomized (%) | 39/60 (65.0) | 40/60 (66.7) |
| ≥30% improvement from baseline in PGA, n/evaluable$^c$ (%) | 38/56 (67.9) | 39/52 (75.0) |
| ≥50% improvement from baseline in the number of joints with pain and signs of inflammation, n/evaluable$^{c,d}$ (%) | 32/37 (86.5) | 32/37 (86.5) |
| ≥50% improvement from baseline CLASI activity score, n/evaluable$^{c,e}$ (%) | 17/32 (53.1) | 24/35 (68.6) |

$^a$SRI-4 response was defined as a ≥4-point reduction in SLEDAI-2K total score, no new BILAG A and no more than 1 new BILAG B domain score, and no worsening (<10% increase) from baseline in the PGA of disease activity score
$^b$SLEDAI-2K response defined as ≥4-point improvement from baseline score
$^c$Values for patients meeting treatment failure criteria are set to missing from the point of treatment failure forward
$^d$Patient subpopulation (67% of total population) with ≥4 joints with pain and signs of inflammation at baseline
$^e$Patient subpopulation (60% of total population) with CLASI activity score of ≥4 at baseline
CLASI, Cutaneous Lupus Erythematosus Disease Area and Severity Index; mITT, modified intention-to-treat; PBO, placebo; PGA, Physician Global Assessment; SLEDAI-2K, Systemic Lupus Erythematosus Disease Activity Index 2000; SRI-4, SLE Responder Index-4; UST, ustekinumab

TABLE 7

Safety results at 24 weeks and 1 year

|  | Placebo-controlled through Week 24 | | Exposed to ustekinumab through 1 year | |
|---|---|---|---|---|
|  | PBO | UST | Randomized to UST | All UST (UST + PBO-UST) |
| Treated patients | 42 | 60 | 60 | 93 |
| Patients with ≥1 TEAE | 29 (69.0) | 47 (78.3) | 54 (90.0) | 76 (81.7) |
| Patients with ≥1 SAE | 4 (9.5) | 5 (8.3) | 10 (16.7) | 14 (15.1) |
| Patients with ≥1 infection$^a$ | 21 (50.0) | 29 (48.3) | 40 (66.7) | 56 (60.2) |
| Patients with ≥1 serious infection$^a$ | 0 (0) | 2 (3.3) | 6 (10.0) | 7 (7.5) |
| Patients with ≥1 DCAE | 4 (9.5) | 4 (6.7) | 5 (8.3) | 6 (6.5) |

All data are presented as n (%).
$^a$Based on infection system organ class
DCAE, adverse event leading to discontinuation; PBO, placebo; PBO-UST, patients who crossed over from PBO to UST at week 24; SAE, serious adverse event; TEAE, treatment-emergent adverse event; UST, ustekinumab

TABLE 8

Comprehensive Summary of Efficacy Results at Week 24.

|  | Placebo | Ustekinumab | Difference | P value |
|---|---|---|---|---|
| Patients randomized, n | 42 | 60 | | |
| Primary Endpoint | | | | |
| SRI-4 response, n (%) | 14 (33%) | 37 (62%) | 28.4% (9.5 to 47.2) | 0.0057[a] |
| Major Secondary Endpoints | | | | |
| Change from baseline in SLEDAI-2K, mean (SD) | −3.8 (5.4) | −4.4 (2.9) | −0.63 (−2.4 to 1.17) | 0.0929[a] |
| Change from baseline in PGA, mean (SD) | −1.9 (2.2) | −2.2 (1.9) | −0.24 (−1.13 to 0.64) | 0.3944[a,b] |
| BICLA response, n (%) | 14 (33%) | 21 (35%) | 1.7% (−17.0 to 20.3) | 0.9939[a,b] |
| Additional Endpoints | | | | |
| SRI-5 response, n (%) | 9 (21%) | 26 (43%) | 21.9% (4.3 to 39.5) | 0.0218[a,b] |
| SRI-6 response, n (%) | 8 (19%) | 26 (43%) | 24.3% (7.0 to 41.6) | 0.0122[a,b] |
| SLEDAI-2K response[c,d] | | | | |
| Patients, n/N (%) | 15/31 (48%) | 38/53 (72%) | 23.3% (4.4 to 42.2) | |
| Mean response rate, % (95% CI) | 49.1% (48.2 to 50.0) | 76.8% (76.4 to 77.2) | | 0.0071[a,b] |
| Modified SLEDAI-2K response[c,e] | | | | |
| Patients, n/N (%) | 18/32 (56%) | 40/56 (71%) | 15.2% (−3.7 to 34.0) | |
| Mean response rate, % (95% CI) | 51.6% (35.4 to 67.4) | 75.0% (61.4 to 85.0) | | 0.0162[b] |
| PGA improvement from baseline ≥30%, n (%) | 18 (43%) | 37 (62%) | 18.8% (−0.6 to 38.2) | 0.0815[b] |
| No worsening in PGA[c] | | | | |
| Patients, n/N (%) | 29/32 (91%) | 51/55 (93%) | 2.1% (−8.9 to 13.1) | |
| Mean response rate, % (95% CI) | 88.9% (73.4 to 95.9) | 92.4% (81.4 to 97.1) | | 0.3121[a,b] |
| No worsening in BILAG score, n (%) | 11 (26%) | 29 (48%) | 22.1% (3.8 to 40.5) | 0.0281[a,b] |
| ≥50% improvement from baseline joint disease activity[c,f], % (95% CI) | | | | |
| Patients, n/N (%) | 14/23 (61%) | 32/37 (86%) | 25.6% (8.5 to 42.7) | |
| Mean response rate, % (95% CI) | 65.5% (44.6 to 81.7) | 90.1% (75.2 to 96.5) | | 0.0100[b] |
| ≥50% improvement from baseline CLASI activity score[c,g], % (95% CI) | | | | |
| Patients, n/N (%) | 6/17 (35%) | 17/32 (53%) | 17.8% (−1.4 to 37.0) | |
| Mean response rate, % (95% CI) | 29.9% (12.0 to 57.0) | 64.1% (43.0 to 80.9) | | 0.0319[b] |

[a] Prespecified analyses; all other analyses shown here were post-hoc.
[b] Nominal p value; not adjusted for multiplicity.
[c] Proportion of patients with response are reported as observed values at Week 24 and mean response rates using multiple imputation for missing data.
[d] SLEDAI-2K response is the proportion of patients with at least 4-point improvement from baseline SLEDAI score.
[e] Modified SLEDAI-2K response is the proportion of patients with SLEDAI-2K response excluding serologic markers of disease activity (C3, C4, and anti-double-stranded DNA antibodies).
[f] Patient subpopulation (67% of total population) with ≥4 joints with pain and signs of inflammation at baseline.
[g] Patient subpopulation (58% of total population) with CLASI activity score ≥4 at baseline.
BICLA = BILAG-based Combined Lupus Assessment. BILAG = British Isles Lupus Assessment Group. CI = confidence interval. CLASI = Cutaneous Lupus Erythematosus Disease Area and Severity Index. PGA = physician's global assessment. SD = standard deviation. SLEDAI-2K = Systemic Lupus Erythematosus Disease Activity Index 2000. SRI = Systemic Lupus Erythematosus Disease Activity Index 2000 Responder Index.

REFERENCES

1. Albrecht J, Taylor L, Berlin J A, et al. The CLASI (Cutaneous Lupus Erythematosus Disease Area and Severity Index): an outcome instrument for cutaneous lupus erythematosus. *J Invest Dermatol.* 2005; 125(5): 889-894.
2. Bennett L, Palucka A K, Arce E, et al. Interferon and granulopoiesis signatures in systemic lupus erythematosus blood. *J Exp Med.* 2003; 197:711-723.
3. Chen X Q, Yu Y C, Deng H H, et al. Plasma IL-17A is increased in new-onset SLE patients and associated with disease activity. *J Clin Immunol.* 2010; 30:221-225.
4. Crispin J C, Oukka M, Bayliss G, et al. Expanded double negative T cells in patients with systemic lupus erythematosus produce IL-17 and infiltrate the kidneys. *J Immunol.* 2008; 181:8761-8766.
5. Dahl C, Johansen C, Kragballe K, Olesen A B. Ustekinumab in the treatment of refractory chronic cutaneous lupus erythematosus: a case report. *Acta Derm Venereol.* 2013; 93:368-369.

6. De Souza A, Ali-Shaw T, Strober B E, Franks Jr A G. Successful treatment of subacute lupus erythematosus with ustekinumab. *Arch Dermatol.* 2011; 147: 896-898.
7. Feagan, B G, Sandborn W J, Gasink C, et al. Ustekinumab as Induction and Maintenance Therapy for Crohn's Disease. *N Engl J Med.* 2016; 375(20):1946-1960.
8. Felson D T, Anderson J J, Boers M, et al. American College of Rheumatology preliminary definition of improvement in rheumatoid arthritis. *Arthritis Rheum.* 1995; 38(6):727-735.
9. Fine D M, Ziegenbein M, Petri M, et al. A prospective study of protein excretion using short-interval timed urine collections in patients with lupus nephritis. *Kidney Int.* 2009; 76(12):1284-1288.
10. Furie R A, Petri M A, Wallace D J, et al. Novel evidence-based systemic lupus erythematosus responder index. *Arthritis & Rheumatism.* 2009; 61(9):1143-1151.
11. Gladman D D, Ibañez D, Urowitz M B. Systemic lupus erythematosus disease activity index 2000. *J Rheumatol.* 2002; 29(2):288-291.
12. Han J W, Zheng H F, Cui Y, et al. Genome-wide association study in a Chinese Han population identifies nine new susceptibility loci for systemic lupus erythematosus. *Nat Genet.* 2009; 41:1234e7.
13. Hay E M, Bacon P A, Gordon C, et al. The BILAG index: a reliable and valid instrument for measuring clinical disease activity in systemic lupus erythematosus. *Quart J Medicine.* 1993; 86:447-458.
14. Huang X, Hua J, Shen N, Chen S. Dysregulated expression of interleukin-23 and interleukin-12 subunits in systemic lupus erythematosus patients. *Mod Rheumatol.* 2007; 17(3):220-223.
15. Illei, G., Wang, L., Greth, W., & Khamashta, M. (2015). The effect of geography on the efficacy of sifalimumab, an anti-interferon alpha monoclonal antibody, in moderate to severe systemic lupus erythematosus. Gaithersburg: MedImmune. *Clin Exp Rheumatol.* 2015; 33(3 Suppl.90):abstr P5.10 (11th International Congress on Systemic Lupus Erythematosus, 2-6 Sep. 2015, Vienna, Austria).
16. International Consortium for Systemic Lupus Erythematosus Genetics (SLEGEN), Harley J, Alarcón-Riquelme M, et al. Genome-wide association scan in women with systemic lupus erythematosus identifies susceptibility variants in ITGAM, PXK, KIAA1542 and other loci. *Nat Genet.* 2008; 40(2):204-210.
17. Isenberg D A, Rahman A, Allen E, et al. BILAG 2004. Development and initial validation of an updated version of the British Isles Lupus Assessment Group's disease activity index for patients with systemic lupus erythematosus. *Rheumatology.* 2005; 44:902-906.
18. Kim H S, Kim I, Kim J O, Bae J S, Shin H D, Bae S C, No association between interleukin 23 receptor gene polymorphisms and systemic lupus erythematosus. *Rheumatol Int.* 2009; 30: 33-38.
19. Krupp L B, LaRocca N G, Muir-Nash J, Steinberg A D. The fatigue severity scale: application to patients with multiple sclerosis and systemic lupus erythematosus. *Arch Neurol.* 1989; 46(10); 1121-1123.
20. Linker-Israeli M, Deans R J, Wallace D J, et al. Elevated levels of endogenous IL-6 in systemic lupus erythematosus. A putative role in pathogenesis. *J Immunol.* 1991; 147:117-123.
21. McHorney C A, Ware J E Jr, Lu J F, Sherbourne C D. The MOS 36-item Short-Form Health Survey (SF-36): III. Tests of data quality, scaling assumptions, and reliability across diverse patient groups. *Med Care.* 1994; 32(1):40-66.
22. Navarra S V, Guzmán R M, Gallacher A E, et al. Efficacy and safety of belimumab in patients with active systemic lupus erythematosus: a randomised, placebo-controlled, phase 3 trial. *Lancet.* 2011; 377:721-731.
23. Niewold T B, Hua J, Lehman T J A, Harley J B, Crow M K. High serum IFN-α activity is a heritable risk factor for systemic lupus erythematosus. Genes *Immuno.* 2007, 8(6):492-502.
24. Oh S H, Roh H J, Kwon J E, et al. Expression of interleukin-17 is correlated with interferon-α expression in cutaneous lesions of lupus erythematosus. *Clin Exp Dermatol.* 2011; 36:512-520.
25. Petri M, Orbai A M, Alarcón G S, et al. Derivation and validation of the Systemic Lupus International Collaborating Clinics classification criteria for systemic lupus erythematosus. *Arthritis Rheum.* 2012; 64(8):2677-2686.
26. Qiu F, Song L, Yang N, Li X. Glucocorticoid downregulates expression of IL-12 family cytokines in systemic lupus erythematosus patients. *Lupus.* 2013; 22(10): 1011-1016.
27. Samsa G, Edelman D, Rothman M L, et al. Determining clinically important differences in health status measures: a general approach with illustration to the Health Utilities Index Mark II. *Pharmacoeconomics.* 1999; 15(2):141-155.
28. Sanchez E, Rueda B, Callejas J L, et al. Analysis of interleukin-23 receptor (IL23R) gene polymorphisms in systemic lupus erythematosus. *Tissue Antigens.* 2007; 70:233-237.
29. Sestak A L, Fürnrohr B G, Harley J B, Merrill J T, Namjou B. The genetics of systemic lupus erythematosus and implications for targeted therapy. *Ann Rheum Dis.* 2011; 70(S1): i37-i43.
30. Shah K, Lee W W, Lee S H, et al. Dysregulated balance of Th17 and Th1 cells in systemic lupus erythematosus. *Arthritis Res Ther.* 2010; 12:R53.
31. Tanasescu C E, Balanescu P, Balanescu R, et al. IL-17 in cutaneous lupus erythematosus. *Eur J Intern Med.* 2010; 21:202-207.
32. Touma Z, Gladman D D, Ibanez D, Urowitz M B. Development and initial validation of the systemic lupus erythematosus disease activity index 2000 responder index 50. *J Rheumatol.* 2011; 38:2; doi:10.3899/jrheum.100724.
33. Touma Z, Gladman D D, Urowitz M B. SLEDAI-2K for a 30 day window. *Lupus.* 2010a; 19(1):49-51. Epub 2009 Nov. 12.
34. Touma Z, Urowitz M, Ibanez D, Gladman D. SLEDAI-2K 10 days versus SLEDAI-2K 30 days in a cross-sectional and longitudinal evaluation. *Lupus. The 9th International Congress on SLE* Jun. 24-27 2010c, Vancouver, Canada. Abstract PO2.D.6.
35. Touma Z; Urowitz M, Gladman D. SLEDAI-2K Responder Index-50 (SRI-50). *Lupus. The 9th International Congress on SLE* Jun. 24-27 2010b, Vancouver, Canada. Abstract PO2.D.7.
36. Van Vollenhoven R F, Petri M A, Cervera R. et al. Belimumab in the treatment of systemic lupus erythematosus: high disease activity predictors of response. *Ann Rheum Dis.* 2012; 71(8):1343-1349.
37. Vincent F B, Northcott M, Hoi A, et al. Clinical associations of serum interleukin-17 in systemic lupus erythematosus. *Arthritis Res Ther.* 2013; 15: R97.
38. Wallace D J, Strand D, Furie V, et al. Evaluation of Treatment Success in Systemic Lupus Erythematosus Clinical Trials: Development of the British Isles Lupus Assessment Group-based Composite Lupus Assessment Endpoint. *Arthritis Rheum.* 2011; 63 (S10):5885.
39. Wallace D J. Lupus: The essential clinician's guide. New York, NY: Oxford University Press, Inc; 2008.
40. Ware J E. SF-36 Health Survey Update. *Spine.* 2000; 25(24):3130-3139.
41. Ware J E, Kosinski M, Keller S K. SF-36 Physical and Mental Health Summary Scales: A User's Manual. Boston MA The Health Institute, 1994.
42. Ware J E Jr, Sherbourne C D. The MOS 36 item short-form health survey (SF 36), I: conceptual framework and item selection. *Med Care.* 1992; 30(6):473-483.
43. Winchester D, Duffin K C, Hansen C. Response to ustekinumab in a patient with both severe psoriasis and hypertrophic cutaneous lupus. *Lupus.* 2012; 21:1007-1010.
44. Wong C K, Lit L C W, Tam L S, et al. Hyperproduction of IL-23 and IL-17 in patients with systemic lupus erythematosus: implications for Th17-mediated inflammation in auto-immunity. *Clin Immunol.* 2008; 127: 385-393.
45. Yang X, Wang H, Zhao X, et al. Th22, but not Th17 might be a good index to predict the tissue involvement of systemic lupus erythematosus. *J Clin Immunol.* 2013; 33:767-774.
46. Zhao X F, Pan H F, Yuan H, et al. Increased serum interleukin 17 in patients with systemic lupus erythematosus. *Mol Biol Rep.* 2010; 37:81-85.

APPENDIX 1

| | Efficacy Evaluations | Description | Composed of Other Assessments |
|---|---|---|---|
| BILAG | British Isles Lupus Assessment Group | Measure of alterations to therapy consisting of 97 questions in 9 organ systems, each put into 1 of 5 categories (A, B, C, D, E) depending on presence of items. Higher scores indicate more disease involvement. | |
| BICLA | BILAG-based Combined Lupus Assessment | Composite requiring subjects to meet response criteria across the BILAG, PGA and SLEDAI-2K index. | BILAG PGA SLEDAI-2K |
| CLASI | Cutaneous Lupus Erythematosus Disease Area and Severity Index | Assesses the disease activity and damage caused to the skin for CLE patients. Scored 0-70 for activity and 0-56 for damage with higher scores indicating extremely active Lupus. | |
| Flares | SLEDAI flare Severe SLEDAI flare BILAG flare | SLEDAI flare: At least a 4+ point increase in SLEDAI-2K score (includes severe flares). Severe SLEDAI flare: At least a 7+ point increase in SLEDAI-2K score. BILAG flare: At least 1 new BILAG A or 2 new BILAG B scores (from scores < B) | BILAG SLEDAI-2K |
| FSS | Fatigue Severity Scale | A 9-item questionnaire designed to assess the severity of fatigue and its impact on daily living. Each item scored from 1-7 with higher score indicating more severe impact. Scored 9-63. | |
| Pain VAS | Patients Numeric Rating Scale of Pain | Measures the patient's assessment of pain on a visual analogue scale (VAS; 0 to 10 cm). The anchors of the instrument include 0 to represent 'no pain' and 10 to represent 'the worst pain.' | |
| PGA | Physician's Global Assessment of Disease Activity | Measures the PGA on a VAS scale. Each scored from 0-10 with higher scores indicating worse activity. | |
| PtGA | Patient's Global Assessment of Disease Activity | Measures the PtGA on a VAS scale. Each scored from 0-10 with higher scores indicating worse activity. | |
| SF-36 | RAND Short-Form-36 Health Survey | Measures 36 items within 8 health domains. Scored 0-100 for each health concept with higher scores indicating an improved health state. In addition, health concepts can be combined into either a physical or mental component, also scored 0-100. | |
| SLEDAI-2K (Baseline) | Systemic Lupus Erythematosus Disease Activity Index 2000 | Measures 24 features in 9 organ domains over the previous 30 days. Scored 0-105 with higher scores indicating more disease activity. | |
| S2K RI-50 (Follow-up) | SLEDAI-2K Responder Index 50 | Measures clinically important 50% reduction in SLEDAI-2K score. | SLEDAI-2K |
| SRI-4 | SLE Responder Index-4 | Composite endpoint requiring at least a 4 point reduction in SLEDAI 2K, no worsening (<10 mm increase) from baseline in PGA and no new BILAG Domain A and no more than 1 new BILAG Domain B scores (see Section 9.2.2.1.). | SLEDAI-2K PGA BILAG |
| SRI-5 and SRI-6 | SLEDAI 2-K SLE Responder Index-5 and SLEDAI 2-K SLE Responder Index-6 | Same criteria as SRI-4 however the SRI-5 and SRI-6 require at least a 5 point or 6 point reduction in SLEDAI-2K respectively. | SLEDAI-2K PGA BILAG |

Appendix 2: QuantiFERON®-TB Gold Testing

The QuantiFERON®-TB Gold test is one of the interferon-γ (IFN-γ) based blood assays for TB screening (Cellestis, 2009). It utilizes the recently identified *M tuberculosis*-specific antigens ESAT-6 and CFP-10 in the standard format, as well as TB7.7 (p4) in the In-Tube format, to detect in vitro cell-mediated immune responses in infected individuals. The QuantiFERON®-TB Gold assay measures the amount of IFN-γ produced by sensitized T cells when stimulated with the synthetic *M. tuberculosis*-specific antigens. In *M. tuberculosis*-infected persons, sensitized T lymphocytes will secrete IFN-γ in response to stimulation with the *M. tuberculosis*-specific antigens and, thus, the QuantiFERON®-TB Gold test should be positive. Because the antigens used in the test are specific to *M. tuberculosis* and not found in BCG, the test is not confounded by BCG vaccination, unlike the tuberculin skin test. However, there is some cross-reactivity with the 3 *Mycobacterium* species, *M. kansasii*, *M. marinum*, and *M. szulgai*. Thus, a positive test could be the result of infection with one of these 3 species of *Mycobacterium*, in the absence of *M. tuberculosis* infection.

In a study of the QuantiFERON®-TB Gold test (standard format) in subjects with active TB, sensitivity has been shown to be approximately 89% (Mori et al, 2004). Specificity of the test in healthy BCG-vaccinated individuals has been demonstrated to be more than 98%. In contrast, the sensitivity and specificity of the tuberculin skin test was noted to be only about 66% and 35% in a study of Japanese patients with active TB and healthy BCG-vaccinated young adults, respectively. However, sensitivity and specificity of the tuberculin skin test depend on the population being studied, and the tuberculin skin test performs best in healthy young adults who have not been BCG-vaccinated.

Data from a limited number of published studies examining the performance of the QuantiFERON®-TB Gold assay in immunosuppressed populations suggest that the sensitivity of the QuantiFERON®-TB Gold test is better than the tuberculin skin test even in immunosuppressed patients (Ferrara et al, 2005; Kobashi et al, 2007; Matulis et al, 2008). The ability of IFN-γ-based tests to detect latent infection has been more difficult to study due to the lack of a gold standard diagnostic test; however, several TB outbreak studies have demonstrated that the tests correlated better than the tuberculin skin test with the degree of exposure that contacts had to the index TB case (Brock et al, 2004; Ewer et al, 2003). In addition, TB contact tracing studies have shown that patients who had a positive QuantiFERON®-TB Gold test result and were not treated for latent TB infection were much more likely to develop active TB during longitudinal follow-up than those who had a positive tuberculin skin test and a negative QuantiFERON®-TB Gold test result (Higuchi et al, 2007; Diel et al, 2008).

Although the performance of the new IFN-γ-based blood tests for active or latent *M. tuberculosis* infection have not been well validated in the immunosuppressed population, experts believe these new tests will be at least as, if not more, sensitive, and definitely more specific, than the tuberculin skin test (Barnes, 2004; personal communication, April, 2008 TB Advisory Board).

Performing the QuantiFERON®-TB Gold in Tube Test

The QuantiFERON®-TB Gold test In-Tube format will be provided for this study. The In-Tube format contains 1 additional *M. tuberculosis*-specific antigen, TB7.7 (p4), which is thought to increase the specificity of the test.

To perform the test using the In-Tube format, blood is drawn through standard venipuncture into supplied tubes that already contain the *M. tuberculosis*-specific antigens. Approximately 3 tubes will be needed per subject, each requiring 1 mL of blood. One tube contains the *M. tuberculosis*-specific antigens, while the remaining tubes contain positive and negative control reagents. Thorough mixing of the blood with the antigens is necessary prior to incubation. The blood is then incubated for 16 to 24 hours at 37° C., after which tubes are centrifuged for approximately 15 minutes at 2000 to 3000 g. Following centrifugation, plasma is harvested from each tube, frozen, and shipped on dry ice to the central laboratory. The central laboratory will perform an ELISA to quantify the amount of IFN-γ present in the plasma using spectrophotometry and computer software analysis.

The central laboratory will analyze and report results for each subject, and sites will be informed of the results. Subjects who have an indeterminate result should have the test repeated.

Adherence to Local Guidelines

Local country guidelines for immunocompromised patients should be consulted for acceptable anti-tuberculous treatment regimens for latent TB. If no local country guidelines for immunocompromised patients exist, US guidelines must be followed.

In countries in which the QuantiFERON®-TB Gold test is not considered approved/registered, a tuberculin skin test is additionally required.

REFERENCES

Barnes P F. Diagnosing latent tuberculosis infection: Turning glitter to gold [editorial]. *Amer J Respir Crit Care Med.* 2004; 170:5-6.

Brock I, Weldingh K, Lillebaek T, et al. Comparison of tuberculin skin test and new specific blood test in tuberculosis contacts. *Am J Respir Crit Care Med.* 2004; 170:65-69.

Cellestis. QuantiFERON-TB Gold clinicians guide and QuantiFERON-TB Gold In-Tube Method package insert. Downloaded from www.cellestis.com, February 2009.

Diel R, Loddenkemper R, Meywald-Walter K, Niemann S, Nienhaus A. Predictive value of a whole blood IFN-λ assay for the development of active tuberculosis disease after recent infection with *Mycobacterium tuberculosis*. *Am J Respir Crit Care Med.* 2008; 177:1164-1170.

Ewer K, Deeks J, Alvarez L, et al. Comparison of T-cell-based assay with tuberculin skin test for diagnosis of *Mycobacterium tuberculosis* infection in a school tuberculosis outbreak. *Lancet.* 2003; 361:1168-73.

Ferrara G, Losi M, Meacci M, et al. Routine hospital use of a new commercial whole blood interferon-γ assay for the diagnosis of tuberculosis infection. *Am J Respir Crit Care Med.* 2005; 172:631-635.

Higuchi K, Nobuyuki H, Mori T, Sekiya Y. Use of QuantiFERON-TB Gold to investigate tuberculosis contacts in a high school. *Respirology.* 2007; 12:88-92.

Kobashi Y, Mouri K, Obase Y, et al. Clinical evaluation of QuantiFERON-TB-2G test for immunocompromised patients. *Eur Respir J.* 2007; 30:945-950.

Matulis G, Jüni P, Villiger P M, Gadola S D. Detection of latent tuberculosis in immunosuppressed patients with autoimmune diseases: performance of a *Mycobacterium tuberculosis* antigen-specific interferon λ assay. *Ann Rheum Dis*. 2008; 67:84-90

Mori T, Sakatani M, Yamagishi F, et al. Specific detection of tuberculosis infection: An interferon-γ-based assay using new antigens. *Am J Respir Crit Care Med*. 2004; 170:59-64.

Appendix 3: Tuberculin Skin Testing

Administering the Mantoux Tuberculin Skin Test

The Mantoux tuberculin skin test (CDC, 2000) is the standard method of identifying persons infected with *Mycobacterium tuberculosis*. Multiple puncture tests (Tine and Heaf) should not be used to determine whether a person is infected because the amount of tuberculin injected intradermally cannot be precisely controlled. Tuberculin skin testing is both safe and reliable throughout the course of pregnancy. The Mantoux tuberculin test is performed by placing an intradermal injection of 0.1 mL of tuberculin into the inner surface of the forearm. The test must be performed with tuberculin that has at least the same strength as either 5 tuberculin units (TU) of standard purified protein derivative (PPD) S or 2 TU of PPD RT 23, Statens Seruminstitut, as recommended by the World Health Organization. PPD strengths of 1 TU or 250 TU are not acceptable (Menzies, 2000). Using a disposable tuberculin syringe with the needle bevel facing upward, the injection should be made just beneath the surface of the skin. This should produce a discrete, pale elevation of the skin (a wheal) 6 mm to 10 mm in diameter. To prevent needle-stick injuries, needles should not be recapped, purposely bent or broken, removed from disposable syringes, or otherwise manipulated by hand. After they are used, disposable needles and syringes should be placed in puncture-resistant containers for disposal. Institutional guidelines regarding universal precautions for infection control (e.g., the use of gloves) should be followed. A trained health care worker, preferably the investigator, should read the reaction to the Mantoux test 48 to 72 hours after the injection. Subjects should never be allowed to read their own tuberculin skin test results. If a subject fails to show up for the scheduled reading, a positive reaction may still be measurable up to 1 week after testing. However, if a subject who fails to return within 72 hours has a negative test, tuberculin testing should be repeated. The area of induration (palpable raised hardened area) around the site of injection is the reaction to tuberculin. For standardization, the diameter of the induration should be measured transversely (perpendicular) to the long axis of the forearm. Erythema (redness) should not be measured. All reactions should be recorded in millimeters, even those classified as negative.

Interpreting the Tuberculin Skin Test Results

In the US and many other countries, the most conservative definition of positivity for the tuberculin skin test is reserved for immunocompromised patients, and this definition is to be applied in this study to maximize the likelihood of detecting latent TB, even though the subjects may not be immunocompromised at baseline.

In the US and Canada, an induration of 5 mm or greater in response to the intradermal tuberculin skin test is considered to be a positive result and evidence for either latent or active TB.

In countries outside the US and Canada, country-specific guidelines for immunocompromised patients should be consulted for the interpretation of tuberculin skin test results. If no local country guidelines for immunocompromised patients exist, US guidelines must be followed.

Treatment of Latent Tuberculosis

Local country guidelines for immunocompromised patients should be consulted for acceptable anti-tuberculous treatment regimens for latent TB. If no local country guidelines for immunocompromised patients exist, US guidelines must be followed.

REFERENCES

Centers for Disease Control and Prevention. Core curriculum on tuberculosis: What the clinician should know (Fourth Edition). Atlanta, GA: Department of Health and Human Services; Centers for Disease Control and Prevention; National Center for HIV, STD, and TB Prevention; Division of Tuberculosis Elimination; 2000:25-86.

Menzies R I. Tuberculin skin testing. In: Reichman L B, Hershfield E S (eds). Tuberculosis, a comprehensive international approach. 2nd ed. New York, NY: Marcel Dekker, Inc; 2000:279-322.

Appendix 4: HBV Screening and Monitoring

Subjects must undergo screening for hepatitis B virus (HBV). At a minimum, this includes testing for HBsAg (HBV surface antigen), anti-HBs (HBV surface antibody), and anti-HBc total (HBV core antibody total):

1) Subjects who test negative for all HBV screening tests (i.e., HBsAg−, anti-HBc−, and anti-HBs−) are eligible for this study.

2) Subjects who test negative for surface antigen (HBsAg−) and test positive for core antibody (anti-HBc+) and surface antibody (anti-HBs+) are eligible for this study.

3) Subjects who test positive only for surface antibody (anti-HBs+) are eligible for this study.

4) Subjects who test positive for surface antigen (HBsAg+) are NOT eligible for this study, regardless of the results of other hepatitis B tests.

5) Subjects who test positive only for core antibody (anti-HBc+) must undergo further testing for the presence of hepatitis B virus deoxyribonucleic acid (HBV DNA test). If the HBV DNA test is positive, the subject is NOT eligible for this study. If the HBV DNA test is negative, the subject is eligible for this study. In the event the HBV DNA test cannot be performed, the subject is NOT eligible for this study.

For subjects who are not eligible for this study due to HBV test results, consultation with a physician with expertise in the treatment of hepatitis B virus infection is recommended

| Eligibility based on hepatitis B virus test results | | | |
|---|---|---|---|
| | Hepatitis B test result | | |
| Action | Hepatitis B surface antigen (HBsAg) | Hepatitis B surface antibody (anti-HBs) | Hepatitis B core antibody (anti-HBc total) |
| Include | – | – | – |
| | – | + | – |
| | – | + | + |
| Exclude | + | – or + | – or + |
| Require testing for presence HBV DNA* | – | – | + |

*If HBV DNA is detectable, exclude from the clinical study. If HBV DNA testing cannot be performed, or there is evidence of chronic liver disease, exclude from the clinical study.

What is claimed:

1. A method comprising:
   i) administering an anti-IL-12/IL-23p40 antibody to a patient with active Systemic Lupus Erythematosus (SLE) in a clinically proven safe and clinically proven effective amount, wherein the antibody comprises a heavy chain of the amino acid sequence of SEQ ID NO: 10 and a light chain of the amino acid sequence of SEQ ID NO: 11, wherein the antibody is administered with an initial intravenous (IV) dose at 6.0 mg of antibody/kg of the patient ±1.5 mg/kg, followed by administrations of a subcutaneous (SC) dose of 90 mg of antibody every 8 weeks (q8w), or wherein the antibody is administered as an initial subcutaneous (SC) dose, followed by administrations of a SC dose every 8 weeks (q8w), wherein the IV dose of the antibody is in a pharmaceutical composition comprising a solution comprising 10 mM L-histidine, 8.5% (w/v) sucrose, 0.04% (w/v) polysorbate 80, 0.4 mg/mL L methionine, and 20 µg/mL EDTA disodium salt, dehydrate, at pH 6.0, and wherein the SC dose of the antibody is in a pharmaceutical composition comprising a solution comprising 6.7 mM L-histidine, 7.6% (w/v) sucrose, 0.004% (w/v) polysorbate 80, at pH 6.0; and
   ii) achieving a response selected from the group consisting of: (a) a 50% improvement from baseline in Cutaneous Lupus Erythematosus Disease Area and Severity Index (CLASI) score by week 24 of treatment with the antibody; and (b) a statistically significant improvement in disease activity as determined by a 50% improvement from baseline joint disease activity by week 24 of treatment with the antibody.

2. The method of claim 1, wherein the response is 50% improvement from baseline in Cutaneous Lupus Erythematosus Disease Area and Severity Index (CLASI) score.

3. The method of claim 1, wherein the response is sustained through 1 year of treatment.

4. The method of claim 1, further comprising administering to the patient one or more additional drugs for treating lupus.

5. The method of claim 4, wherein the additional drug is selected from the group consisting of: immunosuppressive agents, non-steroidal anti-inflammatory drugs (NSAIDs), methotrexate (MTX), anti-B-cell surface marker antibodies, angiotensin converting enzyme inhibitors, angiotensin receptor blockers, anti-malarials, mycophenolate mofetil, mycophenolic acid, azathioprine,6-mercaptopurine, belimumab, anti-CD20 antibodies, rituximab, corticosteroids, and co-stimulatory modifiers.

* * * * *

SEQUENCE LISTING

```
<160> NUMBER OF SEQ ID NOS: 11

<210> SEQ ID NO 1
<211> LENGTH: 5
<212> TYPE: PRT
<213> ORGANISM: Homo sapiens

<400> SEQUENCE: 1

Thr Tyr Trp Leu Gly
1               5

<210> SEQ ID NO 2
<211> LENGTH: 17
<212> TYPE: PRT
<213> ORGANISM: Homo sapiens

<400> SEQUENCE: 2

Ile Met Ser Pro Val Asp Ser Asp Ile Arg Tyr Ser Pro Ser Phe Gln
1               5                   10                  15

Gly

<210> SEQ ID NO 3
<211> LENGTH: 10
<212> TYPE: PRT
<213> ORGANISM: Homo sapiens

<400> SEQUENCE: 3

Arg Arg Pro Gly Gln Gly Tyr Phe Asp Phe
1               5                   10

<210> SEQ ID NO 4
<211> LENGTH: 11
<212> TYPE: PRT
<213> ORGANISM: Homo sapiens

<400> SEQUENCE: 4

Arg Ala Ser Gln Gly Ile Ser Ser Trp Leu Ala
1               5                   10

<210> SEQ ID NO 5
<211> LENGTH: 7
<212> TYPE: PRT
<213> ORGANISM: Homo sapiens

<400> SEQUENCE: 5

Ala Ala Ser Ser Leu Gln Ser
```

```
<210> SEQ ID NO 6
<211> LENGTH: 9
<212> TYPE: PRT
<213> ORGANISM: Homo sapiens

<400> SEQUENCE: 6

Gln Gln Tyr Asn Ile Tyr Pro Tyr Thr
1               5

<210> SEQ ID NO 7
<211> LENGTH: 119
<212> TYPE: PRT
<213> ORGANISM: Homo sapiens

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
            100                 105                 110

Thr Leu Val Thr Val Ser Ser
        115

<210> SEQ ID NO 8
<211> LENGTH: 108
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys Arg
            100                 105

<210> SEQ ID NO 9
<211> LENGTH: 503
<212> TYPE: PRT
<213> ORGANISM: Homo sapiens
```

<400> SEQUENCE: 9

```
Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Ile Trp Glu Leu Lys Lys Asp Val Tyr Val Val
        195                 200                 205

Glu Leu Asp Trp Tyr Pro Asp Ala Pro Gly Glu Met Val Val Leu Thr
210                 215                 220

Cys Asp Thr Pro Glu Glu Asp Gly Ile Thr Trp Thr Leu Asp Gln Ser
225                 230                 235                 240

Ser Glu Val Leu Gly Ser Gly Lys Thr Leu Thr Ile Gln Val Lys Glu
                245                 250                 255

Phe Gly Asp Ala Gly Gln Tyr Thr Cys His Lys Gly Gly Glu Val Leu
            260                 265                 270

Ser His Ser Leu Leu Leu Leu His Lys Lys Glu Asp Gly Ile Trp Ser
        275                 280                 285

Thr Asp Ile Leu Lys Asp Gln Lys Glu Pro Lys Asn Lys Thr Phe Leu
290                 295                 300

Arg Cys Glu Ala Lys Asn Tyr Ser Gly Arg Phe Thr Cys Trp Trp Leu
305                 310                 315                 320

Thr Thr Ile Ser Thr Asp Leu Thr Phe Ser Val Lys Ser Ser Arg Gly
                325                 330                 335

Ser Ser Asp Pro Gln Gly Val Thr Cys Gly Ala Ala Thr Leu Ser Ala
            340                 345                 350

Glu Arg Val Arg Gly Asp Asn Lys Glu Tyr Glu Tyr Ser Val Glu Cys
        355                 360                 365

Gln Glu Asp Ser Ala Cys Pro Ala Ala Glu Glu Ser Leu Pro Ile Glu
370                 375                 380

Val Met Val Asp Ala Val His Lys Leu Lys Tyr Glu Asn Tyr Thr Ser
385                 390                 395                 400

Ser Phe Phe Ile Arg Asp Ile Ile Lys Pro Asp Pro Pro Lys Asn Leu
```

```
                405                 410                 415
Gln Leu Lys Pro Leu Lys Asn Ser Arg Gln Val Glu Val Ser Trp Glu
            420                 425                 430

Tyr Pro Asp Thr Trp Ser Thr Pro His Ser Tyr Phe Ser Leu Thr Phe
            435                 440                 445

Cys Val Gln Val Gln Gly Lys Ser Lys Arg Glu Lys Lys Asp Arg Val
450                 455                 460

Phe Thr Asp Lys Thr Ser Ala Thr Val Ile Cys Arg Lys Asn Ala Ser
465                 470                 475                 480

Ile Ser Val Arg Ala Gln Asp Arg Tyr Tyr Ser Ser Ser Trp Ser Glu
                485                 490                 495

Trp Ala Ser Val Pro Cys Ser
            500

<210> SEQ ID NO 10
<211> LENGTH: 449
<212> TYPE: PRT
<213> ORGANISM: Homo sapiens

<400> SEQUENCE: 10

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
            100                 105                 110

Thr Leu Val Thr Val Ser Ser Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 11
<211> LENGTH: 214
<212> TYPE: PRT
<213> ORGANISM: Homo sapiens

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

```
Ala Cys Glu Val Thr His Gln Gly Leu Ser Ser Pro Val Thr Lys Ser
    195                 200                 205

Phe Asn Arg Gly Glu Cys
    210
```